(12) United States Patent
Wagner et al.

(10) Patent No.: US 8,222,485 B2
(45) Date of Patent: Jul. 17, 2012

(54) GENERATION OF PLANTS WITH IMPROVED PATHOGEN RESISTANCE

(75) Inventors: D. Ry Wagner, Pleasant Hill, OR (US); Shoshan Haran, Kibbutz Beeri (IL)

(73) Assignee: Agrinomics LLC, Portland, OR (US)

( * ) Notice: Subject to any disclaimer, the term of this patent is extended or adjusted under 35 U.S.C. 154(b) by 646 days.

(21) Appl. No.: 12/304,343

(22) PCT Filed: Jun. 13, 2007

(86) PCT No.: PCT/US2007/071144
§ 371 (c)(1),
(2), (4) Date: Dec. 11, 2008

(87) PCT Pub. No.: WO2007/147016
PCT Pub. Date: Dec. 21, 2007

(65) Prior Publication Data
US 2009/0222942 A1 Sep. 3, 2009

Related U.S. Application Data

(60) Provisional application No. 60/813,662, filed on Jun. 13, 2006.

(51) Int. Cl.
*A01H 5/00* (2006.01)
*A01H 5/10* (2006.01)
*C12N 15/09* (2006.01)
*C12N 15/82* (2006.01)

(52) U.S. Cl. ........ 800/279; 800/278; 800/298; 800/295; 435/468; 435/419

(58) Field of Classification Search .......................... None
See application file for complete search history.

(56) References Cited

U.S. PATENT DOCUMENTS

| 5,783,393 | A | 7/1998 | Kellogg et al. |
| 5,783,394 | A | 7/1998 | Bestwick et al. |
| 5,859,330 | A | 1/1999 | Bestwick et al. |
| 2004/0096424 | A1* | 5/2004 | Frommer et al. ............ 424/85.1 |
| 2004/0248304 | A1 | 12/2004 | Hu et al. |

FOREIGN PATENT DOCUMENTS

| EP | 1 496 122 | 1/2005 |
| WO | WO 00/04040 | 1/2000 |
| WO | WO 00/56863 | 9/2000 |
| WO | WO 01/83679 | 8/2001 |
| WO | WO 01/83697 | 11/2001 |
| WO | WO 02/20791 | 3/2002 |
| WO | WO 03/081978 | 10/2003 |
| WO | WO 03/091412 | 11/2003 |

OTHER PUBLICATIONS

Ishida et al., "High efficiency transformation of maize (*Zea mays* L.) mediated by *Agrobacterium tumefaciens*," *Nature Biotechnology*, 14:745-750, 1996.

Jones et al., "Effective vectors for transformation, expression of heterologous genes, and assaying transposon excision in transgenic plants," *Transgenic Res.*, 1:285-297, 1992.

Kaloshian et al., "Genetic and physical localization of the root-knot nematode resistance locus mi in tomato," *Mol. Gen. Genet.*, 257:376-385; 1998.

Klein et al., "High-velocity microprojectiles for delivering nucleic acids into living cells," *Nature*, 327:70-73, 1987.

Milligan et al., "The root knot nematode resistance gene Mi from tomato is a member of the leucine zipper, nucleotide binding, leucine-rich repeat family of plant genes," *Plant Cell*, 10:1307-1319, 1998.

Rushton et al., "Synthetic plant promoters containing defined regulatory elements provide novel insights into pathogen- and wound-induced signaling," *The Plant Cell*, 14:749-762, 2002.

Van Der Voort et al., "Tight Physical Linkage of the Nematode Resistance Gene Gpa2 and the Virus Resistance Gene Rx on a Single Segment Introgressed from the Wild Species *Solanum tuberosum* subsp. Andigena CPC 1673 into Cultivated Potato," *Mol. Plant-Microbe Int.*, 12:197-206, 1999.

Van Der Vossen et al., "Homologues of a single resistance-gene cluster in potato confer resistance to distinct pathogens: a virus and a nematode," *Plant J.*, 23:567-576, 2000.

Van Haaren & Houck, "A functional map of the fruit-specific promoter of the tomato 2A11 gene," *Plant. Mol. Biol.*, 21:625-640, 1993.

Verdaguer et al., "Functional organization of the cassava vein mosaic virus (CsVMV) promoter," *Plant Mol. Biol.*, 37:1055-1067, 1998.

Weigel et al., "Activation tagging in *Arabidopsis*," *Plant Physiology*, 122:1003-1013, 2000.

Williamson, "Root-knot nematode resistance genes in tomato and their potential for future use," *Annu. Rev. Phytopathol.*, 36:277-293, 1998.

Goggin et al., "Heterologous Expression of the *Mi-1.2* Gene from Tomato Confers Resistance Against Nematodes but Not Aphids in Eggplant," *MPMI*, 19(4):383-388, 2006.

Sze et al., "Expression Patterns of a Novel AtCHX Gene Family Highlight Potential Roles in Osmotic Adjustment and K*I* Homeostasis in Pollen Development[1[w]]," *Plant Physiology*, 136:2532-2547, 2004.

Cai et al., "Positional cloning of a gene for nematode resistance in sugar beet," *Science*, 275:832-834, 1997.

Christou et al., "Inheritance and expression of foreign genes in transgenic soybean plants," *Proc. Natl. Acad. Sci U.S.A.*, 86:7500-7504, 1989.

De Block et al., "Transformation of *Brassica napus* and *Brassica oleracea* Using *Agrobacterium tumefaciens* and the Expression of the bar and neo Genes in the Transgenic Plants," *Plant Physiol.*, 91:694-701, 1989.

De Majnik et al., "The cre1 and cre3 nematode resistance genes are located at homologous loci in the wheat genome," *Mol. Plant Microbe Interact.*, 16:1129-1134, 2003.

(Continued)

*Primary Examiner* — Medina A Ibrahim

(74) *Attorney, Agent, or Firm* — Klarquist Sparkman, LLP.

(57) ABSTRACT

The present disclosure is directed to plants that display a modified pathogen resistance phenotype (e.g., increased nematode resistance) due to altered expression of an NMR nucleic acid. The invention is further directed to methods of generating plants with a modified pathogen resistance phenotype.

7 Claims, No Drawings

OTHER PUBLICATIONS

Ernst et al., "The broad-spectrum potato cyst nematode resistance gene (Hero) from tomato is the only member of a large gene family of NBS-LRR genes with an unusual amino acid repeat in the LRR region," *Plant J.*, 31:127-136, 2002.

Everett et al., "Genetic Engineering of Sunflower (*Helianthus annuus* L.)," *Bio/Technology*, 5:1201-1204, 1987.

Fromm et al., "Inheritance and expression of chimeric genes in the progeny of transgenic maize plants," *Biotechnology*, 8:833-839, 1990.

Chen et al., "*CaMi*, a root-knot nematode resistance gene from hot pepper (*Capsium annuum* L.) confers nematode resistance in tomato," *Plant Cell Rep*, 26:895-905, 2007.

Goggin et al., "Heterologous Expression of the *Mi*-1.2 Gene from Tomato Confers Resistance Against Nematodes but Not Aphids in Eggplant," *Mol. Plant-Microbe Interact.*, 19(4):383-388, 2006.

Paal et al., "Molecular cloning of the potato *Gro1-4* gene conferring resistance to pathotype Ro1 of the root cyst nematode *Globodera rostochiensis*, based on a candidate gene approach," *The Plant Journal*, 38:285-297, 2004.

GenBank Accession No. NM_100870, 2006 (2 pages).

Lemoine, "Sucrose transporters in plants: update on function and structure," *Biochimica et Biophysica Acta*, 1465: 246-262, 2000.

\* cited by examiner

GENERATION OF PLANTS WITH IMPROVED PATHOGEN RESISTANCE

CROSS REFERENCE TO RELATED APPLICATION(S)

This the U.S. National Stage of International Application No. PCT/US2007/071144, filed Jun. 13, 2007 (which was published in English under PCT Article 21(2)), which in turn claims the benefit of U.S. Provisional Application No. 60/813,662, filed Jun. 13, 2006. Both applications are incorporated herein by reference.

BACKGROUND

The control of infection by plant pathogens, which can inhibit production of fruits, seeds, foliage and flowers and cause reductions in the quality and quantity of the harvested crops, is of significant economic importance. Pathogens annually cause billions of dollars in damage to crops worldwide (Baker et al. 1997, *Science* 276:726-733). Consequently, an increasing amount of research has been dedicated to developing novel methods for controlling plant diseases. Such studies have centered on the plant's innate ability to resist pathogen invasion in an effort to buttress the plant's own defenses to counter pathogen attacks (Staskawicz et al. 1995, *Science* 268:661-667; Baker et al. supra).

Although most crops are treated with agricultural pesticidal agents, such as anti-fungal and anti-bacterial agents, damage from pathogenic infection still results in revenue losses to the agricultural industry on a regular basis. Furthermore, many of the agents used to control such infection or infestation cause adverse side effects to the plant and/or to the environment. Plants with enhanced resistance to infection by pathogens would decrease or eliminate the need for application of chemical pesticidal, anti-fungal and anti-bacterial agents. There has been significant interest in developing transgenic plants that show increased resistance to a broad range of pathogens (Atkinson et al., 2003, *Annu. Rev. Phytopathol.* 41:615-639; Williamson and Gleason, 2003, *Curr. Opin. Plant Biol*, 6:327-333; Stuiver and Custers, 2001, *Nature* 411:865-8; Melchers and Stuiver, 2000, *Curr. Opin. Plant Biol* 3:147-152; Rommens and Kishore, 2000, *Curr. Opin. Biotechnol.* 11:120-125; Williamson, 1999, *Curr. Opin. Plant Biol* 2:327-331; Mourgues et al 1998, *Trends Biotechnol* 16:203-210).

Plant pathogenic nematodes are small invertebrate animals that feed on the roots of crops causing damage to the plants and reducing yield of the crops. Nematodes of the family Heteroderidae cause the most economic damage among plant parasitic nematodes (Williamson, 1999, *Curr. Opin. Plant Biol* 2:327-331). This family of parasitic nematodes can be divided into two groups: the root-knot nematodes (genus *Meloidogyne*) and the cyst nematodes (genera *Heterodera* and *Globodera*). Infection of host plants by the root-knot nematodes usually results in the formation of root galls or 'root-knots', and causes severe loss in yield in many crops. By contrast, cyst nematodes often have narrower host ranges. *Arabidopsis thaliana*, which is amendable to molecular genetics experiments, is an important model for providing insights into plant-nematode interactions because it is a host for several species of root-knot and cyst nematodes (Sijmons et al., 1991, *Plant J.*, 1:245-254).

A number of genes whose mis-expression is associated with altered resistance to nematodes have been identified in several crop species. For examples, the Mi gene of tomato confers resistance against several root-knot nematode species (Williamson, 1998, *Annu. Rev. Phytopathol* 36:277-293). Mi protein contains NBS (nucleotide binding site) and LRR (leucine rich repeats) domains (Kaloshian et al., 1998, *Mol. Gen. Genet.*, 257:376-385; Milligan et al., 1998, *Plant Cell* 10:1307-1319). The Hs1$^{pro-1}$ gene of a wild relative of sugar beet confers resistance to the cyst nematode *Heterodera schachtii* (Cai et al., 1997, *Science*, 275:832-834). Hs1$^{pro-1}$ protein contains a predicted signal sequence, a predicted trans-membrane region and a leucine-rich region. The Gpa2 gene of potato confers resistance against some isolates of the cyst nematode *Globodera pallida* (van der Voort et al., 1999, *Mol. Plant-Microbe Int.*, 12:187-206; van der Vossen, 2000, *Plant J.*, 23:567-576). The Hero gene of tomato confers resistance to potato cyst nematodes such as *Globodera rostochiensis* and *G. pallida* (Ernst et al., 2002, *Plant J.*, 31:127-136). The Gpa2 and Hero proteins, similar to the Mi protein, contain the NBS and LRR domains. Lastly, the Cre1 gene of wheat confers resistance to most European nematodes and the only Australian pathotype; whereas the Cre3 gene of wheat confers resistance to the Australian nematodes (de Majnik J et al., 2003, *Mol. Plant Microbe Interact.* 16:1129-1134). The Cre1 and Cre3 genes have not been cloned.

Due to the importance of pathogen resistance in plants, methods for producing plants with increased pathogen resistance are desirable.

SUMMARY OF THE DISCLOSURE

The disclosure provides a transgenic plant having increased resistance to a pathogen, such as a nematode, relative to control plants. The transgenic plant has incorporated (e.g., stably incorporated) into its genome a DNA construct comprising a nucleotide sequence that encodes a protein having pathogen resistance activity. The nucleotide sequence may be a nucleotide sequence identified in column 3 of Tables 3 and 4, or a complement thereof; a nucleotide sequence having at least 90% sequence identity to a nucleotide sequence identified in column 3 of Tables 3 and 4, or a complement thereof; a nucleotide sequence encoding a polypeptide comprising an amino acid sequence identified in column 4 of Tables 3 and 4; or a nucleotide sequence encoding a polypeptide having at least 90% sequence identity to an amino acid sequence identified in column 4 of Tables 3 and 4. The nucleotide sequence is operably linked to a promoter that drives expression of a coding sequence in a plant cell. In some embodiments, the transgenic plant is selected from the group consisting of rapeseed, soy, corn, sunflower, cotton, cocoa, safflower, oil palm, coconut palm, flax, castor and peanut, tomato, carrot, lettuce, bean, asparagus, cauliflower, pepper, beetroot, cabbage, eggplant, endive, leek, long cucumber, melon, pea, radish, rootstock, short cucumber (Beït alpha), squash, watermelon, white onion, witloof, yellow onion, broccoli, brussel sprout, bunching onion, celery, mache, cucumber, fennel, gourd, pumpkin, sweet corn, and zucchini.

The transgenic plants may be produced by introducing into the plant or a cell thereof at least one plant transformation vector comprising a nucleotide sequence that encodes or is complementary to a sequence that encodes an NMR polypeptide identified in column 4 of Tables 3 and 4, or a variant thereof, and growing the transformed plant or cell to produce a transgenic plant, wherein said transgenic plant exhibits increased resistance to at least one pathogen. In one embodiment, the NMR polypeptide has at least about 70% sequence identity to an amino acid sequence referred to in column 4 of Tables 3 and 4. In other embodiments, the NMR polypeptide has at least about 80% or 90% sequence identity (or more) to or has the amino acid sequence referred to in column 4 of Tables 3 and 4.

Methods are provided for producing a plant with increased pathogen resistance, including increased nematode resistance, comprising identifying a plant having an altered NMR gene, and generating progeny of the plant, wherein the progeny have increased pathogen resistance, and wherein the NMR gene is one that is identified in column 4 of Tables 3 and 4. Methods are also provided for identifying a plant having increased pathogen resistance, comprising analyzing at least one NMR gene from the plant, and identifying a plant with an altered NMR gene, wherein the plant has increased pathogen resistance. The invention further provides plants and plant parts obtained by the methods described herein.

SEQUENCE LISTING

The nucleic and/or amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1 and 2 are the mRNA (GI 18407880|ref|NM_14362.1|) and protein (gi|15230551|ref|NP_190079.1) sequences of *Arabidopsis thaliana* ATCHX10; monovalent cation:proton antiporter (ATCHX10).

SEQ ID NOs: 3 and 4 are the mRNA (GI|22331603|ref|NM_148843.1|) and protein (gi|22331604|ref|NP_680096.1) sequences of *Arabidopsis thaliana* unknown protein (AT3G44935).

SEQ ID NOs: 5 and 6 are the mRNA (GI|30692415|ref|NM_114363.2|) and protein (gi|30692416|ref|NP_190080.2) sequences of *Arabidopsis thaliana* unknown protein (AT3G44940).

SEQ ID NOs: 7 and 8 are the mRNA (GI|18407884|ref|NM_114364.1|) and protein (gi|15230556|ref|NP_190081.1) sequences of *Arabidopsis thaliana* unknown protein (AT3G44950).

SEQ ID NOs: 9 and 10 are the mRNA (GI|30688921|ref|NM_122240.2|) and protein (gi|15237286|ref|NP_197725.1) sequences of *Arabidopsis thaliana* unknown protein (AT5G23340).

SEQ ID NOs: 11 and 12 are the mRNA (GI|22327006|ref|NM_122241.2|) and protein (gi|15237287|ref|NP_197726.1) sequences of *Arabidopsis thaliana* unknown protein (AT5G23350).

SEQ ID NOs: 13 and 14 are the mRNA (GI|42568032|ref|NM_122242.3| and protein (gi|15237288|ref|NP_197727.1) sequences of *Arabidopsis thaliana* unknown protein (AT5G23360).

SEQ ID NOs: 15 and 16 are the mRNA (GI|22327007|ref|NM_122243.2|) and protein (gi|15237301|ref|NP_197728.1) sequences of *Arabidopsis thaliana* unknown protein (AT5G23370).

SEQ ID NOs: 17 and 18 are the mRNA (GI|30688942|ref|NM_122244.2|) and protein (gi|15237306|ref|NP_197729.1) sequences of *Arabidopsis thaliana* unknown protein (AT5G23380).

SEQ ID NOs: 19 and 20 are the mRNA (GI|30688951|ref|NM_122245.3|) and protein (gi|15237309|ref|NP_197730.1) sequences of *Arabidopsis thaliana* unknown protein (AT5G23390).

SEQ ID NOs: 21 and 22 are the mRNA (GI|42570036|ref|NM_147906.3|) and protein (gi|22327010|ref|NP_680211.1) sequences of *Arabidopsis thaliana* unknown protein (AT5G23395).

SEQ ID NOs: 23 and 24 are the mRNA (GI|18394598|ref|NM_101693.1) and protein (gi|15221060|ref|NP_173271.1) sequences of *Arabidopsis thaliana* ATMKK7; kinase (ATMKK7).

SEQ ID NOs: 25 and 26 are the mRNA (GI|30685820|ref|NM_101694.3|) and protein (gi|22329651|ref|NP_173272.2) sequences of *Arabidopsis thaliana* catalytic/hydrolase (AT1G18360).

SEQ ID NOs: 27 and 28 are the mRNA (GI|30685823|ref|NM_101695.3|) and protein (gi|22329653|ref|NP_173273.2) sequences of *Arabidopsis thaliana* HIK (HINKEL); ATP binding/microtubule motor (HIK).

SEQ ID NOs: 29 and 30 are the mRNA (GI|18394601|ref|NM_101696.1) and protein (gi|15221762|ref|NP_173274.1) sequences of *Arabidopsis thaliana* unknown protein (AT1G18380).

SEQ ID NOs: 31 and 32 are the mRNA (GI|18394602|ref|NM_101697.1|) and protein (gi|15221764|ref|NP_173275.1) sequences of *Arabidopsis thaliana* ATP binding/kinase/protein kinase/protein serine/threonine kinase/protein-tyrosine kinase (AT1G18390).

SEQ ID NOs: 33 and 34 are the mRNA (GI|30685839|ref|NM_101698.2|) and protein (gi|30685840|ref|NP_173276.2) sequences of *Arabidopsis thaliana* transcription factor (AT1G18400).

SEQ ID NOs: 35 and 36 are the mRNA (GI|18409867|ref|NM_115219.1) and protein (gi|15231843|ref|NP_190927.1) sequences of *Arabidopsis thaliana* ATP binding/protein kinase/protein serine/threonine kinase/protein-tyrosine kinase (AT3G53590).

SEQ ID NOs: 37 and 38 are the mRNA (GI|18409871|ref|NM_115220.1|) and protein (gi|15231845|ref|NP_190928.1) sequences of *Arabidopsis thaliana* nucleic acid binding/transcription factor/zinc ion binding (AT3G53600).

SEQ ID NOs: 39 and 40 are the mRNA (GI|42570491|ref|NM_180365.2|) and protein (gi|30693873|ref|NP_850696.1) sequences of *Arabidopsis thaliana* ATRAB8, GTP binding (ATRAB8).

SEQ ID NOs: 41 and 42 are the mRNA (GI|30693869|ref|NM_115221.2|) and protein (gi|15231847|ref|NP_190929.1) sequences of *Arabidopsis thaliana* ATRAB8, GTP binding (ATRAB8).

SEQ ID NOs: 43 and 44 are the mRNA (GI|8409875|ref|NM_115222.1|) and protein (gi|15231849|ref|NP_190930.1) sequences of *Arabidopsis thaliana* inorganic diphosphatase/magnesium ion binding/pyrophosphatase (AT3G53620).

SEQ ID NOs: 45 and 46 are the mRNA (GI|42565899|ref|NM_115223.4|) and protein (gi|22331772|ref|NP_190931.2) sequences of *Arabidopsis thaliana* unknown protein (AT3G53630).

SEQ ID NOs: 47 and 48 are the mRNA (GI|18409886|ref|NM_115224.1|) and protein (gi|15231853|ref|NP_190932.1) sequences of *Arabidopsis thaliana* ATP binding/kinase/protein kinase/protein serine/threonine kinase/protein-tyrosine kinase (AT3G53640).

SEQ ID NOs: 49 and 50 are the mRNA (GI|18409888|ref|NM_115225.1|) and protein (gi|15231854|ref|NP_190933.1) sequences of *Arabidopsis thaliana* DNA binding (AT3G53650).

SEQ ID NOs: 51 and 52 are the mRNA (GI|18391089|ref|NM_100867.1|) and protein (gi|15218331|ref|NP_172464.1) sequences of *Arabidopsis thaliana* ATOPT2; oligopeptide transporter (ATOPT2).

SEQ ID NOs: 53 and 54 are the mRNA (GI|30681449|ref|NM_179297.1|) and protein (gi|30681450|ref|NP_849628.1) sequences of *Arabidopsis thaliana* catalytic (AT1G09932).

SEQ ID NOs: 55 and 56 are the mRNA (GI|42570079|ref|NM_148453.2|) and protein (gi|42570080|ref|NP_683294.2) sequences of *Arabidopsis thaliana* catalytic (AT1G09935).

SEQ ID NOs: 57 and 58 are the mRNA (GI|30681461|ref|NM_100868.2|) and protein (gi|15218333|ref|NP_172465.1) sequences of *Arabidopsis thaliana* HEMA2; glutamyl-tRNA reductase (HEMA2).

SEQ ID NOs: 59 and 60 are the mRNA (GI|30681468|ref|NM_100869.2|) and protein (gi|15218335|ref|NP_172466.1) sequences of *Arabidopsis thaliana* unknown protein (AT1G09950).

SEQ ID NOs: 61 and 62 are the mRNA (GI|30681472|ref|NM_100870.2|) and protein (gi|15218362|ref|NP_172467.1) sequences of *Arabidopsis thaliana* SUT4 (SUCROSE TRANSPORTER 4); carbohydrate transporter/sucrose:hydrogen symporter/sugar porter (SUT4).

SEQ ID NOs: 63 and 64 are the mRNA (GI|18410812|ref|NM_106181.1|) and protein (gi|15222161|ref|NP_177661.1) sequences of *Arabidopsis thaliana* transcription factor (AT1G75250).

SEQ ID NOs: 65 and 66 are the mRNA (GI|30680419|ref|NM_100667.2|) and protein (gi|8390829|ref|NP_563800.1) sequences of *Arabidopsis thaliana* calmodulin binding/translation elongation factor (AT1G07930).

SEQ ID NOs: 67 and 68 are the mRNA (GI|30685575|ref|NM_101651.2|) and protein (gi|5220876|ref|NP_173230.1) sequences of *Arabidopsis thaliana* transcription factor (AT1G17880).

SEQ ID NOs: 69 and 70 are the mRNA (GI|30684274|ref|NM_101396.2|) and protein (gi|18394220|ref|NP_563969.1) sequences of *Arabidopsis thaliana* unknown protein (AT1G15270).

SEQ ID NOs: 71 and 72 are the mRNA (GI|130687074|ref|NM_129278.2|) and protein (gi|15228102|ref|NP_181259.1) sequences of *Arabidopsis thaliana* RNA binding/nucleic acid binding (AT2G37220).

SEQ ID NOs: 73 and 74 are the mRNA (GI|30683800|ref|NM_128379.2|) and protein (gi|8401659|ref|NP_565666.1) sequences of *Arabidopsis thaliana* CSD2 (COPPER/ZINC SUPEROXIDE DISMUTASE 2); copper, zinc superoxide dismutase (CSD2).

SEQ ID NOs: 75 and 76 are the mRNA (GI|42573723|ref|NM_203229.1|) and protein (gi|42573724|ref|NP_974958.1) sequences of *Arabidopsis thaliana* malate dehydrogenase/oxidoreductase (AT5G58330).

SEQ ID NOs: 77 and 78 are the mRNA (GI|42568623|ref|NM_125218.3|) and protein (gi|30697051|ref|NP_568875.2) sequences of *Arabidopsis thaliana* malate dehydrogenase/oxidoreductase (AT5G58330).

SEQ ID NOs: 79 and 80 are the mRNA (GI|42570606|ref|NM_180883.2|) and protein (gi|30697049|ref|NP_851214.1) sequences of *Arabidopsis thaliana* malate dehydrogenase/oxidoreductase (AT5G58330).

SEQ ID NOs: 81 and 82 are the mRNA (GI|42566395|ref|NM_117102.3|) and protein (gi|15235029|ref|NP_192772.1) sequences of *Arabidopsis thaliana* LHCB5 (LIGHT HARVESTING COMPLEX OF PHOTOSYSTEM II 5); chlorophyll binding (LHCB5).

SEQ ID NOs: 83 and 84 are the mRNA (GI|30682653|ref|NM_117468.2|) and protein (gi|5236376|ref|NP_193130.1) sequences of *Arabidopsis thaliana* HOG1 (HOMOLOGY-DEPENDENT GENE SILENCING 1); adenosylhomocysteinase (HOG1).

SEQ ID NOs: 85 and 86 are the mRNA (GI|18410828|ref|NM_115649.1|) and protein (gi|15230881|ref|NP_191346.1) sequences of *Arabidopsis thaliana* AHUS5; ubiquitin conjugating enzyme/ubiquitin-like activating enzyme (AHUS5).

SEQ ID NOs: 87 and 88 are the mRNA (GI|30696503|ref|NM_124849.2|) and protein (gi|15239706|ref|NP_200279.1) sequences of *Arabidopsis thaliana* DNA binding/transcription factor (AT5G54680).

DETAILED DESCRIPTION

Definitions

Unless otherwise indicated, all technical and scientific terms used herein have the same meaning as they would to one skilled in the art of the present invention. Practitioners are particularly directed to Sambrook et al., 1989, Molecular Cloning: A Laboratory Manual (Second Edition), Cold Spring Harbor Press, Plainview, N.Y., and Ausubel F M et al., 1993, Current Protocols in Molecular Biology, John Wiley & Sons, New York, N.Y., for definitions and terms of the art. It is to be understood that this invention is not limited to the particular methodology, protocols, and reagents described, as these may vary.

As used herein, the term "vector" or "transformation vector" refers to a nucleic acid construct designed for transfer between different host cells. An "expression vector" refers to a vector that has the ability to incorporate and express heterologous DNA fragments in a foreign cell. Many prokaryotic and eukaryotic vectors, including example expression vectors, are commercially available. Selection of appropriate vectors is within the knowledge of those having skill in the art.

A "heterologous" nucleic acid construct or sequence has at least a portion of the sequence that is not native to the plant cell in which it is expressed. Heterologous, with respect to a control sequence, refers to a control sequence (e.g., promoter or enhancer) that does not function in nature to regulate the same gene the expression of which it is currently regulating. Generally, heterologous nucleic acid sequences are not endogenous to the cell or part of the native genome in which they are present, and have been added to the cell by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. By "complement" is intended a nucleotide sequence that is sufficiently complementary to a given nucleotide sequence such that it can hybridize to the given nucleotide sequence to thereby form a stable duplex.

As used herein, "recombinant" includes reference to a cell or vector that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, includes, for example, "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, propagules, and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "interesting phenotype (trait)" with reference to a transgenic plant refers to an observable or measurable phenotype demonstrated by a T1 and/or subsequent generation plant, which is not displayed by the corresponding non-transgenic (e.g., a genotypically similar plant that has been raised or assayed under similar conditions). An interesting phenotype may represent an improvement in the plant or may provide a means to produce improvements in other plants. An "improvement" is a feature that may enhance the utility of a plant species or variety by providing the plant with a unique and/or novel quality.

An "altered pathogen resistance phenotype" or "altered pathogen resistance" refers to a detectable change in the response of a genetically modified plant to pathogenic infection, compared to the similar, but non-modified plant. The phenotype may be apparent in the plant itself (e.g., in growth, viability or particular tissue morphology of the plant) or may be apparent in the ability of the pathogen to proliferate on and/or infect the plant. As used herein, "improved pathogen resistance" refers to increased resistance to a pathogen. Methods for measuring pathogen resistance are well known in the art. See, for example, Epple et al., *Plant Cell,* 1997, 9:509-520, Jach et al., *Plant J.,* 1995, 8:97-109, Lorito et al., *Proc Natl Acad Sci USA,* 1998, 95:7860-7865, McDowell et al., *Plant J.,* 2000, 22:523-529, McDowell et al., *Mol Plant Microbe Interact.,* 2005, 18:1226-1234, Schweizer et al., *Plant Physiol.,* 1993, 102:503-511, Simons et al., *Plant Cell,* 1998, 10:1055-1068, Stein et al., *Plant Cell,* 2006, 18:731-746, Epub 2006 February 2006, Thomma et al., *Curr Opin Immunol.,* 2001, 13:63-68. By "pathogen resistance activity" or "pathogen resistance" is therefore intended the ability to grow or survive during a pathogenic infection.

An "altered nematode resistance phenotype" or "altered nematode resistance" refers to a detectable change in the response of a genetically modified plant to nematode infection, compared to the similar, but non-modified plant. The phenotype may be apparent in the plant itself (e.g., in growth, viability or particular tissue morphology of the plant) or may be apparent in the ability of the pathogen to proliferate on and/or infect the plant, or both. As used herein, "improved nematode resistance" refers to increased resistance to a nematode. Methods for measuring nematode resistance are well known in the art. See, for example, Cai et al., *Science,* 1997, 275:832-834, Kaloshian et al., *Mol Gen Genet.,* 1998, 257: 376-385, Milligan et al., *Plant Cell,* 1998, 10:1307-1319. By "nematode resistance activity" or "nematode resistance" is therefore intended the ability to grow or survive during a nematode infection.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The category of plants which can be used in the methods of the present disclosure is generally as broad as the category of higher plants amenable to transformation techniques, including both monocotyledenous and dicotyledenous plants.

As used herein, "transgenic plant" includes reference to a plant that comprises within its genome a heterologous polynucleotide. The heterologous polynucleotide can be either stably integrated into the genome, or can be extra-chromosomal. Preferably, the polynucleotide of the present disclosure is stably integrated into the genome such that the polynucleotide is passed on to successive generations. A plant cell, tissue, organ, or plant into which the heterologous polynucleotides have been introduced is considered "transformed," "transfected," or "transgenic." Direct and indirect progeny of transformed plants or plant cells that also contain the heterologous polynucleotide are also considered transgenic.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (e.g., sequences located at the 5' and 3' ends of the nucleic acid) in the genomic DNA of the organism from which the nucleic acid is derived. For purposes of the disclosure, "isolated" when used to refer to nucleic acid molecules excludes isolated chromosomes. For example, in various embodiments, the isolated NMR nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A NMR protein that is substantially free of cellular material includes preparations of protein having less than about 30%, 20%, 10%, or 5% (by dry weight) of non-NMR protein (also referred to herein as a "contaminating protein").

Identification of Plants with an Improved Pathogen Resistance Phenotype

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., *Science*, 1992, 258: 1350-1353; Weigel et al., *Plant Physiology*, 2000, 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., *Plant Cell*, 1996, 8:659-671; Schaffer et al., *Cell*, 1998, 93: 1219-1229; Fridborg et al., *Plant Cell*, 1999, 11: 1019-1032; Kardailsky et al., *Science*, 1999, 286:1962-1965; Christensen et al., 2000, *Cell* 100:469-478). In one example, activation tagging was used to identify mutants with altered disease resistance (Weigel et al., supra).

A screen of *Arabidopsis* activation tagged (ACTTAG) mutants was used to identify the genes [designated NMR# listed in column 1 of Tables 3 and 4 (below)] which are responsible for an altered pathogen resistance phenotype (specifically, a nematode resistance phenotype).

Briefly, and as further described in the Examples, a large number of *Arabidopsis* plants were mutated with the pSKI015 vector, which comprises a T-DNA from the Ti plasmid of *Agrobacterium tumefaciens*, a viral enhancer element, and a selectable marker gene (Weigel et al., *Plant Physiology*, 2000, 122:1003-1013). When the T-DNA inserts into the genome of transformed plants, the enhancer element can cause up-regulation of genes in the vicinity, generally within about 10 kilobase (kb) of the insertion. T1 plants were exposed to the selective agent in order to specifically recover transformed plants that expressed the selectable marker and therefore harbored T-DNA insertions. T1 plants were allowed to grow to maturity, self-fertilize and produce seed. T2 seed was harvested, labeled and stored. ACTTAG lines showing increased resistance to the nematode *Meloidogyne javanica* were identified either in a "forward genetics" or a "reverse genetics" screen.

ACTTAG lines that showed increase resistance to *M. javanica* were identified by comparing the phenotype of ACTTAG seedlings and of wild-type seedlings after *M. javanica* infection. The association of the NMR gene with the pathogen resistance phenotype was discovered by analysis of the genomic DNA sequence flanking the T-DNA insertion in the identified line. Accordingly, NMR genes and/or polypeptides may be employed in the development of genetically modified plants having a modified pathogen (e.g., nematode) resistance phenotype ("a NMR phenotype"). NMR genes may be used in the generation of crops and/or other plant species that have improved resistance to infection by *M. javanica*, other parasitic root-knot nematodes and other parasitic nematodes (e.g., parasitic cyst nematodes) and may also be useful in the generation of a plant with improved resistance to fungal, bacterial, and/or other pathogens. Mis-expression of NMR genes may thus reduce the need for fungicides and/or pesticides. The modified pathogen resistance phenotype may further enhance the overall health of the plant.

NMR Nucleic Acids and Polypeptides

The NMR genes discovered in the "forward genetics" activation tagging screen and "reverse genetics" activation tagging screen are listed in column 1 of Tables 3 and 4, respectively. The *Arabidopsis* Information Resource (TAIR) identification numbers are provided in column 2. Columns 3-4 provide GenBank identifier numbers (GT#s) for the nucleotide and polypeptide sequences, respectively; each of the referenced published sequences is incorporated herein by reference as of Jun. 13, 2006. Column 5 lists biochemical function and/or protein name. Column 6 lists the conserved protein domains. Column 7 provides the GI#s for nucleic acid and polypeptide sequences of orthologous genes from other plant species; each of the referenced published sequences is incorporated herein by reference as of the date on which this application is filed.

As used herein, the term "NMR polypeptide" refers to a full-length NMR protein as listed in column 1 of Tables 3 and 4. Fragments, derivatives (variants), or orthologs thereof that are "functionally active," meaning that the protein fragment, derivative, or ortholog exhibits one or more or the functional activities associated with the full-length NMR polypeptide, may also be used in the methods or compositions disclosed herein. By "fragment" is intended a portion of the nucleotide sequence encoding an NMR protein or a portion of the amino acid sequence of the NMR protein. A fragment of a nucleotide sequence may encode a biologically active portion of an NMR protein, a biologically active nucleic acid (e.g., an antisense or small inhibitory nucleic acid), or it may be a fragment that can be used as a hybridization probe or PCR primer using methods known in the art. Nucleic acid molecules that are fragments of an NMR nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1400, 1500, 2000, 2500, 3000 contiguous nucleotides, or up to the number of nucleotides present in a full-length NMR-encoding nucleotide sequence disclosed herein, depending upon the intended use.

By "contiguous" nucleotides or amino acids are intended nucleotide or amino acid residues that are immediately adjacent to one another.

In one embodiment, a functionally active NMR polypeptide causes an altered pathogen resistance phenotype when mis-expressed in a plant. In a further embodiment, mis-expression of the functionally active NMR polypeptide causes increased resistance to *M. javanica* and/or other parasitic nematodes. In another embodiment, a functionally active NMR polypeptide is capable of rescuing defective (including deficient) endogenous NMR activity when expressed in a plant or in plant cells; the rescuing polypeptide may be from the same or from a different species as that with defective activity. In another embodiment, a functionally active fragment of a full length NMR polypeptide (e.g., a native polypeptide having the sequence of an NMR polypeptide or a naturally occurring ortholog thereof) retains one of more of the biological properties associated with the full-length NMR polypeptide, such as signaling activity, binding activity, catalytic activity, or cellular or extra-cellular localizing activity.

The term signaling activity refers to the ability of a protein to function in the process of mediating a signal that induces a genetic, biochemical or physiological response of a plant to attack by a pathogen. See, e.g., Apel & Hirt, *Annu Rev Plant Biol.*, 2004, 55:373-399, Beckers & Spoel, *Plant Biol (Stuttg)* 2006, 8:1-10, Chisholm et al., *Cell*, 2006, 124:803-814, and Shah, *Annu Rev Phytopathol.*, 2005, 43:229-260.

The term binding activity refers to the ability of a protein to bind to another protein, a DNA fragment or some other molecule (e.g., Bogdanove, *Plant Mol Biol.*, 2002, 50:981-989, Inohara et al., *Annu Rev Biochem.*, 2005, 74:355-383, and Testerink & Munnik, *Trends Plant Sci.*, 2005, 10:368-375).

The term catalytic activity refers to the ability of a protein to catalyze a chemical reaction. See, for instance: Bhatia et al., *Crit Rev Biotechnol*, 2002, 22:375-407, Pedley & Martin, *Curr Opin Plant Biol*, 2005, 8:541-547, Rosahl, *Z Naturforsch [C]*, 1996, 51:123-138, and Stone & Walker, *Plant Physiol*, 1995, 108:451-457.

The term cellular or extra-cellular localizing activity refers to portions of the protein that interact with other components of the cell to localize the protein to a specific sub-cellular or extra-cellular location (Crofts et al., *Plant Physiol.*, 2004, 136:3414-3419, Matsuoka & Bednarek, *Curr Opin Plant Biol*, 1998, 1:463-469, Rusch & Kendall, *Mol Membr Biol*, 1995, 12:295-307, Schnell & Hebert, *Cell*, 2003, 112:491-505).

An NMR fragment preferably comprises an NMR domain, such as a C- or N-terminal or catalytic domain, among others, and may comprise at least about 15, 25, 30, 50, 75, 100, 125, 150, 175, 200, 250, 300, 350, 400, or 450 contiguous amino acids of an NMR protein, or up to the total number of amino acids present in a full-length NMR protein disclosed herein. Representative functional domains of NMR genes are listed in column 6 of Tables 3 and 4 and can be identified using the INTERPRO program (Mulder et al., 2003 *Nucleic Acids Res.* 31,315-318; Mulder et al., 2005 *Nucleic Acids Res.* 33:D201-D205). Functionally active variants of full-length NMR polypeptides or fragments thereof include polypeptides with amino acid insertions, deletions, or substitutions that retain one of more of the biological activities associated with the full-length NMR polypeptide. By "retains biological activity" is intended that the variant will have at least about 30%, preferably at least about 50%, more preferably at least about 70%, even more preferably at least about 80% of the biological activity of the native protein, such as for instance an anti-nematode activity. In some cases, variants are generated that change the post-translational processing of an NMR polypeptide. For instance, variants may have altered protein transport or protein localization characteristics or altered protein half-life compared to the native polypeptide.

As used herein, the term "NMR nucleic acid" encompasses nucleic acids with the sequence provided in the GenBank entry referenced in column 3 of Tables 3 and 4. Nucleic acid sequences complementary to the GenBank entry referenced in column 3 of Table 3 and Table 4, as well as functionally active fragments, derivatives, or orthologs thereof may also be used in the methods and compositions disclosed herein. An NMR nucleic acid of this disclosure may be DNA, derived from genomic DNA or cDNA, or RNA.

In one embodiment, a functionally active NMR nucleic acid encodes or is complementary to a nucleic acid that encodes a functionally active NMR polypeptide. Included within this definition is genomic DNA that serves as a template for a primary RNA transcript (e.g., an mRNA precursor) that requires processing, such as splicing, before encoding the functionally active NMR polypeptide. An NMR nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed NMR polypeptide, or an intermediate form. An NMR polynucleotide can also include heterologous coding sequences, for example, sequences that encode a marker included to facilitate the purification of the fused polypeptide, or a transformation marker.

In another embodiment, a functionally active NMR nucleic acid is capable of being used in the generation of loss-of-function pathogen resistance phenotypes, for instance, via antisense suppression, co-suppression, etc.

An NMR nucleic acid used in the methods of this disclosure may comprise a nucleic acid sequence that encodes or is complementary to a sequence that encodes an NMR polypeptide having at least about 60%, about 70%, about 75%, about 80%, about 85%, about 90%, about 91%, about 92%, about 93%, about 94%, about 95%, about 96%, about 97%, about 98%, or about 99% sequence identity to the polypeptide sequence of the GenBank entry referenced in column 4 of Tables 3 and 4. In another embodiment an NMR polypeptide of the disclosure may include a conserved protein domain of the NMR polypeptide, such as the protein domain(s) listed in column 6 of Tables 3 and 4. In another embodiment, an NMR polypeptide comprises a polypeptide sequence with at least about 50%, about 60%, about 70%, about 80%, about 85%, about 90% or about 95% or more sequence identity to a functionally active fragment of the polypeptide of the GenBank entry referenced in column 4 of Tables 3 and 4. In yet another embodiment, an NMR polypeptide comprises a polypeptide sequence with at least about 50%, about 60%, about 70%, about 80%, or about 90% identity to the polypeptide sequence of the GenBank entry referenced in column 4 of Tables 3 and 4 over its entire length and comprises a conserved protein domain(s) listed in column 6 of Tables 3 and 4.

In another embodiment, an NMR nucleic acid sequence used in the methods of the present disclosure comprises a nucleic acid sequence that has at least about 60%, about 70%, about 75%, about 80%, about 85%, about 90%, about 91%, about 92%, about 93%, about 94%, about 95%, about 96%, about 97%, about 98%, or about 99% sequence identity to the nucleic acid sequence of the GenBank entry referenced in column 3 of Tables 3 and 4, or nucleic acid sequences that are complementary to such an NMR sequence, or a functionally active fragment thereof.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., *J. Mol. Biol.*, 215:403-410, 1990) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Variants" of NMR-encoding nucleotide sequences include those sequences that encode the NMR proteins disclosed herein but that differ conservatively because of the degeneracy of the genetic code as well as those that have a specific sequence identity as discussed above. For example, preferably, conservative amino acid substitutions may be made at one or more predicted, preferably nonessential amino acid residues. A "nonessential" amino acid residue is a residue that can be altered from the wild-type sequence of an NMR protein without altering the biological activity, whereas an "essential" amino acid residue is required for biological activity. Amino acid substitutions may be made in non-conserved regions that retain function. In general, such substitutions would not be made for conserved amino acid residues, or for amino acid residues residing within a conserved motif, where such residues are essential for protein activity.

Derivative nucleic acid molecules of the subject nucleic acid molecules include sequences that selectively hybridize to the nucleic acid sequence of the GenBank entry referenced in column 3 of Tables 3 and 4. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers (1994); Sambrook et al., supra). In some embodiments, a nucleic acid molecule of the disclosure is capable of hybridizing to a nucleic acid molecule containing the nucleotide sequence of the GenBank entry referenced in column 3 of Tables 3 and 4 under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 hour in a solution containing 0.2×SSC and 0.1% SDS (sodium dodecyl sulfate). In other embodiments, moderately stringent hybridization conditions are used that comprise: pretreatment of filters containing nucleic acid for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a NMR polypeptide can be produced. For example, codons may be selected to increase the rate at which expression of the polypeptide occurs in a particular host species, in accordance with the optimum codon usage dictated by the particular host organism (see, e.g., Nakamura et al., 1999, *Nucleic Acids Res.*, 27:292). Such sequence variants may be used in the methods of this disclosure.

The methods of the disclosure may use orthologs of the *Arabidopsis* NMR genes. Examples of orthologs of each of the *Arabidopsis* NMR genes are identified in column 7 of Tables 3 and 4. Methods of identifying the orthologs in other plant species are known in the art. Normally, orthologs in different species retain the same function, due to the presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (MA and Bork P, 1998, *Proc. Natl. Acad. Sci. U.S.A.*, 95:5849-5856; Huynen M A et al., *Genome Research* (2000) 10:1204-1210). Programs for multiple sequence alignment, such as CLUSTAL (Thompson J D et al., 1994, *Nucleic Acids Res.* 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, supra; Dieffenbach and Dveksler (Eds.) PCR Primer: A Laboratory Manual, Cold Spring Harbor Laboratory Press, NY, 1989). For instance, methods for generating a cDNA library from the plant species of interest and probing the library with partially homologous gene probes are described in Sambrook et al., supra. A highly conserved portion of the *Arabidopsis* NMR coding sequence may be used as a probe. NMR ortholog nucleic acids may hybridize to the nucleic acid of the GenBank entry referenced in column 3 of Tables 3 and 4 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known NMR polypeptides are used for ortholog isolation. Western blot analysis can determine that a NMR ortholog (e.g., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., supra. Once candidate ortholog(s) are identified by any of these means, candidate orthologous sequence are used as bait (the "query") for the reverse BLAST against sequences from *Arabidopsis* or other species in which NMR nucleic acid and/or polypeptide sequences have been identified.

NMR nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991, *Methods Enzymol.*, 204:125-39) or PCR-mediated mutagenesis, may be used to introduce desired changes into a cloned nucleic acid.

In general, the methods of the disclosure involve incorporating the desired form of the NMR nucleic acid into a plant expression vector for transformation of plant cells, and the NMR polypeptide is expressed in the host plant.

Generation of Genetically Modified Plants with a Pathogen Resistance Phenotype

NMR nucleic acids and polypeptides may be used in the generation of genetically modified plants having a modified pathogen resistance phenotype; in general, improved resistance phenotypes are of interest. In one embodiment, altered expression of the NMR gene in a plant is used to generate plants with increased resistance to *M. javanica*. In further embodiments, plants that mis-express NMR may also display altered resistance to parasitic nematode pathogens including, but not limited to, *Meloidogyne* spp, *Heterodera* spp, *Globodera* spp., *Nacobbus* spp., *Belonolaimus* spp., *Criconemoides* spp., *Helicotylenchus* spp., *Xiphinema* spp., *Longidorus* spp., *Pratylenchus* spp., *Paratrichodorus* spp., *Tylenchorhynchus* spp., *Ditylenchus* spp., *Hoplolaimus* spp., and *Rotylenchulus* spp. Increased resistance to fungal pathogens is also of interest. The fungal pathogens include, but are not limited to, *Alternaria brassicicola*, *Botrytis cinerea*, *Erysiphe cichoracearum*, *Fusarium oxysporum*, *Plasmodiophora brassica*, *Rhizoctonia solani*, *Colletotrichum coccode*, *Sclerotinia* spp., *Aspergillus* spp., *Penicillium* spp., *Ustilago* spp., and *Tilletia* spp. Bacterial pathogens of interest include, but are not limited to, *Agrobacterium tumefaciens*, *Erwinia tracheiphila*, *Erwinia stewartii*, *Xanthomonasphaseoli*, *Erwinia amylovora*, *Erwinia carotovora*, *Pseudomonas syringae*, *Pelargonium* spp, *Pseudomonas cichorii*, *Xanthomonas fragariae*, *Pseudomonas morsprunorum*, *Xanthomonas campestris*. Pathogenic infection may affect seeds, fruits, blossoms, foliage, stems, tubers, roots, etc. Accordingly, resistance may be observed in any part of the plant.

The methods described herein are generally applicable to all plants as the NMR gene (or an ortholog, variant or fragment thereof) may be expressed in any type of plant. In some embodiments, the disclosure is directed to crops such as maize, soybean, cot on, rice, wheat, barley, tomato, canola, turfgrass, and flax. Other crops include alfalfa, tobacco, and other forage crops. The disclosure may also be directed to fruit- and vegetable-bearing plants including tomato, carrot, lettuce, bean, asparagus, cauliflower, pepper, beetroot, cabbage, eggplant, endive, leek, long cucumber, melon, pea, radish, rootstock, short cucumber (Beït alpha), squash, watermelon, white onion, witloof, and yellow onion, bunching onion, broccoli, brussel sprout, celery, mache, cucumber, fennel, pumpkin, sweet corn, and zucchini, plants used in the cut flower industry, grain-producing plants, oil-producing plants, and nut-producing plants, among others.

The skilled artisan will recognize that a wide variety of transformation techniques exist in the art, and new techniques are continually becoming available. Any technique that is suitable for the target host plant can be employed within the scope of the present disclosure. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising a NMR polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.).

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as maize (Fromm et al., *Biotechnology*, 1990, 8:833-839; Ishida et al., 1996, *Nature Biotechnology*

14:745-750), rapeseed (De Block et al., 1989, *Plant Physiol.,* 91:694-701), sunflower (Everett et al., 1987, *Bio/Technology,* 5:1201) and soybean (Christou et al., 1989, *Proc. Natl. Acad. Sci U.S.A.,* 86:7500-7504; 1989; Kline et al., 1987, *Nature,* 327:70).

Expression (including transcription and translation) of a NMR gene may be regulated with respect to the level of expression, the tissue type(s) where expression takes place and/or the developmental stage of expression. A number of heterologous regulatory sequences (e.g., promoters and enhancers) are available for controlling the expression of a NMR nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the 35S CaMV (Jones J D et al., 1992, *Transgenic Res.,* 1:285-297), the CsVMV promoter (Verdaguer B et al., 1998, *Plant Mol. Biol.,* 37:1055-1067) and the melon actin promoter (published PCT application WO00/56863). Exemplary tissue-specific promoters include the tomato E4 and E8 promoters (U.S. Pat. No. 5,859,330) and the tomato 2AII gene promoter (Van Haaren M J J et al., 1993, *Plant Mot. Biol.,* 21:625-640). In one embodiment, the NMR gene expression is under the control of a pathogen-inducible promoter (Rushton et al., 2002, *The Plant Cell,* 14:749-762). In one embodiment, expression of the NMR gene is under control of regulatory sequences from genes whose expression is associated with the CsVMV promoter.

In yet another aspect, it may be desirable to inhibit the expression of the endogenous NMR gene in a host cell. Exemplary methods for practicing this aspect of the disclosure include, but are not limited to, antisense suppression (Smith, et al., 1988, *Nature,* 334:724-726; van der Krol et al., 1988, *Biotechniques,* 6:958-976); co-suppression (Napoli, et al., 1990, *Plant Cell,* 2:279-289); ribozymes (PCT Publication WO 97/10328); and combinations of sense and antisense (Waterhouse, et al., 1998, *Proc. Natl. Acad. Sci. U.S.A.,* 95: 13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988, *Proc. Natl. Acad. Sci. U.S.A.,* 85:8805-8809), a partial cDNA sequence including fragments of 5' coding sequence, (Cannon et al., 1990, *Plant Mol. Biol.,* 15:39-47), or 3' non-coding sequences (Ch'ng et al., 1989, *Proc. Natl. Acad. Sci. U.S.A.,* 86:10006-10010). Cosuppression techniques may use the entire cDNA sequence (Napoli et al., supra; van der Krol et al., 1990, *The Plant Cell,* 2:291-299), or a partial cDNA sequence (Smith et al., 1990, *Mol. Gen. Genetics,* 224:477-481).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing (VIGS) (see Baulcombe, 1999, *Arch. Virol. Suppl.* 15:189-201).

In a representative application, expression profiling, generally by microarray analysis, is used to simultaneously measure differences or induced changes in the expression of many different genes. Techniques for microarray analysis are well known in the art (see, for example, Schena et al., 1995, *Science,* 270:467-470; Baldwin et al., 1999, *Cur. Opin. Plant Biol.,* 2(2):96-103; Dangond, 2000, *Physiol. Genomics,* 2:53-58; van Hal N L et al., 2000, *J. Biotechnol.,* 78:271-280; Richmond and Somerville, 2000, *Cur. Opin. Plant Biol.,* 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with a Pathogen Resistance Phenotype

The disclosure further provides a method of identifying plants having increased pathogen resistance, in particular, plants that have a mutation in an endogenous NMR gene that confers such resistance. This method comprises analyzing at least one NMR gene from a population of plants, and identifying a plant with an altered (e.g., mutated) NMR gene. The NMR gene may have a mutation that confers the pathogen resistance, or it may have an altered expression as compared to a wild-type plant. Pathogen-resistant progeny of these plants that are not genetically modified may be generated. Methods for producing and identifying plants with mutations that confer pathogen resistance are known in the art. In one method, called "TILLING" (for targeting induced local lesions in genomes), mutations are induced in the seed of a plant of interest, for example, using EMS treatment. The resulting plants are grown and self-fertilized, and the progeny are used to prepare DNA samples. PCR amplification and sequencing of the NMR gene is used to identify whether a mutated plant has a mutation in the NMR gene. Plants having NMR mutations may then be tested for pathogen resistance, or alternatively, plants may be tested for pathogen resistance, and then PCR amplification and sequencing of the NMR gene is used to determine whether a plant having increased pathogen resistance has a mutated NMR gene. TILLING can identify mutations that may alter the expression of specific genes or the activity of proteins encoded by these genes (see Colbert et al., 2001, *Plant Physiol.* 126:480-484; McCallum et al., 2000, *Nature Biotechnology* 18:455-457).

In another method, a candidate gene/Quantitative Trait Loci (QTLs) approach can be used in a marker-assisted breeding program to identify mutations in the NMR gene or orthologs of NMR gene that may confer resistance to pathogens (see Foolad et al., *Theor. Appl. Genet.,* 2002, 104(6-7): 945-958; Rothan et al., 2002, *Theor. Appl. Genet.,* 105(1): 145-159; Dekkers and Hospital, 2002, *Nat. Rev. Genet.,* 3:22-32). Thus, in a further aspect of the disclosure, a NMR nucleic acid is used to identify whether a pathogen-resistant plant has a mutation in the endogenous NMR gene or has a particular allele that causes a pathogen resistance phenotype.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced public databases (as of the date of filing of this application) are also incorporated by reference.

EXAMPLES

Example 1

Generation of Plants with a Pathogen Resistance Phenotype by Transformation with an Activation Tagging Construct Mutants were generated using the activation tagging (ACT-TAG) vector, pSKI015 (GI 6537289; Weigel D et al., supra). Standard methods were used for the generation of *Arabidopsis* transgenic plants, and were essentially as described in published application PCT WO01/83697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4× CaMV 35S enhancer element. Transgenic plants were selected at the T1 generation based on herbicide resistance. T2 seed was collected from T1 plants and stored in an indexed collection, and a portion of the T2 seed was accessed for the forward genetic screen. T3 seed was used in the reverse genetic screen. T2 seed was sown in soil and plants were exposed to the herbicide to kill plants lacking the ACTTAG vector. T2 plants were grown to maturity, allowed to self-fertilize and set seed. T3 seed (from the T2 plants) was harvested in bulk for each line, and a portion of the T3 seed was accessed for the reverse genetic screen (see below).

The position of the ACTTAG element in the genome in each line was determined using T3 seed by inverse PCR. The PCR product was subjected to sequence analysis and placed on the genome using a basic BLASTN search and/or a search of the *Arabidopsis* Information Resource (TAIR) database (available at the *Arabidopsis*.org website). 38,090 lines with recovered flanking sequences were considered in the reverse genetic screen.

Example 2

Forward Genetic Screen for Lines Resistant to the Nematode *Meloidogine javanica*

The forward genetics screen was conducted as a primary and secondary screen. In the primary screen, approximately 8 T2 seed from lines from the *Arabidopsis* ACTTAG collection and 2 seed from wild-type Col-0 were planted in soil. The seeds were stratified for 2 days at 4° C. and grown in a growth chamber at 25° C. with 60-70% relative humidity on a short-day light cycle of 10 hours light and 14 hours dark for 8 days. The soil around each seedling was inoculated with 5000 eggs of the nematode *Meloidogine javanica* and the plants were allowed to grow for 20-25 more days. Each plant was then removed from the soil and evaluated for stress caused by the nematode. Any lines with a plant showing no stress were submitted for further analysis.

In the secondary screen, approximately 40 T2 seeds are planted along with wild-type Col-0 seed. Plants were grown and inoculated with nematode eggs as in the primary screen. The plants were evaluated for stress 20-25 days after inoculation. All the lines that have at least one plant showing no stress were allowed to grow for 5 additional weeks. After this time, the plants are removed from the soil, the root system was washed and plants were evaluated for root knots found on the root system. Plants were rated as resistant if they had less than 20 knots on their root system.

As a result of these analyses, 48 ACTTAG lines were identified as resistant to the nematode *Meloidogine javanica*.

Example 3

Characterization of the T-DNA Insertion in Plants Exhibiting the Nematode Resistance Phenotype: ACTTAG Locus Number Determination and ACTTAG Copy Number Determination Because ACTTAG lines may have inserts at more than one genetic locus, the number of genetic loci containing the ACT-TAG inserts was estimated in each line identified in Example 2. In T1 plants, ACTTAG inserts are present in the hemizygous state (that is, they are present inserted in one of the two copies of the genome of the diploid plant). Because of genetic segregation, in T2 plants each genetic locus containing an ACTTAG insert is present in a 3:1 ratio; 75% of the T2 plants will have the ACTTAG insert at that locus and 25% will not. If a T1 plant contains two ACTTAG elements at independently segregating loci, the number of T2 plants containing any ACTTAG element will be 87.5% and 12.5% of the plants will not contain an insert. Because each ACTTAG element contains a gene conferring resistance to the herbicide BASTA, the number of genetic loci containing an ACTTAG element can be estimated by determining the percentage of T2 plants that are resistant to BASTA.

To determine the number of genetic loci carrying ACTTAG inserts in each line, the proportion T2 plants resistant to the selective agent 50-100 T2 seeds were sown in soil, allowed to germinate, and the number of germinated T2 seedlings was recorded. The T2 seedlings were sprayed with 60 mg/L of the herbicide BASTA 6 times over a period of 2 weeks to kill plants lacking the ACTTAG inserts. The number of BASTA resistant T2 seedlings was determined and the percentage of BASTA resistant plants calculated. Lines that had 60-80% BASTA-resistant T2 seedlings were estimated to carry an ACTTAG insert at a single genetic locus. Lines that had greater than 80% BASTA-resistant T2 seedlings were estimated to carry an ACTTAG insert at more than one genetic locus.

Because each genetic locus can contain more than one insert, the number of ACTTAG elements was estimated in each line identified in Example 2. To determine the number of ACTTAG inserts present in each line, a TaqMan® polymerase chain reaction (PCR) based method was used using TaqMan® Universal PCR master Mix (Applied Biosystems) and ABI PRISM 7700 Sequence Detection System (Applied Biosystems). Briefly, genomic DNA was isolated from a pool of at least 18 T2 seedlings. Two PCR reactions were carried out simultaneously in a reaction mixture using the DNA of an ACTTAG line as the template. One PCR reaction detects the presence of the BAR gene, which confers resistance to the herbicide glufosinate-ammonium, using the PCR primers specific to the BAR gene. The other PCR reaction detects the presence of the ELF3 gene in *Arabidopsis* using PCR primers specific to the ELF3 gene. The relative amounts of the two PCR products accumulated during the course of the reaction were used to determine the ACTTAG copy number.

Based on these analyses, five ACTTAG lines were chosen for further analysis (see Example 4). The ACTTAG locus number estimate and ACTTAG copy number estimate for these lines are show in Table 1 below.

TABLE 1

ACTTAG locus number estimate and ACTTAG copy number estimate for 5 nematode resistant lines.

| 1. Alias | 2. T1 Plant ID | 3. ORIGINAL RELEASE ID | 4. Probable number of ACTTAG loci | 5. Number of T2 seedlings germinated | 6. Number of basta resistant T2 seedlings | 7. Percent of basta resistant T2 seedlings (%) | 8. Taqman estimate of ACTTAG copy number |
|---|---|---|---|---|---|---|---|
| NMR1 | W000101067 | H000287 | 1 | 184 | 144 | 78.26 | 16 |
| NMR2 | W000101277 | H000418 | 1 | 254 | 158 | 62.20 | 1 |
| NMR3 | W000101176 | H000357 | 1 | 98 | 63 | 64.29 | 0.8 |
| NMR4 | W000117051 | H010126 | 1 | 90 | 68 | 75.56 | 2.3 |
| NMR5 | W000118068 | H010773 | 1 | 102 | 74 | 72.55 | 1.2 |

Example 4

Characterization of the T-DNA Insertion in Plants Exhibiting the Nematode Resistance Phenotype: Determination of ACTTAG Insertion Site in the *Arabidopsis* Genome Plasmid rescue (Weigel et al., supra) and/or inverse PCR (iPCR; Triglia et al., 1988, *Nucleic Acid Res.*, 16:8186) was used to recover *Arabidopsis* genomic DNA flanking the T-DNA insertion of lines identified in the forward genetic screen. The products of these analyses were analyzed by DNA sequencing and the sequence was subjected to a basic BLASTN search of the *Arabidopsis* genome housed in the Exelixis database or in the *Arabidopsis* Information Resource (TAIR) database (available at the *Arabidopsis*.org website). The location of the ACTTAGs for NMR1, NMR2, NMR3, NMR4 and NMR5 are described below.

NMR1: The right border of the ACTTAG insert is just upstream of nucleotide ~5042 of *Arabidopsis thaliana* DNA chromosome 3, BAC clone F14D17 (>gi|7671394|emb|AL353992.1|ATF14D17). The opposite flank of this insert was determined to be a left border, just downstream from nucleotide ~5042 of *Arabidopsis thaliana* DNA chromosome 3, BAC clone F14D17 (>gi|7671394|).

NMR2: The left border of the ACTTAG insert is just upstream of nucleotide ~931 *Arabidopsis thaliana* genomic DNA, chromosome 5, BAC clone:T32G24 (>gi|4589451|dbj|AB025642.1|AB025642).

NMR3: The left border of the ACTTAG insert is just downstream of nucleotide ~51143 *Arabidopsis thaliana* genomic DNA, chromosome 1, BAC clone:F15H18 (>gi|6684172). The opposite flank, which is a left border, is just upstream from nucleotide ~51333 of *Arabidopsis thaliana* DNA chromosome 1, BAC clone:F15H18 (>gi|6684172).

NMR4: The left border of the ACTTAG insert is just upstream of nucleotide ~120310 *Arabidopsis thaliana* genomic DNA, chromosome 3, BAC clone:F4P12 (>gi|6434215). The opposite flank, which is a left border, is just downstream from nucleotide ~120307 of *Arabidopsis thaliana* DNA chromosome 3, BAC clone:F4P12 (>gi|6434215).

NMR5: The right border of the ACTTAG insert is just upstream of nucleotide ~126494 *Arabidopsis thaliana* genomic DNA, chromosome 1, BAC clone:F21M12 (>gi|2160155). The opposite flank, which is a right border, is just downstream from nucleotide ~126507 of *Arabidopsis thaliana* DNA chromosome 1, BAC clone:F21M12 (>gi|2160155).

Example 5

Identification and Expression Analysis of Candidate Genes in ACTTAG Plants Exhibiting the Altered Pathogen Resistance Phenotype Genes with the translation initiation codons within about 10 kbp of the ACTTAG inserts in the nematode resistant lines are considered to be within "activation space". The expressions of these candidate genes are likely to be up-regulated in the nematode resistant lines due to the 4×CaMV 35S enhancer elements in the ACTTAG inserts. The candidate genes for the ACTTAG lines NMR1, NMR2, NMR3, NMR4 and NMR5 are listed in column 2 of Table 2.

These candidate genes were analyzed for altered expression in leaves of 30 day-old BASTA resistant T2 plants grown under 10 hr light 14 hr dark cycle in convirons. Wild-type plants grown in the same flat and therefore the same environmental conditions were used as controls for the SYBR green dye real-time quantitative RT-PCR assay. Specifically, RNA was extracted from tissues derived from plants exhibiting the pathogen resistance phenotype and from wild-type COL-0 plants. SYBR green dye real-time quantitative RT-PCR was performed using primers specific to the genes with sequence IDs presented in column 3 of Table 2 and to a constitutively expressed actin gene (ACT2, positive control). The results of the expression analyses of the candidate genes for the ACTTAG lines NMR1, NMR2, NMR3, NMR4 and NMR5 are shown in column 5 of Table 2.

TABLE 2

Expression analysis of the candidate genes for the ACTTAG lines NMR1, NMR2, NMR3, NMR4 and NMR5

| 1. Alias | 2. TAIR ID | 3. Nucleic Acid seq. GI# | 4. Biochemical function/protein name | 5. Expression analysis in ACTTAG line compared with Col-0 |
|---|---|---|---|---|
| NMR1 A | At3g44930 | gi|18407880 | cation/hydrogen exchanger | Not detectable |
| NMR1 B | At3g44935 | gi|22331603 | hypothetical protein | Not detectable |
| NMR1 C | At3g44940 | gi|30692415 | expressed protein predicted protein | No change |
| NMR1 D | At3g44950 | gi|18407884 | glycine-rich protein | Not detectable |
| NMR2 A | At5g23340 | gi|30688921 | expressed protein similar to glucose regulated repressor protein | No change |
| NMR2 B | At5g23350 | gi|22327006 | ABA-responsive protein | No change |

TABLE 2-continued

Expression analysis of the candidate genes for the ACTTAG lines NMR1, NMR2, NMR3, NMR4 and NMR5

| 1. Alias | 2. TAIR ID | 3. Nucleic Acid seq. GI# | 4. Biochemical function/protein name | 5. Expression analysis in ACTTAG line compared with Col-0 |
|---|---|---|---|---|
| NMR2 C | At5g23360 | gi\|42568032 | ABA-responsive protein | No change |
| NMR2 D | At5g23370 | gi\|22327007 | ABA-responsive protein | No change |
| NMR2 E | At5g23380 | gi\|30688942 | expressed protein | No change |
| NMR2 F | At5g23390 | gi\|30688951 | expressed protein | No change |
| NMR2 G | At5g23395 | gi\|42570036 | expressed protein | No change |
| NMR3 A | At1g18350 | gi\|18394598 | mitogen-activated protein kinase kinase (MAPKK) | No change |
| NMR3 B | At1g18360 | gi\|30685820 | hydrolase | No change |
| NMR3 C | At1g18370 | gi\|30685823 | kinesin heavy chain isolog | No change |
| NMR3 D | At1g18380 | gi\|18394601 | hypothetical protein | No change |
| NMR3 E | At1g18390 | gi\|18394602 | protein kinase | No change |
| NMR3 F | At1g18400 | gi\|30685839 | helix-loop-helix protein homolog | No change |
| NMR4 A | At3g53590 | gi\|18409867 | leucine-rich repeat transmembrane protein kinase, putative CLV1 receptor | No change |
| NMR4 B | At3g53600 | gi\|18409871 | zinc finger - like protein Zat11 zinc finger protein | No change |
| NMR4 C | At3g53610 | gi\|42570491 | Ras-related GTP-binding protein | No change |
| NMR4 D | At3g53620 | gi\|18409875 | inorganic pyrophosphatase - related protein inorganic pyrophosphatase | No change |
| NMR4 E | At3g53630 | gi\|42565899 | expressed protein predicted proteins | No change |
| NMR4 F | At3g53640 | gi\|18409886 | protein kinase | Not detectable |
| NMR4 G | At3g53650 | gi\|18409888 | histone H2B, putative similar to histone H2B from *Lycopersicon esculentum* | No change |
| NMR5 A | At1g09930 | gi\|18391089 | hypothetical protein Similar to *S. pombe* ISP4 (gb\|D83992) | Up-regulated 3 fold in NMR5 ACTTAG line |
| NMR5 B | At1g09932 | gi\|30681449 | expressed protein | Up-regulated 2 fold in NMR5 ACTTAG line |
| NMR5 C | At1g09935 | gi\|42570079 | ZW10-related protein | Up-regulated 2 fold in NMR5 ACTTAG line |
| NMR5 D | At1g09940 | gi\|30681461 | glutamyl-tRNA reductase 2 (GluTR) (HEMA2) | Up-regulated 10 fold in NMR5 ACTTAG line |
| NMR5 E | At1g09950 | gi\|30681468 | expressed protein Similar to *Nicotiana* tumor-related protein (gb\|26453) | Up-regulated 81 fold in NMR5 ACTTAG line |
| NMR5 F | At1g09960 | gi\|30681472 | sucrose transporter SUT4 (sucrose-proton symporter) | No change |

Example 6

Analysis of *Arabidopsis* NMR Sequence

Analyses of the NMR sequences were performed with BLAST (Altschul et al., 1990, *J. Mol. Biol.* 215:403-410), PFAM (Bateman et al., 1999, *Nucleic Acids Res.* 27:260-262), and/or INTERPRO (Mulder et al., 2003 *Nucleic Acids Res.* 31, 315-318; Mulder et al., 2005 *Nucleic Acids Res.* 33:D201-D205). The results of these analyses are listed in Table 3.

TABLE 3

Analysis of *Arabidopsis* NMR Sequences identified in a forward genetic screen

| 1. Gene alias | 2. TAIR | 3. Nucleic Acid seq. GI# | 4. Polypeptide seq. GI# | 5. Biochemical function/protein name | 6. Conserved protein domain | 7. Orthologous Genes: Nucleic Acid GI# | Polypeptide seq. GI# | Species |
|---|---|---|---|---|---|---|---|---|
| NMR1 A | At3g44930 | gi\|18407880 | gi\|15230551 | cation/hydrogen exchanger, putative (CHX10) | IPR006153 Sodium/hydrogen exchanger | gi\|18407876 | gi\|15230549 | *Arabidopsis thaliana* |
|  |  |  |  |  | IPR009627 Protein of unknown function UPF0259 | gi\|18407875 | gi\|15230547 | *Arabidopsis thaliana* |
|  |  |  |  |  |  | gi:18420618 | gi:15237167 | *Arabidopsis thaliana* |
| NMR1 B | At3g44935 | gi\|22331603 | gi\|22331604 | hypothetical protein | IPR002885 Pentatricopeptide repeat | gi\|22327129 | gi\|22327130 | *Arabidopsis thaliana* |
|  |  |  |  |  |  | gi\|18401472 | gi\|15226200 | *Arabidopsis thaliana* |
|  |  |  |  |  |  | gi\|28564706 | gi\|57899529 | *Oryza sativa* (japonica cultivar-group) |

TABLE 3-continued

Analysis of *Arabidopsis* NMR Sequences identified in a forward genetic screen

| 1. Gene alias | 2. TAIR | 3. Nucleic Acid seq. GI# | 4. Polypeptide seq. GI# | 5. Biochemical function/protein name | 6. Conserved protein domain | 7. Orthologous Genes: Nucleic Acid/Polypeptide seq. GI# | | |
|---|---|---|---|---|---|---|---|---|
| | | | | | | Nucleic Acid GI# | Polypeptide GI# | Species |
| NMR1 C | At3g44940 | gi|30692415 | gi|30692416 | expressed protein | PF07795 Protein of unknown function (DUF1635) | gi|18420620 | gi|15237171 | *Arabidopsis thaliana* |
| | | | | | | gi|42569404 | gi|42569405 | *Arabidopsis thaliana* |
| | | | | | | gi|55168326 | gi|55168327 | *Oryza sativa* (*japonica* cultivar-group) |
| NMR1 D | At3g44950 | gi|18407884 | gi|15230556 | glycine-rich protein expressed protein | | | | |
| NMR2 A | At5g23340 | gi|30688921 | gi|15237286 | | IPR007089 Leucine-rich repeat, cysteine-containing | gi|50911005 | gi|50911006 | *Oryza sativa* (*japonica* cultivar-group) |
| | | | | | IPR001611 Leucine-rich repeat | gi|62654403 | gi|62654404 | *Rattus norvegicus* |
| | | | | | | gi|26336706 | gi|26336707 | *Mus musculus* |
| NMR2 B | At5g23350 | gi|22327006 | gi|15237287 | GRAM domain-containing protein/ ABA-responsive protein-related | IPR004182 GRAM domain | gi|22327007 | gi|15237301 | *Arabidopsis thaliana* |
| | | | | | | gi|42568032 | gi|15237288 | *Arabidopsis thaliana* |
| | | | | | | gi|30682350 | gi|15241598 | *Arabidopsis thaliana* |
| NMR2 C | At5g23360 | gi|42568032 | gi|15237288 | GRAM domain-containing protein/ ABA-responsive protein-related | IPR004182 GRAM domain | gi|22327006 | gi|15237287 | *Arabidopsis thaliana* |
| | | | | | | gi|22327007 | gi|15237301 | *Arabidopsis thaliana* |
| | | | | | | gi|30682350 | gi|15241598 | *Arabidopsis thaliana* |
| NMR2 D | At5g23370 | gi|22327007 | gi|15237301 | GRAM domain-containing protein/ ABA-responsive protein-related | IPR004182 GRAM domain | gi|22327006 | gi|15237287 | *Arabidopsis thaliana* |
| | | | | | | gi|42568032 | gi|15237287 | *Arabidopsis thaliana* |
| | | | | | | gi|30682350 | gi|15241598 | *Arabidopsis thaliana* |
| NMR2 E | At5g23380 | gi|30688942 | gi|15237306 | expressed protein | IPR008507 Protein of unknown function DUF789 | gi|30679483 | gi|22328289 | *Arabidopsis thaliana* |
| | | | | | | gi|42561661 | gi|18379117 | *Arabidopsis thaliana* |
| | | | | | | gi|13161359 | gi|56201637 | *Oryza sativa* (*japonica* cultivar-group) |
| NMR2 F | At5g23390 | gi|30688951 | gi|15237309 | expressed protein | IPR006927 Protein of unknown function DUF639 | gi|50911037 | gi|50911038 | *Oryza sativa* (*japonica* cultivar-group) |
| | | | | | | gi|54781382 | gi|50911040 | *Oryza sativa* (*japonica* cultivar-group) |
| | | | | | | gi|30694422 | gi|22330119 | *Arabidopsis thaliana* |
| NMR2 G | At5g23395 | gi|42570036 | gi|22327010 | expressed protein | IPR010625 CHCH domain | gi:50926603 | gi:50926604 | *Oryza sativa* (*japonica* cultivar-group) |
| | | | | | | gi|50754422 | gi|50754423 | *Gallus gallus* |
| | | | | | | gi:49074187 | gi:49074188 | *Ustilago maydis* 521 |
| NMR3 A | At1g18350 | gi|18394598 | gi|15221060 | mitogen-activated protein kinase kinase (MAPKK), putative (MKK7) | IPR000719 Protein kinase domain | gi|30698945 | gi|15219482 | *Arabidopsis thaliana* |
| | | | | | IPR002290 Serine/threonine protein kinase | gi|51471931 | gi|51471932 | *Lycopersicon esculentum* |
| | | | | | | gi|18397509 | gi|15230671 | *Arabidopsis thaliana* |

TABLE 3-continued

Analysis of *Arabidopsis* NMR Sequences identified in a forward genetic screen

| 1. Gene alias | 2. TAIR | 3. Nucleic Acid seq. GI# | 4. Polypeptide seq. GI# | 5. Biochemical function/protein name | 6. Conserved protein domain | 7. Orthologous Genes: Nucleic Acid/Polypeptide seq. GI# | | |
|---|---|---|---|---|---|---|---|---|
| | | | | | | Nucleic Acid GI# | Polypeptide GI# | Species |
| NMR3 B | At1g18360 | gi\|30685820 | gi\|22329651 | hydrolase, alpha/beta fold family protein | IPR000073 Alpha/beta hydrolase fold | gi\|30698943 | gi\|18410366 | *Arabidopsis thaliana* |
| | | | | | IPR000379 Esterase/lipase/ thioesterase | gi\|50900229 | gi\|50900230 | *Oryza sativa* (*japonica* cultivar-group) |
| | | | | | IPR003089 Alpha/beta hydrolase | gi\|2801535 | gi\|2801536 | *Oryza sativa* |
| NMR3 C | At1g18370 | gi\|30685823 | gi\|22329653 | kinesin motor family protein (NACK1) | IPR001752 Kinesin, motor region | gi\|19570246 | gi\|19570247 | *Nicotiana tabacum* |
| | | | | | | gi\|30690897 | gi\|30690898 | *Arabidopsis thaliana* |
| | | | | | | gi\|19570248 | gi\|19570249 | *Nicotiana tabacum* |
| NMR3 D | At1g18380 | gi\|18394601 | gi\|15221762 | expressed protein | | gi\|22330477 | gi\|22330478 | *Arabidopsis thaliana* |
| | | | | | | gi\|62857019 | gi\|62857020 | *Lotus corniculatus* var. *japonicus* |
| | | | | | | gi\|42572012 | gi\|42572013 | *Arabidopsis thaliana* |
| NMR3 E | At1g18390 | gi\|18394602 | gi\|15221764 | protein kinase family protein | IPR000719 Protein kinase domain | gi\|55770126 | gi\|55770127 | *Oryza sativa* (*japonica* cultivar-group) |
| | | | | | IPR002290 Serine/threonine protein kinase | gi\|50900613 | gi\|50900614 | *Oryza sativa* (*japonica* cultivar-group) |
| | | | | | IPR000687 Protein of unknown function RIO1 | gi\|30697421 | gi\|30697422 | *Arabidopsis thaliana* |
| NMR3 F | At1g18400 | gi\|30685839 | gi\|30685840 | basic helix-loop-helix (bHLH) family protein | IPR001092 Basic helix-loop-helix dimerisation region bHLH | gi\|54654157 | gi\|58743491 | *Brassica oleracea* |
| | | | | | | gi\|30698966 | gi\|30698967 | *Arabidopsis thaliana* |
| | | | | | | gi\|30689166 | gi\|18395643 | *Arabidopsis thaliana* |
| NMR4 A | At3g53590 | gi\|18409867 | gi\|15231843 | leucine-rich repeat transmembrane protein kinase, putative | IPR000719 Protein kinase domain | gi\|30679853 | gi\|15222211 | *Arabidopsis thaliana* |
| | | | | | IPR002290 Serine/threonine protein kinase | gi\|20146211 | gi\|57900293 | *Oryza sativa* (*japonica* cultivar-group) |
| | | | | | IPR001611 Leucine-rich repeat IPR003591 Leucine-rich repeat, typical subtype | gi\|30679473 | gi\|30679474 | *Arabidopsis thaliana* |
| NMR4 B | At3g53600 | gi\|18409871 | gi\|15231845 | zinc finger (C2H2 type) family protein | IPR007087 Zn-finger, C2H2 type | gi\|18404421 | gi\|15228134 | *Arabidopsis thaliana* |
| | | | | | | gi\|2346973 | gi\|2346974 | *Petunia* x *hybrida* |
| | | | | | | gi\|1786133 | gi\|1786134 | *Petunia* x *hybrida* |
| NMR4 C | At3g53610 | gi\|42570491 | gi\|30693873 | Ras-related GTP-binding protein, putative | IPR001806 Ras GTPase | gi:30693869 | gi:15231847 | *Arabidopsis thaliana* |
| | | | | | IPR003577 Ras small GTPase, Ras type | gi\|42568660 | gi\|15238542 | *Arabidopsis thaliana* |
| | | | | | IPR003578 Ras small GTPase, Rho type | gi\|871509 | gi\|871510 | *Pisum sativum* |
| | | | | | IPR002041 GTP-binding nuclear protein Ran IPR006689 | gi\|2808637 | gi\|2808638 | *Daucus carota* |

TABLE 3-continued

Analysis of *Arabidopsis* NMR Sequences identified in a forward genetic screen

| 1. Gene alias | 2. TAIR | 3. Nucleic Acid seq. GI# | 4. Polypeptide seq. GI# | 5. Biochemical function/protein name | 6. Conserved protein domain | 7. Orthologous Genes: Nucleic Acid/Polypeptide seq. GI# | | |
|---|---|---|---|---|---|---|---|---|
| | | | | | | Nucleic Acid GI# | Polypeptide GI# | Species |
| NMR4 C | At3g53610 | gi:30693869 | gi:15231847 | Ras-related GTP-binding protein, putative | ARF/SAR superfamily IPR002917 GTP-binding protein, HSR1-related IPR001806 Ras GTPase | gi\|42570491 | gi\|30693873 | *Arabidopsis thaliana* |
| | | | | | IPR003577 Ras small GTPase, Ras type | gi\|42568660 | gi\|15238542 | *Arabidopsis thaliana* |
| | | | | | IPR003578 Ras small GTPase, Rho type | gi\|871509 | gi\|871510 | *Pisum sativum* |
| | | | | | IPR002041 GTP-binding nuclear protein Ran IPR006689 ARF/SAR superfamily IPR002917 GTP-binding protein, HSR1-related | gi\|2808637 | gi\|2808638 | *Daucus carota* |
| NMR4 D | At3g53620 | gi\|18409875 | gi\|15231849 | inorganic pyrophosphatase, putative [soluble]/ pyrophosphate phospho- | IPR008162 Inorganic pyrophosphatase | gi\|47775655 | gi\|47775656 | *Arachis hypogaea* |
| | | | | | | gi\|50931108 | gi\|50931109 | *Oryza sativa* (*japonica* cultivar-group) |
| | | | | | | gi\|6752883 | gi\|6752884 | *Malus x domestica* |
| NMR4 E | At3g53630 | gi\|42565899 | gi\|22331772 | expressed protein | | gi\|18415152 | gi\|15233979 | *Arabidopsis thaliana* |
| | | | | | | gi\|18405500 | gi\|15222761 | *Arabidopsis thaliana* |
| NMR4 F | At3g53640 | gi\|18409886 | gi\|15231853 | protein kinase family protein | IPR000719 Protein kinase domain | gi\|42562039 | gi\|42562040 | *Arabidopsis thaliana* |
| | | | | | IPR002290 Seine/threonine protein kinase | gi\|30688047 | gi\|22331335 | *Arabidopsis thaliana* |
| | | | | | | gi\|50918210 | gi\|50918211 | *Oryza sativa* (*japonica* cultivar-group) |
| NMR4 G | At3g53650 | gi\|18409888 | gi\|15231854 | histone H2B, putative | IPR007125 Histone core | gi\|18413963 | gi\|15241858 | *Arabidopsis thaliana* |
| | | | | | IPR000558 Histone H2B | gi\|30687153 | gi\|15224292 | *Arabidopsis thaliana* |
| | | | | | | gi\|2558961 | gi\|2558962 | *Gossypium hirsutum* |
| NMR5 A | At1g09930 | gi\|18391089 | gi\|15218331 | oligopeptide transporter OPT family protein | IPR004813 Oligopeptide transporter OPT superfamily | gi\|30698013 | gi\|15237689 | *Arabidopsis thaliana* |
| | | | | | IPR004648 Tetrapeptide transporter, OPT1/isp4 | gi\|34912939 | gi\|34912940 | *Oryza sativa* (*japonica* cultivar-group) |
| | | | | | | gi\|50911736 | gi\|50911737 | *Oryza sativa* (*japonica* cultivar-group) |
| NMR5 B | At1g09932 | gi\|30681449 | gi\|30681450 | phosphoglycerate/ bisphosphoglycerate mutase-related | IPR001345 Phosphoglycerate/ bisphosphoglycerate mutase | gi\|21700764 | gi\|21700765 | *Glycine max* |
| | | | | | | gi\|42569096 | gi\|15227803 | *Arabidopsis thaliana* |
| | | | | | | gi\|21700766 | gi\|21700767 | *Glycine max* |
| NMR5 C | At1g09935 | gi\|42570079 | gi\|42570080 | phosphoglycerate/ bisphosphoglycerate mutase family | IPR001345 Phosphoglycerate/ bisphosphoglycerate | gi\|21700764 | gi\|21700765 | *Glycine max* |

TABLE 3-continued

Analysis of *Arabidopsis* NMR Sequences identified in a forward genetic screen

| 1. Gene alias | 2. TAIR | 3. Nucleic Acid seq. GI# | 4. Polypeptide seq. GI# | 5. Biochemical function/protein name | 6. Conserved protein domain | 7. Orthologous Genes: Nucleic Acid/Polypeptide seq. GI# | | |
|---|---|---|---|---|---|---|---|---|
| | | | | | | Nucleic Acid GI# | Polypeptide GI# | Species |
| | | | | protein | mutase | gi\|21700766 | gi\|21700767 | *Glycine max* |
| | | | | | | gi\|50921188 | gi\|50921189 | *Oryza sativa (japonica cultivar-group)* |
| NMR5 D | At1g09940 | gi\|30681461 | gi\|15218333 | glutamyl-tRNA reductase 2/ GluTR (HEMA2) | IPR000343 Glutamyl-tRNA reductase | gi\|30696246 | gi\|15217924 | *Arabidopsis thaliana* |
| | | | | | IPR006151 Shikimate/quinate 5-dehydrogenase | gi\|4324494 | gi\|4324495 | *Glycine max* |
| | | | | | PF00745 Glutamyl-tRNAGlu reductase, dimerisation domain IPR004455 NADP oxidoreductase, coenzyme F420-dependent | gi\|1694925 | gi\|1694926 | *Cucumis sativus* |
| NMR5 E | At1g09950 | gi\|30681468 | gi\|15218335 | transcription factor-related | | gi\|30696249 | gi\|18406255 | *Arabidopsis thaliana* |
| | | | | | | gi\|49333382 | gi\|49333398 | *Gossypium hirsutum* |
| | | | | | | gi\|42566935 | gi\|30684489 | *Arabidopsis thaliana* |
| NMR5 F | At1g09960 | gi\|30681472 | gi\|15218362 | sucrose transporter/sucrose-proton symporter (SUT4) | IPR011701 Major facilitator superfamily MFS_1 | gi\|49609487 | gi\|49609488 | *Datisca glomerata* |
| | | | | | IPR005989 Sucrose/H+ symporter | gi\|52078040 | gi\|52078041 | *Ricinus communis* |
| | | | | | IPR011010 DNA breaking-rejoining enzyme, catalytic core | gi\|38327322 | gi\|38327323 | *Malus x domestica* |

Example 7

Identification of *Arabidopsis* Nematode Resistance Genes Using a "Reverse Genetics" Screen A "reverse genetics" screen was used as to identify *Arabidopsis* nematode resistance (NMR) genes. In this approach, *Arabidopsis* genes were considered candidate nematode resistance genes. To determine if mis-expression of these genes caused a nematode resistance phenotype, ACTTAG lines with the predicted CaMV 35S enhancer elements within 9 kbp ("activation space") of the translational initiation codons of these genes were identified from the 38,090 ACT-TAG lines with an FST placement described in Example 1. ACTTAG lines with inserts near the candidate genes were evaluated for a nematode (*Meloidogine javanica*) resistance phenotype as described in Example 2. ACTTAG lines containing ACTTAG inserts within the "activation space" of eleven candidate genes were determined to be resistant to nematodes. These genes are listed in Table 4.

The results of PFAM (Bateman et al., 1999, *Nucleic Acids Res.* 27:260-262), and/or INTERPRO (Mulder et al., 2003 *Nucleic Acids Res.* 31, 315-318; Mulder et al., 2005 *Nucleic Acids Res.* 33:D201-D205) analyses are shown in Table 4.

TABLE 4

Analysis of *Arabidopsis* NMR Sequences identified in a reverse genetic screen

| 1. Gene alias | 2. TAIR | 3. Nucleic Acid seq. GI# | 4. Polypeptide seq. GI# | 5. Biochemical function/protein name | 6. Conserved protein domain | 7. Orthologous Genes: Nucleic Acid/Polypeptide seq. GI# | | |
|---|---|---|---|---|---|---|---|---|
| | | | | | | Nucleic Acid GI# | Polypeptide GI# | Species |
| NMR1001 | At1g75250 | gi\|18410812 | gi\|15222161 | myb family transcription factor | IPR001005 Myb, DNA-binding domain | gi\|30686408 | gi\|30686409 | *Arabidopsis thaliana* |
| | | | | | | gi\|42569222 | gi\|15226604 | *Arabidopsis thaliana* |
| | | | | | | gi\|18420407 | gi\|15234999 | *Arabidopsis thaliana* |

TABLE 4-continued

Analysis of *Arabidopsis* NMR Sequences identified in a reverse genetic screen

| 1. Gene alias | 2. TAIR | 3. Nucleic Acid seq. GI# | 4. Polypeptide seq. GI# | 5. Biochemical function/protein name | 6. Conserved protein domain | 7. Orthologous Genes: Nucleic Acid/Polypeptide seq. GI# | | |
|---|---|---|---|---|---|---|---|---|
| | | | | | | Nucleic Acid GI# | Polypeptide GI# | Species |
| NMR1002 | At1g07930 | gi\|30680419 | gi\|18390829 | elongation factor 1-alpha/EF-1-alpha | IPR000795 Protein synthesis factor, GTP-binding | gi\|30680422 | gi\|18390831 | *Arabidopsis thaliana* |
| | | | | | IPR004160 Elongation factor Tu, C-terminal | gi\|927382 | gi\|1864017 | *Nicotiana tabacum* |
| | | | | | IPR004161 Elongation factor Tu, domain 2 | gi\|439576 | gi\|439577 | *Nicotiana tabacum* |
| | | | | | IPR002917 GTP-binding protein, HSR1-related | | | |
| | | | | | IPR004539 Translation elongation factor EF-1, alpha subunit | | | |
| | | | | | IPR004535 Translation elongation factor, selenocysteine-specific | | | |
| | | | | | IPR004541 Translation elongation factor Tu | | | |
| | | | | | IPR005225 Small GTP-binding protein domain | | | |
| | | | | | IPR006297 GTP-binding protein LepA | | | |
| NMR1003 | At1g17880 | gi\|30685575 | gi\|15220876 | nascent polypeptide-associated complex (NAC) domain-containing protein | IPR002715 Nascent polypeptide-associated complex NAC | gi\|18410304 | gi\|15219413 | *Arabidopsis thaliana* |
| | | | | | | gi\|33945881 | gi\|33945882 | *Lotus corniculatus* var. *japonicus* |
| | | | | | | gi\|49616928 | gi\|49616929 | *Musa acuminata* |
| NMR1004 | At1g15270 | gi\|30684274 | gi\|18394220 | expressed protein | | gi\|53748432 | gi\|53748433 | *Plantago major* |
| | | | | | | gi\|52077006 | gi\|52077016 | *Oryza sativa* (*japonica* cultivar-group) |
| | | | | | | gi\|18400993 | gi\|18400994 | *Arabidopsis thaliana* |
| NMR1005 | At2g37220 | gi\|30687074 | gi\|15228102 | 29 kDa ribonucleoprotein, chloroplast, putative/RNA-binding protein | IPR000504 RNA-binding region RNP-1 (RNA recognition motif) | gi\|30693820 | gi\|15231817 | *Arabidopsis thaliana* |
| | | | | | | gi\|30693823 | gi\|30693824 | *Arabidopsis thaliana* |
| | | | | | | gi\|19753 | gi\|19754 | *Nicotiana sylvestris* |
| NMR1006 | At2g28190 | gi\|30683800 | gi\|18401659 | superoxide dismutase [Cu—Zn], chloroplast (SODCP)/copper/zinc superoxide dismutase (CSD2) | IPR001424 Copper/Zinc superoxide dismutase | gi\|50831037 | gi\|50831038 | *Helianthus annuus* |
| | | | | | | gi\|1944325 | gi\|1944326 | *Solidago canadensis* var. *scabra* |
| | | | | | | gi\|50948526 | gi\|50948527 | *Oryza sativa* (*japonica* cultivar-group) |
| NMR1007 | At5g58330 | gi\|42573723 | gi\|42573724 | malate dehydrogenase [NADP], chloroplast, putative | | gi\|42568623 | gi\|30697051 | *Arabidopsis thaliana* |
| | | | | | | gi\|42570606 | gi\|30697049 | *Arabidopsis thaliana* |
| | | | | | | gi\|2827075 | gi\|2827076 | *Medicago sativa* |

TABLE 4-continued

Analysis of *Arabidopsis* NMR Sequences identified in a reverse genetic screen

| 1. Gene alias | 2. TAIR | 3. Nucleic Acid seq. GI# | 4. Polypeptide seq. GI# | 5. Biochemical function/protein name | 6. Conserved protein domain | 7. Orthologous Genes: Nucleic Acid/Polypeptide seq. GI# | | |
|---|---|---|---|---|---|---|---|---|
| | | | | | | Nucleic Acid GI# | Polypeptide GI# | Species |
| NMR1007 | At5g58330 | gi\|42568623 | gi\|30697051 | malate dehydrogenase [NADP], chloroplast, putative | IPR001252 Malate dehydrogenase, active site | gi\|42570606 | gi\|30697049 | *Arabidopsis thaliana* |
| | | | | | IPR001236 Lactate/malate dehydrogenase | gi\|2827075 | gi\|2827076 | *Medicago sativa* |
| | | | | | | gi\|397474 | gi\|397475 | *Pisum sativum* |
| NMR1007 | At5g58330 | gi\|42570606 | gi\|30697049 | malate dehydrogenase [NADP], chloroplast, putative | IPR001252 Malate dehydrogenase, active site | gi\|42568623 | gi\|30697051 | *Arabidopsis thaliana* |
| | | | | | IPR001236 Lactate/malate dehydrogenase | gi\|2827075 | gi\|2827076 | *Medicago sativa* |
| | | | | | | gi\|397474 | gi\|397475 | *Pisum sativum* |
| NMR1008 | At4g10340 | gi\|42566395 | gi\|15235029 | chlorophyll A-B binding protein CP26, chloroplast/light-harvesting complex II protein 5/LHCIIc (LHCB5) | IPR001344 Chlorophyll A-B binding protein | gi\|1644288 | gi\|1644289 | *Brassica juncea* |
| | | | | | | gi\|19183 | gi\|19184 | *Lycopersicon esculentum* |
| | | | | | | gi:42794111 | gi:62733869 | *Oryza sativa (japonica cultivar-group)* |
| NMR1009 | At4g13940 | gi\|30682653 | gi\|15236376 | adenosylhomocysteinase/ S-adenosyl-L-homocysteine hydrolase/ AdoHcyase (SAHH) | IPR000043 S-adenosyl-L-homocysteine hydrolase | gi\|30687216 | gi\|15229522 | *Arabidopsis thaliana* |
| | | | | | IPR006140 D-isomer specific 2-hydroxyacid dehydrogenase, NAD-binding | gi\|441216 | gi\|441217 | *Nicotiana sylvestris* |
| NMR1010 | At3g57870 | gi\|18410828 | gi\|15230881 | ubiquitin-conjugating enzyme, putative | IPR003148 TrkA-N IPR000608 Ubiquitin-conjugating enzyme, E2 | gi\|5917802 gi\|50916365 | gi\|5917803 gi\|50916366 | *Lupinus luteus* *Oryza sativa (japonica cultivar-group)* |
| | | | | | | gi\|37719048 | gi\|37719049 | *Nicotiana benthamiana* |
| | | | | | | gi\|20975733 | gi\|20975734 | *Populus euramericana* |
| NMR1011 | At5g54680 | gi\|30696503 | gi\|15239706 | basic helix-loop-helix (bHLH) family protein | IPR001092 Basic helix-loop-helix dimerisation region bHLH | gi\|30694888 | gi\|15223710 | *Arabidopsis thaliana* |
| | | | | | | gi\|50938164 | gi\|50938165 | *Oryza sativa (japonica cultivar-group)* |
| | | | | | | gi\|29367408 | gi\|29367409 | *Oryza sativa (japonica cultivar-group)* |

Example 8

Recapitulation of the Nematode Resistant Phenotype

Genes identified in the forward and reverse genetic screens were tested to identify whether direct over-expression can confer resistance to nematodes. To do this the genes listed in column 2 of Tables 3 and 4 were cloned into a plant transformation vector behind the constitutive CsVMV promoter and transformed into *Arabidopsis* plants using the floral dip method. The plant transformation vector contains a gene encoding a selectable marker driven by the RE4 promoter, to provide resistance to a cytotoxic agent, and serve as a selectable marker. Seed from the transformed plants were plated on agar medium containing the cytotoxic agent. After 10 days, transgenic plants were identified as healthy green plants and transplanted to soil. Non-transgenic control plants were germinated on agar medium, allowed to grow for 10 days and then transplanted to soil. T2 seed was collected from 20 primary transformants containing each construct.

T2 plants were tested for resistance to nematodes in replicated experiments. In each experiment, approximately 13 T2 seeds from a transgenic event were planted in soil in a 10 row tray. Each tray contained 8 rows seeded with 8 transgenic lines (1 event per row) and 2 rows seeded with wild-type Col-0 seeds; 1 of the rows containing Col-0 will be inoculated and serve as the negative control, the other will not be inoculated and serve as the positive control. The seeds were stratified for 2 days at 4° C. and grown in a growth chamber at 25° C. with 60-70% relative humidity on a short-day light cycle of 10 hours light and 14 hours dark for 8 days. The soil around each transgenic seedling and the Col-0 plants serving as the negative control was inoculated with 5000 eggs of the nematode *Meloidogine javanica* and the plants were allowed to grow for 40-50 more days. At this time the plants were removed from the soil, the root system was washed and the number of root knots per plant is recorded. A scoring system was developed to compare the number of root knots on each plant. Plants with 0 to 5 root knots were given a score of 1, plants with 6 to 10 root knots were given a score of 2, plants with 11-15 root knots were given a score of 3, plants with 16 to 20 root knots were given a score of 4 and plants with greater than 20 root knots were given a score of 5. In general, a plant was rated as resistant if it had fewer than 20 root knots. Each resistant plant (having less than 20 knots) was scored for number of knots on its root system. The genes in Table 5 showed positive recapitulation results.

TABLE 5

| TAIR ID | Alias | Clone name |
|---------|-------|------------|
| At1g18350 | NMR3-A | pNT-4581 |
| At3g53620 | NMR4-D | pNT-4590 |
| At1g09960 | NMR5-F | pNT-4599 |
| At1g07930 | NMR1002 | pNT-4942 |
| At1g15270 | NMR1004 | pNT-4944 |
| At2g37220 | NMR1005 | pNT-4945 |
| At4g10340 | NMR1008 | pNT-4948 |
| At4g13940 | NMR1009 | pNT-4949 |

Example 9

Nematode Resistance is Conferred by Over-Expression of At1g18350

The effect of over-expression of At1g18350 (NMR3-A) on nematode resistance was tested by growing T2 plants containing the CsVMV promoter driving expression of At1g18350 from 20 independent transformation events as described above. Each construct was tested in 4 replicated experiments and the knots on the roots of each plant were counted. Each plant was given a score for the number of root knots as described above. For five of the transformation events, the transgenic plants scored significantly different than the inoculated wild-type control plants indicating that they had significantly fewer root knots than the transgenic plants as determined by a two-way ANOVA test ($p \leq 0.05$) and indicating that they are resistant to nematode infection. Table 6 shows the event number, the ANOVA p-value, the average score of the transgenic plants (sample) and the average score of the control plants.

TABLE 6

| Gene | Event | ANOVA p-value | Sample | Control |
|------|-------|---------------|--------|---------|
| NMR3-A | 4581-04 | 0.000 | 4.33 | 4.89 |
| NMR3-A | 4581-13 | 0.007 | 4.70 | 4.98 |
| NMR3-A | 4581-14 | 0.017 | 4.78 | 4.98 |
| NMR3-A | 4581-15 | 0.005 | 4.66 | 5.00 |
| NMR3-A | 4581-17 | 0.000 | 4.55 | 4.98 |

Example 10

Nematode Resistance is Conferred by Over-Expression of At3g53620

The effect of over-expression of At3g53620 (NMR4-D) on nematode resistance was tested by growing T2 plants containing the CsVMV promoter driving expression of At3g53620 from 20 independent transformation events as described above. Each construct was tested in 4 replicated experiments and the knots on the roots of each plant were counted. Each plant was given a score for the number of root knots as described above. For seven of the transformation events, the transgenic plants scored significantly different than the inoculated wild-type control plants indicating that they had significantly fewer root knots than the transgenic plants as determined by a two-way ANOVA test ($p \leq 0.05$) and indicating that they are resistant to nematode infection. Table 7 shows the event number, the ANOVA p-value, the average score of the transgenic plants (sample) and the average score of the control plants.

TABLE 7

| Gene | Event | ANOVA P-value | Sample | Control |
|------|-------|---------------|--------|---------|
| NMR4-D | 4590-1 | 0.0183 | 4.90 | 5.00 |
| NMR4-D | 4590-12 | 0.0001 | 4.68 | 5.00 |
| NMR4-D | 4590-20 | 0.0127 | 4.84 | 5.00 |
| NMR4-D | 4590-22 | 0.0256 | 4.79 | 5.00 |
| NMR4-D | 4590-23 | 0.0128 | 4.79 | 5.00 |
| NMR4-D | 4590-8 | 0.0234 | 4.93 | 5.00 |
| NMR4-D | 4590-9 | 0.0419 | 4.94 | 5.00 |

Example 11

Nematode Resistance is Conferred by Over-Expression of At1g09960

The effect of over-expression of At1g09960 (NM5-F) on nematode resistance was tested by growing T2 plants containing the CsVMV promoter driving expression of At1g09960 from 20 independent transformation events as described above. Each construct was tested in 4 replicated experiments and the knots on the roots of each plant were counted. Each plant was given a score for the number of root knots as described above. For eleven of the transformation events, the transgenic plants scored significantly different than the inoculated wild-type control plants indicating that they had significantly fewer root knots than the transgenic plants as determined by a two-way ANOVA test ($p \leq 0.05$) and indicating that they are resistant to nematode infection. Table 8 shows the event number, the ANOVA p-value, the average score of the transgenic plants (sample) and the average score of the control plants.

TABLE 8

| Gene | Event | ANOVA P-value | Sample | Control |
|------|-------|---------------|--------|---------|
| NMR5-F | 4599-07 | <.0001 | 3.85 | 5.00 |
| NMR5-F | 4599-08 | <.0001 | 3.67 | 4.99 |
| NMR5-F | 4599-09 | <.0001 | 3.79 | 4.99 |
| NMR5-F | 4599-10 | <.0001 | 3.70 | 5.00 |
| NMR5-F | 4599-11 | <.0001 | 3.96 | 5.00 |
| NMR5-F | 4599-12 | <.0001 | 3.22 | 5.00 |
| NMR5-F | 4599-15 | 0.001 | 3.74 | 4.50 |

TABLE 8-continued

| Gene | Event | ANOVA P-value | Sample | Control |
|---|---|---|---|---|
| NMR5-F | 4599-16 | 0.001 | 3.60 | 4.50 |
| NMR5-F | 4599-17 | 0.001 | 3.73 | 4.50 |
| NMR5-F | 4599-18 | <.0001 | 3.13 | 4.49 |
| NMR5-F | 4599-20 | 0.005 | 3.83 | 4.50 |

Example 12

Nematode Resistance is Conferred by Over-Expression of At1g07930

The effect of over-expression of At1g07930 (NMR1002) on nematode resistance was tested by growing T2 plants containing the CsVMV promoter driving expression of At1g07930 from 20 independent transformation events as described above. Each construct was tested in 4 replicated experiments and the knots on the roots of each plant were counted. Each plant was given a score for the number of root knots as described above. For six of the transformation events, the transgenic plants scored significantly different than the inoculated wild-type control plants indicating that they had significantly fewer root knots than the transgenic plants as determined by a two-way ANOVA test ($p \leq 0.05$) and indicating that they are resistant to nematode infection. Table 9 shows the event number, the ANOVA p-value, the average score of the transgenic plants (sample) and the average score of the control plants.

TABLE 9

| Gene | Event | ANOVA P-value | Sample | Control |
|---|---|---|---|---|
| NMR1002 | 4942-05 | 0.034 | 4.68 | 5.00 |
| NMR1002 | 4942-06 | 0.000 | 4.37 | 4.99 |
| NMR1002 | 4942-07 | 0.008 | 4.60 | 5.00 |
| NMR1002 | 4942-09 | 0.002 | 4.30 | 4.96 |
| NMR1002 | 4942-10 | 0.005 | 4.59 | 4.99 |
| NMR1002 | 4942-12 | 0.034 | 4.77 | 5.00 |

Example 13

Nematode Resistance is Conferred by Over-Expression of At1g15270

The effect of over-expression of At1g15270 (NMR1004) on nematode resistance was tested by growing T2 plants containing the CsVMV promoter driving expression of At1g15270 from 20 independent transformation events as described above. Each construct was tested in 4 replicated experiments and the knots on the roots of each plant were counted. Each plant was given a score for the number of root knots as described above. For ten of the transformation events, the transgenic plants scored significantly different than the inoculated wild-type control plants indicating that they had significantly fewer root knots than the transgenic plants as determined by a two-way ANOVA test ($p \leq 0.05$) and indicating that they are resistant to nematode infection. Table 10 shows the event number, the ANOVA p-value, the average score of the transgenic plants (sample) and the average score of the control plants.

TABLE 10

| Gene | Event | ANOVA P-value | Sample | Control |
|---|---|---|---|---|
| NMR1004 | 4944-03 | 0.020 | 4.58 | 4.99 |
| NMR1004 | 4944-04 | 0.002 | 4.42 | 4.95 |
| NMR1004 | 4944-13 | 0.001 | 4.33 | 5.00 |
| NMR1004 | 4944-14 | 0.000 | 4.16 | 5.00 |
| NMR1004 | 4944-15 | <.0001 | 4.03 | 4.99 |
| NMR1004 | 4944-16 | 0.004 | 4.49 | 5.00 |
| NMR1004 | 4944-17 | <.0001 | 4.13 | 5.02 |
| NMR1004 | 4944-18 | <.0001 | 4.33 | 5.01 |
| NMR1004 | 4944-19 | 0.000 | 4.37 | 5.01 |
| NMR1004 | 4944-20 | <.0001 | 4.27 | 5.01 |

Example 14

Nematode Resistance is Conferred by Over-Expression of At2g37220

The effect of over-expression of At2g37220 (NMR1005) on nematode resistance was tested by growing T2 plants containing the CsVMV promoter driving expression of At2g37220 from 20 independent transformation events as described above. Each construct was tested in 4 replicated experiments and the knots on the roots of each plant were counted. Each plant was given a score for the number of root knots as described above. For six of the transformation events, the transgenic plants scored significantly different than the inoculated wild-type control plants indicating that they had significantly fewer root knots than the transgenic plants as determined by a two-way ANOVA test ($p \leq 0.05$) and indicating that they are resistant to nematode infection. Table 11 shows the event number, the ANOVA p-value, the average score of the transgenic plants (sample) and the average score of the control plants.

TABLE 11

| Gene | Event | ANOVA P-value | Sample | Control |
|---|---|---|---|---|
| NMR1005 | 4945-01 | 0.002 | 4.63 | 5.00 |
| NMR1005 | 4945-02 | 0.001 | 4.56 | 5.00 |
| NMR1005 | 4945-05 | 0.003 | 4.68 | 5.00 |
| NMR1005 | 4945-06 | <.0001 | 4.46 | 5.00 |
| NMR1005 | 4945-07 | 0.007 | 4.70 | 5.00 |
| NMR1005 | 4945-08 | 0.000 | 4.46 | 5.00 |

Example 15

Nematode Resistance is Conferred by Over-Expression of At4g10340

The effect of over-expression of At4g10340 (NMR1008) on nematode resistance was tested by growing T2 plants containing the CsVMV promoter driving expression of At4g10340 from 20 independent transformation events as described above. Each construct was tested in 4 replicated experiments and the knots on the roots of each plant were counted. Each plant was given a score for the number of root knots as described above. For five of the transformation events, the transgenic plants scored significantly different than the inoculated wild-type control plants indicating that they had significantly fewer root knots than the transgenic plants as determined by a two-way ANOVA test ($p \leq 0.05$) and indicating that they are resistant to nematode infection. Table 12 shows the event number, the ANOVA p-value, the average score of the transgenic plants (sample) and the average score of the control plants.

TABLE 12

| Gene | Event | Line | ANOVA P-value | Sample | Control |
|---|---|---|---|---|---|
| NMR1008 | 4948-01 | 4948-01 | 0.046 | 4.55 | 4.88 |
| NMR1008 | 4948-02 | 4948-02 | 0.033 | 4.32 | 4.82 |
| NMR1008 | 4948-05 | 4948-05 | <.0001 | 3.80 | 4.85 |
| NMR1008 | 4948-07 | 4948-07 | 0.217 | 4.59 | 4.82 |
| NMR1008 | 4948-08 | 4948-08 | 0.002 | 4.14 | 4.85 |

Example 16

Nematode Resistance is Conferred by Over-Expression of At4g13940

The effect of over-expression of At4g13940 (NMR1009) on nematode resistance was tested by growing T2 plants containing the CsVMV promoter driving expression of At4g13940 from 20 independent transformation events as described above. Each construct was tested in 4 replicated experiments and the knots on the roots of each plant were counted. Each plant was given a score for the number of root knots as described above. For seven of the transformation events, the transgenic plants scored significantly different than the inoculated wild-type control plants indicating that they had significantly fewer root knots than the transgenic plants as determined by a two-way ANOVA test ($p \leq 0.05$) and indicating that they are resistant to nematode infection. Table 13 shows the event number, the ANOVA p-value, the average score of the transgenic plants (sample) and the average score of the control plants.

TABLE 13

| Gene | Event | ANOVA P-value | Sample | Control |
|---|---|---|---|---|
| NMR1009 | 4949-09 | 0.020 | 4.79 | 5.00 |
| NMR1009 | 4949-12 | 0.027 | 4.79 | 4.99 |
| NMR1009 | 4949-13 | 0.029 | 4.84 | 5.00 |
| NMR1009 | 4949-14 | 0.002 | 4.65 | 5.00 |
| NMR1009 | 4949-15 | 0.001 | 4.64 | 5.00 |
| NMR1009 | 4949-16 | 0.001 | 4.66 | 5.00 |
| NMR1009 | 4949-18 | 0.000 | 4.57 | 5.00 |

It is claimed:

1. A transgenic plant having stably incorporated into its genome a DNA construct comprising a nucleotide sequence that encodes a protein having nematode resistance activity, wherein said nucleotide sequence is selected from the group consisting of:
   a) the nucleotide sequence set forth as SEQ ID NO: 61;
   b) a nucleotide sequence having at least 90% sequence identity to the nucleotide sequence set forth as SEQ ID NO: 61;
   c) a nucleotide sequence encoding a polypeptide comprising the amino acid sequence set forth as SEQ ID NO: 62; and,
   d) a nucleotide sequence encoding a polypeptide having at least 90% sequence identity to the amino acid sequence set forth as SEQ ID NO: 62;
   wherein the nucleotide sequence is operably linked to a promoter that drives expression of a coding sequence in a plant cell,
   and wherein the transgenic plant has increased resistance to at least one nematode relative to a plant of the same species that does not comprise the nucleotide sequence.

2. The plant of claim 1, wherein the promoter is a constitutive promoter.

3. The plant of claim 1, wherein the plant is selected from the group consisting of rapeseed, soy, corn, sunflower, cotton, cocoa, safflower, oil palm, coconut palm, flax, castor and peanut, tomato, carrot, lettuce, bean, asparagus, cauliflower, pepper, beetroot, cabbage, eggplant, endive, leek, long cucumber, melon, pea, radish, rootstock, short cucumber, squash, watermelon, white onion, witloof, yellow onion, broccoli, brussel sprout, bunching onion, celery, mache, cucumber, fennel, gourd, pumpkin, sweet corn, and zucchini.

4. A method of producing a plant with increased nematode resistance, said method comprising:
   a) introducing into the plant or a cell thereof at least one plant transformation vector comprising a nucleotide sequence that encodes an NMR polypeptide having at least 90% sequence identity to the amino acid sequence set forth as SEQ ID NO: 62, and,
   b) growing the transformed plant or cell to produce a transgenic plant, wherein said transgenic plant exhibits increased resistance to at least one nematode relative to a plant of the same species that does not comprise the nucleotide sequence.

5. A transformed plant having increased nematode resistance obtained by the method of claim 4.

6. A transformed plant part obtained from the plant according to claim 5.

7. Transformed seed of the plant of claim 5.

* * * * *

UNITED STATES PATENT AND TRADEMARK OFFICE
CERTIFICATE OF CORRECTION

| | |
|---|---|
| PATENT NO. | : 8,222,485 B2 |
| APPLICATION NO. | : 12/304343 |
| DATED | : July 17, 2012 |
| INVENTOR(S) | : Wagner et al. |

It is certified that error appears in the above-identified patent and that said Letters Patent is hereby corrected as shown below:

In the Specification:

Column 10, line 36, "(GT#s)" should read --(GI#s)--.

Column 31, line 45, "used as to" should read --used to--.

Signed and Sealed this
Twenty-fifth Day of March, 2014

Michelle K. Lee
*Deputy Director of the United States Patent and Trademark Office*

SEQUENCE LISTING

<160> NUMBER OF SEQ ID NOS: 88

<210> SEQ ID NO 1
<211> LENGTH: 2196
<212> TYPE: DNA
<213> ORGANISM: Arabidopsis thaliana

<400> SEQUENCE: 1

```
atgtctcata tgttcctcag atgcatcggc atttcccaaa tcgcttcata tatgattgct      60
ggaatagttc tagggcctca gcttttgat gtactagaga aatcttcagg gaaactatcc     120
gtggatcctg cgttggatgg aatcgcagcg ttaagatgca tctcggtgtt tggaacacta     180
atgtttacgt ttctaatgac tgttagaacc agcaggcgag tggcgttcca tagcggaaaa     240
ttgcccgttg tgatcgggat cgtgtccttc tttgctcctc tgtttggtct cggtttccag     300
aatttttttt ctgacaacat cgaccctcac tacatgcctc taactaaagc cctaggtgag     360
cgcactgcga ttgtcataac tcaatcttcg atacttttgc cttccactac atatatcttg     420
ctagagctca agatcatcaa ctccgagcta ggtcgccttg cattgtctgc atgtgtcatc     480
aacgacatct tggggatttt ttccatgata gttgcctcta tacaagcgac ctacattcat     540
gtttcacatg caacagccta tcgtgacact gtcgcggtga tcatcttttt tctcgtcgtc     600
tttcttgttt ttaagcctat ggtgcaatgg gtcatagacc gcacaccgga agacaagcca     660
gtggaggata tgtacattca tgccgtgatt attaccgcat tggcttccgc tgcttatttt     720
gtgtttttca acatgaaata tattttagga ccattaatga ttggcatcat cataccagag     780
ggtccaccat taggatcggc tctagaggct aagtttgaga ggctcacaat gaacgtgttc     840
ttaccaatct caatcacatt cagcgcgatg agatgtgatg gagcaaggat ccttagccag     900
ttcaatgaca tcttcttcaa catcttccta acatttctta tacttgtcat aaaactggtc     960
gcatgccttg caccttgctt gtactacaag ttacctctca gtgaatcctt ggctgtttcc    1020
ttcatcttga gctacaaaag ttttgctgat tttgttctct atgaagctgt attagacgac    1080
acgtacatat cgcaagccac ttactcgttc ttaatcttat attcgctact aaatgccggg    1140
```

```
attgtcccta ctgtcttaag gaggatgtac gatccaagaa gaaagtacgt taattaccag    1200
aaaagggaca tattgcatct agaacgaaac tcagatcttc gaattctaac ttgtttgcac    1260
aaaccagaaa acgtctcaga gaccatagca ttcctacaat tgttgtcctc accgaaccta    1320
gacttcccta tcgcggttac agttctccac cttgtgaagc tcgttggtca gataaaccct    1380
atcatagtct cacacgacaa gaaattgaaa cggcttaaca agactcata catccatacc     1440 gcaaaccttg cctttagaca attcgtgtta gaaagcttag agtctgtaac cgtgacaacg    1500
ttcactgcgt tctcgcatga aaacttgatg cacgaagaca tttgtacact tgcacttgac    1560
aaaacaacat cgatgattgt cgtcccatcg gggaggaaat ggactgtaga tgggttattc    1620
gagtctgaca acactgctat aagacatcta aaccagtcgt tactcgatcg tgcgccttgt    1680
tctatcggca tactagtaga ccgtggacaa ttctcgcgaa aaagtattgt aacgagcaaa    1740
aaaaggtaca tcattgatgt tggtgtgctc ttcattggag gcaaagacga tagggaagca    1800
ctatcattgg tgaagaggat gaaaataac ccgaggatcc gtgtaaccgt gatccgactc      1860
gtcttcgacc atgaaataga gtcagattgg gattatattc ttgataacga aggcttaaag    1920
gatttgaaga gtactgaaga caacaaagat attgattata tagagaggat tgtgactagt    1980
agtgttgagg tagtcaaagc tgtccaattg cttgcagaag agtacgatct aatggtggtc    2040
gggagagatc atgatatgac atcacaagac ttatcaggac taatgaaatg ggtcgaacta    2100
ccagagttag gtgtcatcgg ggatttgctg gcggctagag atctaagctc taaggtttcg    2160
gttttagtag ttcaacaaca acaacaacga acgtga                              2196

<210> SEQ ID NO 2
<211> LENGTH: 731
<212> TYPE: PRT
<213> ORGANISM: Arabidopsis thaliana

<400> SEQUENCE: 2

Met Ser His Met Phe Leu Arg Cys Ile Gly Ile Ser Gln Ile Ala Ser
1               5                   10                  15

Tyr Met Ile Ala Gly Ile Val Leu Gly Pro Gln Leu Phe Asp Val Leu
            20                  25                  30

Glu Lys Ser Ser Gly Lys Leu Ser Val Asp Pro Ala Leu Asp Gly Ile
        35                  40                  45

Ala Ala Leu Arg Cys Ile Ser Val Phe Gly Thr Leu Met Phe Thr Phe
    50                  55                  60

Leu Met Thr Val Arg Thr Ser Arg Arg Val Ala Phe His Ser Gly Lys
65                  70                  75                  80

Leu Pro Val Val Ile Gly Ile Val Ser Phe Phe Ala Pro Leu Phe Gly
                85                  90                  95

Leu Gly Phe Gln Asn Phe Phe Ser Asp Asn Ile Asp Pro His Tyr Met
            100                 105                 110

Pro Leu Thr Lys Ala Leu Gly Glu Arg Thr Ala Ile Val Ile Thr Gln
        115                 120                 125

Ser Ser Ile Leu Leu Pro Ser Thr Thr Tyr Ile Leu Leu Glu Leu Lys
    130                 135                 140

Ile Ile Asn Ser Glu Leu Gly Arg Leu Ala Leu Ser Ala Cys Val Ile
145                 150                 155                 160

Asn Asp Ile Leu Gly Ile Phe Ser Met Ile Val Ala Ser Ile Gln Ala
                165                 170                 175

Thr Tyr Ile His Val Ser His Ala Thr Ala Tyr Arg Asp Thr Val Ala
            180                 185                 190
```

```
Val Ile Ile Phe Phe Leu Val Val Phe Leu Val Phe Lys Pro Met Val
            195                 200                 205

Gln Trp Val Ile Asp Arg Thr Pro Glu Asp Lys Pro Val Glu Asp Met
210                 215                 220

Tyr Ile His Ala Val Ile Thr Ala Leu Ser Ala Ala Tyr Phe
225                 230                 235                 240

Val Phe Phe Asn Met Lys Tyr Ile Leu Gly Pro Leu Met Ile Gly Ile
            245                 250                 255

Ile Ile Pro Glu Gly Pro Pro Leu Gly Ser Ala Leu Glu Ala Lys Phe
            260                 265                 270

Glu Arg Leu Thr Met Asn Val Phe Leu Pro Ile Ser Ile Thr Phe Ser
            275                 280                 285

Ala Met Arg Cys Asp Gly Ala Arg Ile Leu Ser Gln Phe Asn Asp Ile
            290                 295                 300

Phe Phe Asn Ile Phe Leu Thr Phe Leu Ile Leu Val Ile Lys Leu Val
305                 310                 315                 320

Ala Cys Leu Ala Pro Cys Leu Tyr Tyr Lys Leu Pro Leu Ser Glu Ser
            325                 330                 335

Leu Ala Val Ser Phe Ile Leu Ser Tyr Lys Ser Phe Ala Asp Phe Val
            340                 345                 350

Leu Tyr Glu Ala Val Leu Asp Asp Thr Tyr Ile Ser Gln Ala Thr Tyr
            355                 360                 365

Ser Phe Leu Ile Leu Tyr Ser Leu Leu Asn Ala Gly Ile Val Pro Thr
            370                 375                 380

Val Leu Arg Arg Met Tyr Asp Pro Arg Arg Lys Tyr Val Asn Tyr Gln
385                 390                 395                 400

Lys Arg Asp Ile Leu His Leu Glu Arg Asn Ser Asp Leu Arg Ile Leu
            405                 410                 415

Thr Cys Leu His Lys Pro Glu Asn Val Ser Glu Thr Ile Ala Phe Leu
            420                 425                 430

Gln Leu Leu Ser Ser Pro Asn Leu Asp Phe Pro Ile Ala Val Thr Val
            435                 440                 445

Leu His Leu Val Lys Leu Val Gly Gln Ile Asn Pro Ile Ile Val Ser
            450                 455                 460

His Asp Lys Lys Leu Lys Arg Leu Asn Lys Asp Ser Tyr Ile His Thr
465                 470                 475                 480

Ala Asn Leu Ala Phe Arg Gln Phe Val Leu Glu Ser Leu Glu Ser Val
            485                 490                 495

Thr Val Thr Thr Phe Thr Ala Phe Ser His Glu Asn Leu Met His Glu
            500                 505                 510

Asp Ile Cys Thr Leu Ala Leu Asp Lys Thr Thr Ser Met Ile Val Val
            515                 520                 525

Pro Ser Gly Arg Lys Trp Thr Val Asp Gly Leu Phe Glu Ser Asp Asn
            530                 535                 540

Thr Ala Ile Arg His Leu Asn Gln Ser Leu Leu Asp Arg Ala Pro Cys
545                 550                 555                 560

Ser Ile Gly Ile Leu Val Asp Arg Gly Gln Phe Ser Arg Lys Ser Ile
            565                 570                 575

Val Thr Ser Lys Lys Arg Tyr Ile Ile Asp Val Gly Val Leu Phe Ile
            580                 585                 590

Gly Gly Lys Asp Asp Arg Glu Ala Leu Ser Leu Val Lys Arg Met Lys
            595                 600                 605

Asn Asn Pro Arg Ile Arg Val Thr Val Ile Arg Leu Val Phe Asp His
```

```
                610                615                620
Glu Ile Glu Ser Asp Trp Asp Tyr Ile Leu Asp Asn Glu Gly Leu Lys
625                630                635                640

Asp Leu Lys Ser Thr Glu Asp Asn Lys Asp Ile Asp Tyr Ile Glu Arg
                645                650                655

Ile Val Thr Ser Ser Val Glu Val Val Lys Ala Val Gln Leu Leu Ala
                660                665                670

Glu Glu Tyr Asp Leu Met Val Val Gly Arg Asp His Asp Met Thr Ser
                675                680                685

Gln Asp Leu Ser Gly Leu Met Glu Trp Val Glu Leu Pro Glu Leu Gly
                690                695                700

Val Ile Gly Asp Leu Leu Ala Ala Arg Asp Leu Ser Ser Lys Val Ser
705                710                715                720

Val Leu Val Val Gln Gln Gln Gln Arg Thr
                725                730

<210> SEQ ID NO 3
<211> LENGTH: 333
<212> TYPE: DNA
<213> ORGANISM: Arabidopsis thaliana

<400> SEQUENCE: 3
atggatatgc tagaggatga aatgagcctt tgcaaagtca tgatgctcta tttagcagag      60
ggacgatcgc tagagttaat agagaatata ttcagatctt ccaaaacgaa aggaagagtg     120
atatataaca ccatgatctc ggtgtatgga aaacactttg ctgagaatgc acaccagttg     180
tttctggaga tggtcaacaa cagaattcgt ctcagcggtc acaccttcaa gtatcatcta     240
gaagcatgga cgatagcctg caaaccacaa aggactcttg aattcttgca tttcatgata     300 ttgttttta taaagggtaa gaaaaagatg tag                                   333

<210> SEQ ID NO 4
<211> LENGTH: 110
<212> TYPE: PRT
<213> ORGANISM: Arabidopsis thaliana

<400> SEQUENCE: 4

Met Asp Met Leu Glu Asp Glu Met Ser Leu Cys Lys Val Met Met Leu
1               5                   10                  15

Tyr Leu Ala Glu Gly Arg Ser Leu Glu Leu Ile Glu Asn Ile Phe Arg
                20                  25                  30

Ser Ser Lys Thr Lys Gly Arg Val Ile Tyr Asn Thr Met Ile Ser Val
            35                  40                  45

Tyr Gly Lys His Phe Ala Glu Asn Ala His Gln Leu Phe Leu Glu Met
        50                  55                  60

Val Asn Asn Arg Ile Arg Leu Ser Gly His Thr Phe Lys Tyr His Leu
65                  70                  75                  80

Glu Ala Trp Thr Ile Ala Cys Lys Pro Gln Arg Thr Leu Glu Phe Leu
                85                  90                  95

His Phe Met Ile Leu Phe Phe Ile Lys Gly Lys Lys Met
                100                 105                 110

<210> SEQ ID NO 5
<211> LENGTH: 1387
<212> TYPE: DNA
<213> ORGANISM: Arabidopsis thaliana

<400> SEQUENCE: 5
```

```
agtccatgaa atttcactac ttttataact ctctctccct ccttcttctt cttccataaa    60
actcttcact aaacctaaag atctcttaag cttaattttg caagatcatg gaccaaagca   120
attctcttct tagctggact tacttctctc atggaaagac aacggaagag ctaagacaga   180
ctctcgtgta cacaacaatg gagttagaac aaacaaagct tgtggctcac gaggagctaa   240
ggaagagaga tgaacaactg atccacctag aagatgtttt aaccaaaacc ctcaaagaaa   300
gagacgaagc tctagagaaa tataatcatc tcctcttaaa taatctctta cttcaacaga   360
agcagcaaca gaatcagaat cagaaacaag aacttgtcac tcctccttta tcaggagctt   420
caagtattat tgaagacgag caagttcagc cacagcagcc gcagcttaac tcaaacaaga   480
gcttttcgtc ttcagacact gaagaaagca tcatgtcacc atcagtgatt gatccagtga   540
cgatgaacca acagattgaa gtctcaggag atgagatgtt ggctacattg ttgcctgaca   600
aaccactgcc tgaaaaggga aaactcttac aagctgttat caaggcaggt cctttgcttc   660
agacacttct cttagctggt cctctgcctc aatggcgcca cccaccgcct ccacttgaga   720
cctctgagat ccctcctgtc accattccac tacctcagtt tcagaacaat ggctgtggga   780
actccaacaa gaaagggca ttctcaatct cagatgaaac ttattcagag actaagtatc   840
agaaagttct tctccattaa ccggctactg atctttttat ccttactcaa caaaatacta   900
atatatagtc tttctaatat accaatatac agatcacttt tcagtattaa tctcacttag   960
ggtactagtg agagtgatct ttttagtcag tttgttgtag atagagcttg atttgaattt  1020
gtggagagtg aatctgatcc atttagggtt tagatctaga gagtgatggg aatgaaactc  1080
ccctggttta actcatactc gaacatgagt gttttttta ccaagtgaga gagttttgct  1140
atttgctttt cttttgttgt gcttattgat ttccttgtttt gtttcctaaa cccaattta  1200 cattcatgtt ttggctccat gaatgtaaac ttattggggt gttttgtgtt ttttttcttc  1260
ctttgtaatc caatttcacc ttggtgtaaa atactaaaaa tctaaaggaa atgtgatgtt  1320
tctgttttca ggaaatgtaa tgtatagtat gtaaagactt tgattatata tatataatat  1380
atatact                                                             1387
```

<210> SEQ ID NO 6
<211> LENGTH: 250
<212> TYPE: PRT
<213> ORGANISM: Arabidopsis thaliana

<400> SEQUENCE: 6

```
Met Asp Gln Ser Asn Ser Leu Leu Ser Trp Thr Tyr Phe Ser His Gly
1               5                   10                  15

Lys Thr Thr Glu Glu Leu Arg Gln Thr Leu Val Tyr Thr Thr Met Glu
            20                  25                  30

Leu Glu Gln Thr Lys Leu Val Ala His Glu Glu Leu Arg Lys Arg Asp
        35                  40                  45

Glu Gln Leu Ile His Leu Glu Asp Val Leu Thr Lys Thr Leu Lys Glu
    50                  55                  60

Arg Asp Glu Ala Leu Glu Lys Tyr Asn His Leu Leu Asn Asn Leu
65                  70                  75                  80

Leu Leu Gln Gln Lys Gln Gln Asn Gln Asn Gln Lys Gln Glu Leu
                85                  90                  95

Val Thr Pro Pro Leu Ser Gly Ala Ser Ser Ile Ile Glu Asp Glu Gln
            100                 105                 110

Val Gln Pro Gln Gln Pro Gln Leu Asn Ser Asn Lys Ser Phe Ser Ser
        115                 120                 125
```

```
Ser Asp Thr Glu Glu Ser Ile Met Ser Pro Ser Val Ile Asp Pro Val
    130                 135                 140

Thr Met Asn Gln Gln Ile Glu Val Ser Gly Asp Glu Met Leu Ala Thr
145                 150                 155                 160

Leu Leu Pro Asp Lys Pro Leu Pro Glu Lys Gly Lys Leu Leu Gln Ala
                165                 170                 175

Val Ile Lys Ala Gly Pro Leu Leu Gln Thr Leu Leu Leu Ala Gly Pro
            180                 185                 190

Leu Pro Gln Trp Arg His Pro Pro Pro Leu Glu Thr Ser Glu Ile
        195                 200                 205

Pro Pro Val Thr Ile Pro Leu Pro Gln Phe Gln Asn Asn Gly Cys Gly
    210                 215                 220

Asn Ser Asn Lys Lys Arg Ala Phe Ser Ile Ser Asp Glu Thr Tyr Ser
225                 230                 235                 240

Glu Thr Lys Tyr Gln Lys Val Leu Leu His
                245                 250

<210> SEQ ID NO 7
<211> LENGTH: 219
<212> TYPE: DNA
<213> ORGANISM: Arabidopsis thaliana

<400> SEQUENCE: 7
atgaccacat tggcaacggt ggtggctccg acaacggtgg tggctagctc cggcgacggc    60
ggttgctccg cgacaatgg aagctccggt gacaatggga accccaacaa tggggtggtg   120
gctccggttg gtaactccgg cggcggtggt ggtggtgatg atggcggaga cgtcggtggt   180
ggtgatgacg gcggcggcgg tggtgtgtgg ttatggtag                          219

<210> SEQ ID NO 8
<211> LENGTH: 72
<212> TYPE: PRT
<213> ORGANISM: Arabidopsis thaliana

<400> SEQUENCE: 8

Met Thr Thr Leu Ala Thr Val Val Ala Pro Thr Thr Val Val Ala Ser
1               5                   10                  15

Ser Gly Asp Gly Gly Cys Ser Gly Asp Asn Gly Ser Ser Gly Asp Asn
            20                  25                  30

Gly Asn Pro Asn Asn Gly Val Val Ala Pro Val Gly Asn Ser Gly Gly
        35                  40                  45

Gly Gly Gly Gly Asp Asp Gly Asp Val Gly Gly Asp Asp Gly
    50                  55                  60

Gly Gly Gly Gly Val Trp Leu Trp
65                  70

<210> SEQ ID NO 9
<211> LENGTH: 2634
<212> TYPE: DNA
<213> ORGANISM: Arabidopsis thaliana

<400> SEQUENCE: 9
atctaatggc catttaatcc gccagagaag aagaagaaga agaaaataga ttagggtttt    60
tcattccaga atagccctaa tccaaattcg aaatctttct tctgattttg atctttccga   120
tcatgtcatc ggtctgtgtt aacgaagcat taaccgatga cgagctgaga tgggtattgt   180
cgagactaga cagtgataaa gataaggaag tgtttggttt ggtctgcaag aggtggctaa   240
atctgcagag taccgaccgg aagaagctag cggcacgtgc tggtccacat atgctccgcc   300
```

```
gtctcgcttc taggttcact caaatcgtcg aattggattt gtctcagtca atttctaggt     360
ccttttatcc aggagttact gattctgacc tcgctgttat ctctgaggga ttcaagtttc     420
tcagagttct taatcttcac aactgtaaag gtattacaga tactggattg gcctcaattg     480
gaaggtgtct ttctttactg cagtttttgg atgtatcata ttgtagaaag ctctcagata     540
aaggattatc agctgttgca gaaggctgcc atgatctaag ggcattgcat ttagcgggtt     600
gtcgtttcat caccgatgaa tcgttgaaat cactctctga gagatgccgt gatctcgaag     660
ctctggggct acaaggctgc accaatatca ctgattcagg tcttgctgat cttgtgaagg     720
gatgcagaaa gataaaatct ttagacatta ataaatgtag caatgttgga gatgctggag     780
tttcgagcgt ggcgaaagct tgtgcatctt ccctcaagac actcaaattg ctggactgtt     840
acaaagtcgg gaacgaatct atatcgtcgc tggcgcagtt ttgcaagaat ctggaaactc     900
tgataatcgg tggatgcaga gatatctctg acgaatctat catgttactg gcagattcct     960
gtaaagacag tctcaagaac ttgaggatgg attggtgctt gaatatatct gactcttccc    1020
ttagctgcat tctcaagcag tgcaagaact tggaggctct agatattggt tgctgtgaag    1080
aggtcacaga cactgctttc cgggatttag ggagcgacga tgttttggga ttgaaggttt    1140
taaaggttag caactgcacg aagatcacag taacagggat aggcaagctt ttggacaaat    1200
gcagttccct ggagtatata gatgtaaggt ctcttccaca tgtgacagaa gtgagatgca    1260
gtgaagctgg tttggagttc ccaaaatgtt gtaaagttaa cttttcaggt agtttaaccg    1320
agccagatgt tctgctttga tcgttgctgt tgggatctcg ttacttgtct gttgggaaat    1380
tctggtaacc ctaaaccttc tgtgatctct ctatctgtct cgtgtatggg cacactcata    1440
gcttatagtt catcagtgag tcttctctca agctcttgta tatttttgtg cattaaatat    1500
ttggttgtag cggctgcttg attattcttc agttgctttg caaagtgtgt gtagttgttg    1560
ttgaacctgc ttctccttaa gagtaaaaaa aggtcagcac ttgatatttg taaactctga    1620
ttctcaatgt actgatttct taatacttga ttcatcccat tacacttctt ttgacatagt    1680
ttggtgcata aaagaactat gaattaaggt taacagatga gatcaactaa atatattcat    1740 ctcttttctcg tgtctacaat ggaaaccaaa gtgggtaaag caaaaaaaaa gaatttgtga    1800
gtttgtacaa acattctctg actgaaacag gggaaagtag aaatgaaata tttcttgttc    1860
cacctgcact aattagctcc gtcagagaaa accactgcgg tttattgctc atcattgttt    1920
agcgctttct cgagacagtt gaaagctttc tggtagctca cgaatcccat gaaccagaag    1980
tcgaagttat cgattgtgac tatttcaagg tacttttgag atggcttctt tgtgttctga    2040
ctctggttca ctccattgat cttgcacaat gggattgaga ctttgtagtg aaccctactg    2100
agaactcctt gaggagaagc aaccttgatc gatctttcac tgcaaaatgc aatcttcttt    2160
gatgagatga agaggaggcc tgcgatggga cctgctgttg tggatagata gcattggtac    2220
gccttgaaga gtttctcttg atcgcagacc ttgaagagtc gcttataaat cttctctaag    2280
cctcccattt gaaggatctt agctcccaag gatagctttc tcttgactgt ttcagttagc    2340
tttggtccta gtttgtcctg atctctagct ccgtttgtga agctatcggt tttcttcttt    2400
cgcagcatcg atttttccttt gcctgtcaaa tatgaaacct ttgaagaagt tgggatttgg    2460
tggttgttga tggaagctgg gtcaggcaag taactcatcg tatcagtctt ggctgcagga    2520
aatgcaataa cttgttggtg aactctgctc agtgtcatct tggaggattg agtagtgatc    2580
ttgattcttg attttgtgaa agagaaagag agagagagat tgtgagtgat ggtt          2634
```

<210> SEQ ID NO 10
<211> LENGTH: 405
<212> TYPE: PRT
<213> ORGANISM: Arabidopsis thaliana

<400> SEQUENCE: 10

Met Ser Ser Val Cys Val Asn Glu Ala Leu Thr Asp Asp Glu Leu Arg
1               5                   10                  15

Trp Val Leu Ser Arg Leu Asp Ser Asp Lys Asp Lys Glu Val Phe Gly
            20                  25                  30

Leu Val Cys Lys Arg Trp Leu Asn Leu Gln Ser Thr Asp Arg Lys Lys
        35                  40                  45

Leu Ala Ala Arg Ala Gly Pro His Met Leu Arg Arg Leu Ala Ser Arg
    50                  55                  60

Phe Thr Gln Ile Val Glu Leu Asp Leu Ser Gln Ser Ile Ser Arg Ser
65                  70                  75                  80

Phe Tyr Pro Gly Val Thr Asp Ser Asp Leu Ala Val Ile Ser Glu Gly
                85                  90                  95

Phe Lys Phe Leu Arg Val Leu Asn Leu His Asn Cys Lys Gly Ile Thr
            100                 105                 110

Asp Thr Gly Leu Ala Ser Ile Gly Arg Cys Leu Ser Leu Leu Gln Phe
        115                 120                 125

Leu Asp Val Ser Tyr Cys Arg Lys Leu Ser Asp Lys Gly Leu Ser Ala
    130                 135                 140

Val Ala Glu Gly Cys His Asp Leu Arg Ala Leu His Leu Ala Gly Cys
145                 150                 155                 160

Arg Phe Ile Thr Asp Glu Ser Leu Lys Ser Leu Ser Glu Arg Cys Arg
                165                 170                 175

Asp Leu Glu Ala Leu Gly Leu Gln Gly Cys Thr Asn Ile Thr Asp Ser
            180                 185                 190

Gly Leu Ala Asp Leu Val Lys Gly Cys Arg Lys Ile Lys Ser Leu Asp
        195                 200                 205

Ile Asn Lys Cys Ser Asn Val Gly Asp Ala Gly Val Ser Ser Val Ala
    210                 215                 220

Lys Ala Cys Ala Ser Ser Leu Lys Thr Leu Lys Leu Asp Cys Tyr
225                 230                 235                 240

Lys Val Gly Asn Glu Ser Ile Ser Ser Leu Ala Gln Phe Cys Lys Asn
                245                 250                 255

Leu Glu Thr Leu Ile Ile Gly Gly Cys Arg Asp Ile Ser Asp Glu Ser
            260                 265                 270

Ile Met Leu Leu Ala Asp Ser Cys Lys Asp Ser Leu Lys Asn Leu Arg
        275                 280                 285

Met Asp Trp Cys Leu Asn Ile Ser Asp Ser Ser Leu Ser Cys Ile Leu
    290                 295                 300

Lys Gln Cys Lys Asn Leu Glu Ala Leu Asp Ile Gly Cys Cys Glu Glu
305                 310                 315                 320

Val Thr Asp Thr Ala Phe Arg Asp Leu Gly Ser Asp Val Leu Gly
                325                 330                 335

Leu Lys Val Leu Lys Val Ser Asn Cys Thr Lys Ile Thr Val Thr Gly
            340                 345                 350

Ile Gly Lys Leu Leu Asp Lys Cys Ser Leu Glu Tyr Ile Asp Val
        355                 360                 365

Arg Ser Leu Pro His Val Thr Glu Val Arg Cys Ser Glu Ala Gly Leu
    370                 375                 380

Glu Phe Pro Lys Cys Cys Lys Val Asn Phe Ser Gly Ser Leu Thr Glu

Pro Asp Val Leu Leu
            405

<210> SEQ ID NO 11
<211> LENGTH: 1020
<212> TYPE: DNA
<213> ORGANISM: Arabidopsis thaliana

<400> SEQUENCE: 11

```
atgactcatc ctttaccaca aagggtctca attcagagct tcgtttcaac tgcctcttgt     60
ctctttgttt ttccctttaa ataccttccc acttacacgg tttcatcatc aaccatcact    120
cacaatctct ctctctcttt ctctttcaca aaatcaagaa tcaagatcac tactcaatcc    180
tccaagatga cactgagcag agttcaccaa caagttattg catttcctgc agccaagact    240
gatacgatga gttacttgcc tgacccagct tccatcaaca accaccaaat cccaacttct    300
tcaaaggttt catatttgac aggcaaagga aaatcgatgc tgcgaaagaa gaaaaccgat    360
agcttcacaa acggagctag agatcaggac aaactaggac aaagctaac tgaaacagtc     420
aagagaaagc tatccttggg agctaagatc cttcaaatgg gaggcttaga gaagatttat    480
aagcgactct tcaaggtctg cgatcaagag aaactcttca aggcgtacca atgctatcta    540
tccacaacag caggtcccat cgcaggcctc ctcttcatct catcaaagaa gattgcattt    600
tgcagtgaaa gatcgatcaa ggttgcttct cctcaaggag ttctcagtag ggttcactac    660
aaagtctcaa tcccattgtg caagatcaat ggagtgaacc agagtcagaa cacaaagaag    720
ccatctcaaa gtaccttga atagtcaca atcgataact tcgacttctg gttcatggga    780
ttcgtgagct accagaaagc tttcaactgt ctcgagaaag cgctaaacaa tgatgagcaa    840
taaaccgcag tggttttctc tgacggagct aattagtgca ggtggaacaa gaaatatttc    900
atttctactt tcccctgttt cagtcagaga atgtttgtac aaactcacaa attctttttt    960
tttgctttac ccactttggt ttccattgta gacacgagaa agagatgaat atatttagtt   1020
```

<210> SEQ ID NO 12
<211> LENGTH: 280
<212> TYPE: PRT
<213> ORGANISM: Arabidopsis thaliana

<400> SEQUENCE: 12

Met Thr His Pro Leu Pro Gln Arg Val Ser Ile Gln Ser Phe Val Ser
1               5                   10                  15

Thr Ala Ser Cys Leu Phe Val Phe Pro Phe Lys Tyr Leu Pro Thr Tyr
            20                  25                  30

Thr Val Ser Ser Ser Thr Ile Thr His Asn Leu Ser Leu Ser Phe Ser
        35                  40                  45

Phe Thr Lys Ser Arg Ile Lys Ile Thr Thr Gln Ser Ser Lys Met Thr
    50                  55                  60

Leu Ser Arg Val His Gln Gln Val Ile Ala Phe Pro Ala Ala Lys Thr
65                  70                  75                  80

Asp Thr Met Ser Tyr Leu Pro Asp Pro Ala Ser Ile Asn Asn His Gln
                85                  90                  95

Ile Pro Thr Ser Ser Lys Val Ser Tyr Leu Thr Gly Lys Gly Lys Ser
            100                 105                 110

Met Leu Arg Lys Lys Lys Thr Asp Ser Phe Thr Asn Gly Ala Arg Asp
        115                 120                 125

Gln Asp Lys Leu Gly Pro Lys Leu Thr Glu Thr Val Lys Arg Lys Leu

```
                130                 135                 140
Ser Leu Gly Ala Lys Ile Leu Gln Met Gly Gly Leu Glu Lys Ile Tyr
145                 150                 155                 160

Lys Arg Leu Phe Lys Val Cys Asp Gln Glu Lys Leu Phe Lys Ala Tyr
                165                 170                 175

Gln Cys Tyr Leu Ser Thr Thr Ala Gly Pro Ile Ala Gly Leu Leu Phe
            180                 185                 190

Ile Ser Ser Lys Lys Ile Ala Phe Cys Ser Glu Arg Ser Ile Lys Val
        195                 200                 205

Ala Ser Pro Gln Gly Val Leu Ser Arg Val His Tyr Lys Val Ser Ile
210                 215                 220

Pro Leu Cys Lys Ile Asn Gly Val Asn Gln Ser Gln Asn Thr Lys Lys
225                 230                 235                 240

Pro Ser Gln Lys Tyr Leu Glu Ile Val Thr Ile Asp Asn Phe Asp Phe
                245                 250                 255

Trp Phe Met Gly Phe Val Ser Tyr Gln Lys Ala Phe Asn Cys Leu Glu
            260                 265                 270

Lys Ala Leu Asn Asn Asp Glu Gln
        275                 280

<210> SEQ ID NO 13
<211> LENGTH: 958
<212> TYPE: DNA
<213> ORGANISM: Arabidopsis thaliana

<400> SEQUENCE: 13
cacaatttct ctctctctct ctcgttctca caagatcaag aatatcaaga acaagatca       60 cttctcaatc ctcgaagatg acattgagca gagttcatca acaagttatt gcatttcctg     120
ctgtcaatac tgctccggtg ggttacttgc ctgatccagc ttccatcaac aagcttcaaa     180
tcccaacttc ttcaaaggtt tcgatgcttc aaaagaagaa aaccgatagc ttcacaaacg     240
gagcaagaga tcaggacaag ttaggaccca agctaaccga acagtaaag agaaagctat      300 ccttgggagc taagatcctt caaatgggag cttagagaa gatctataag cgactcttca     360
aggtctgcga taagagaaa ctcttcaagg cgtaccaatg ttacctatcg acaacagaag    420
gttccattgc gggcctgctc ttcatctcat caaagaagat tgccttctgt agcgaaagat    480
cgatcaaggt gacttctcct caaggagatc tcactagggt tcactacaaa gtctcaatcc    540
ccttgtgcaa gatcaatgga gtgaaccaga gtcagaacac gaagaaacca tctcagaggt    600
acctagaagt agtcacagtc gataactatg acttctggtt catgggattc gtgagctacc    660
agaaagcttt caactgtctc gagaaagcgc taaacgagga tgagcaataa acggaggagc    720
tactaattag tgcatggtgg aaaaagaaat atatcatttc tattttcacc tgtttcaatc    780
agggaatgtt aggagagaac ctagtagaga ctgacaatat tgtttgtaca aactcaattc    840 ttatttcat tgtattttgc tttttggttt ctattgtaga aacgagaaag aaattaatat      900
acttagccga tttcatcagt tttccttaat aaatagtttt cttttgcacc aaattaca      958

<210> SEQ ID NO 14
<211> LENGTH: 210
<212> TYPE: PRT
<213> ORGANISM: Arabidopsis thaliana

<400> SEQUENCE: 14

Met Thr Leu Ser Arg Val His Gln Gln Val Ile Ala Phe Pro Ala Val
1               5                   10                  15
```

Asn Thr Ala Pro Val Gly Tyr Leu Pro Asp Pro Ala Ser Ile Asn Lys
            20                  25                  30

Leu Gln Ile Pro Thr Ser Ser Lys Val Ser Met Leu Gln Lys Lys Lys
        35                  40                  45

Thr Asp Ser Phe Thr Asn Gly Ala Arg Asp Gln Asp Lys Leu Gly Pro
    50                  55                  60

Lys Leu Thr Glu Thr Val Lys Arg Lys Leu Ser Leu Gly Ala Lys Ile
65                  70                  75                  80

Leu Gln Met Gly Gly Leu Glu Lys Ile Tyr Lys Arg Leu Phe Lys Val
                85                  90                  95

Cys Asp Lys Glu Lys Leu Phe Lys Ala Tyr Gln Cys Tyr Leu Ser Thr
            100                 105                 110

Thr Glu Gly Ser Ile Ala Gly Leu Leu Phe Ile Ser Ser Lys Lys Ile
        115                 120                 125

Ala Phe Cys Ser Glu Arg Ser Ile Lys Val Thr Ser Pro Gln Gly Asp
    130                 135                 140

Leu Thr Arg Val His Tyr Lys Val Ser Ile Pro Leu Cys Lys Ile Asn
145                 150                 155                 160

Gly Val Asn Gln Ser Gln Asn Thr Lys Lys Pro Ser Gln Arg Tyr Leu
                165                 170                 175

Glu Val Val Thr Val Asp Asn Tyr Asp Phe Trp Phe Met Gly Phe Val
            180                 185                 190

Ser Tyr Gln Lys Ala Phe Asn Cys Leu Glu Lys Ala Leu Asn Glu Asp
        195                 200                 205

Glu Gln
    210

<210> SEQ ID NO 15
<211> LENGTH: 941
<212> TYPE: DNA
<213> ORGANISM: Arabidopsis thaliana

<400> SEQUENCE: 15

```
atcactcaca atctctctct cttactcttt cacaaaatca agaatcaaga tcactactca    60
attctccaag atgacattga gcagagttca ccaacaactc attacatttc ctgccgtcaa   120
gacttctccg gcgggttact tgcctgatcc agcttccatc aacaagcttc aaatcccaac   180
ttcttcaaag ttttctttc taacaggcaa aggaaaatcg atgctacgaa agaagaaaaa   240
cgatagcttc acaaacggag ttagagatca ggacaagtta ggaccaaagc taaccgaaac   300
agtcaagaga aaactatcct tgggagctag gatccttcaa atgggaggct tagagaagat   360
ctataaacga ctctttaagg tcagcgatga agagaaactc ttcaaggcgt accaatgcta   420
cctatccaca accgcaggtc ccatcgctgg cctactcttc atatcatcaa agaaaattgc   480
attctgcagc gaaagatcga tcaaggtggc ttctcctcaa ggagagctca atagggttca   540
ctacaaagtc tcaatcccct gtgcaagat caatggagtg aaccagagtc aaaacacaac   600
gaagccatct cagaagtacc ttgaagtagt cacggtcgac ggctttgact tctggttcat   660
gggattcttg agctaccaaa aagctttcaa ctgcctcgag caagcgcttt ctcttagctt   720
caagcaatga taagccaaga tatattgctt ccattgagga gctaattagt gtgggtaaaa   780
gaggaaatat ttcatttcac tttaacctac ttcaatcaga ttatgttagg aaatgcccta   840
gaaaccattg acaatattgt acaaactcat tttttttctt ttcttatatc tcttttgttc   900
ttcatcgtta acatgagcaa gagatttgaa tatatttagt t                       941
```

<210> SEQ ID NO 16
<211> LENGTH: 219
<212> TYPE: PRT
<213> ORGANISM: Arabidopsis thaliana

<400> SEQUENCE: 16

Met Thr Leu Ser Arg Val His Gln Gln Leu Ile Thr Phe Pro Ala Val
1               5                   10                  15

Lys Thr Ser Pro Ala Gly Tyr Leu Pro Asp Pro Ala Ser Ile Asn Lys
            20                  25                  30

Leu Gln Ile Pro Thr Ser Ser Lys Phe Ser Phe Leu Thr Gly Lys Gly
        35                  40                  45

Lys Ser Met Leu Arg Lys Lys Asn Asp Ser Phe Thr Asn Gly Val
    50                  55                  60

Arg Asp Gln Asp Lys Leu Gly Pro Lys Leu Thr Glu Thr Val Lys Arg
65                  70                  75                  80

Lys Leu Ser Leu Gly Ala Arg Ile Leu Gln Met Gly Gly Leu Glu Lys
                85                  90                  95

Ile Tyr Lys Arg Leu Phe Lys Val Ser Asp Glu Glu Lys Leu Phe Lys
            100                 105                 110

Ala Tyr Gln Cys Tyr Leu Ser Thr Thr Ala Gly Pro Ile Ala Gly Leu
        115                 120                 125

Leu Phe Ile Ser Ser Lys Lys Ile Ala Phe Cys Ser Glu Arg Ser Ile
    130                 135                 140

Lys Val Ala Ser Pro Gln Gly Glu Leu Asn Arg Val His Tyr Lys Val
145                 150                 155                 160

Ser Ile Pro Leu Cys Lys Ile Asn Gly Val Asn Gln Ser Gln Asn Thr
                165                 170                 175

Thr Lys Pro Ser Gln Lys Tyr Leu Glu Val Val Thr Val Asp Gly Phe
            180                 185                 190

Asp Phe Trp Phe Met Gly Phe Leu Ser Tyr Gln Lys Ala Phe Asn Cys
        195                 200                 205

Leu Glu Gln Ala Leu Ser Leu Ser Phe Lys Gln
    210                 215

<210> SEQ ID NO 17
<211> LENGTH: 940
<212> TYPE: DNA
<213> ORGANISM: Arabidopsis thaliana

<400> SEQUENCE: 17
atgaatggga gagttagaac taattttgag aggtttctcg aatgttcatc tccacgtgtc      60
ccgattcaat tttatactca ggcaagggga tcgtcttctt cttcaccaat agctttggga     120
gctattgaag aagaagaagt gagaaagcct cgcatcgtcc tcaatgatat tggtctgcc      180 tgtaaaaact ggagcactgt tggtatcgaa gtccctcttt cgctggaaaa cttcgactcc     240
gatgttaaac agtactataa tccttcactc tccgccattc agatctttac catcaaaccc     300
ttctctgatg attcaaggag ctctgccatt gggatagatg gtacagagac aggatctgct     360
ataactgact ctgacagcaa cggcaagctt cagtgtttgg atgctggtga cttgggctac     420
ctttattttc aatataatga ggtagaaagg ccatttgata ggtttcctct cactttcaag     480
atggctgacc tagctgagga gcacactgga ctgtctagtc tgacgagttc agatcttttct    540 ccaaatagct ggatttcgat agcttggtat cccatttatc caattccacc agtgataggc     600
gtggacggga tatctgccgc tttcctaacg taccatttat tgaagccaaa ctttccagaa     660
acaattggta aggatgataa ggggaatgaa caaggagagt caagtacacc agaagttcta     720

```
cttcctccat tggagcaat gacttacaag gcctttggta acctgtggat gatgcctggg    780
acatcagatt atcagaacag agagatgaat gaagaatctg ctgactcgtg gctgagaaaa    840
cgcggcttct cccacagcga tttcaacttc tttatgtccc gtaagttta cggcggaccc     900 tattaatgcc atcttgcagg tgaaatgcta agcctaacaa                          940
```

```
<210> SEQ ID NO 18
<211> LENGTH: 301
<212> TYPE: PRT
<213> ORGANISM: Arabidopsis thaliana

<400> SEQUENCE: 18
```

Met Asn Gly Arg Val Arg Thr Asn Phe Glu Arg Phe Leu Glu Cys Ser
1               5                   10                  15

Ser Pro Arg Val Pro Ile Gln Phe Tyr Thr Gln Ala Arg Gly Ser Ser
            20                  25                  30

Ser Ser Ser Pro Ile Ala Leu Gly Ala Ile Glu Glu Glu Val Arg
        35                  40                  45

Lys Pro Arg Ile Val Leu Asn Asp Ile Trp Ser Ala Cys Lys Asn Trp
50                  55                  60

Ser Thr Val Gly Ile Glu Val Pro Leu Ser Leu Glu Asn Phe Asp Ser
65                  70                  75                  80

Asp Val Lys Gln Tyr Tyr Asn Pro Ser Leu Ser Ala Ile Gln Ile Phe
                85                  90                  95

Thr Ile Lys Pro Phe Ser Asp Asp Ser Arg Ser Ser Ala Ile Gly Ile
            100                 105                 110

Asp Gly Thr Glu Thr Gly Ser Ala Ile Thr Asp Ser Asp Ser Asn Gly
        115                 120                 125

Lys Leu Gln Cys Leu Asp Ala Gly Asp Leu Gly Tyr Leu Tyr Phe Gln
130                 135                 140

Tyr Asn Glu Val Glu Arg Pro Phe Asp Arg Phe Pro Leu Thr Phe Lys
145                 150                 155                 160

Met Ala Asp Leu Ala Glu Glu His Thr Gly Leu Ser Ser Leu Thr Ser
                165                 170                 175

Ser Asp Leu Ser Pro Asn Ser Trp Ile Ser Ile Ala Trp Tyr Pro Ile
            180                 185                 190

Tyr Pro Ile Pro Pro Val Ile Gly Val Asp Gly Ile Ser Ala Ala Phe
        195                 200                 205

Leu Thr Tyr His Leu Leu Lys Pro Asn Phe Pro Glu Thr Ile Gly Lys
210                 215                 220

Asp Asp Lys Gly Asn Glu Gln Gly Glu Ser Ser Thr Pro Glu Val Leu
225                 230                 235                 240

Leu Pro Pro Phe Gly Ala Met Thr Tyr Lys Ala Phe Gly Asn Leu Trp
                245                 250                 255

Met Met Pro Gly Thr Ser Asp Tyr Gln Asn Arg Glu Met Asn Glu Glu
            260                 265                 270

Ser Ala Asp Ser Trp Leu Arg Lys Arg Gly Phe Ser His Ser Asp Phe
        275                 280                 285

Asn Phe Phe Met Ser Arg Lys Phe Tyr Gly Gly Pro Tyr
290                 295                 300

```
<210> SEQ ID NO 19
<211> LENGTH: 2621
<212> TYPE: DNA
<213> ORGANISM: Arabidopsis thaliana
```

-continued

```
<400> SEQUENCE: 19
aattaatttt ctcactcaat aatgaagaaa actgcgaaag cgtgcagata agagagatct      60
ctctgaacag atattatagt tgatagtttg cgtactagga gtctgtgaaa gcttgcacag     120
gaagaaagca atcgggaaa gaaaggaatc tgaatcggag aagcaatcga ggtttacgat      180
taccaaattc tgatctaatc tgattaattg tggtgatttc cgatggaaga agacggtggt     240
ggcggcggtg cgaaagttgg aatgctggag aatttcatga agacgcatca gagttctttg     300
aaatcgttat tccagagaaa gaaatcatcc tctggtcgtg atggagatgc ttctccgtcg     360
cctatcgctt ccccgaaacc tattccgcag ctctctcttc tcgccaattc cgtcgtctcc     420
cgctgttcaa agatcctgaa cattcaaaca gaagatctgc agcatcattt tgatgtagag     480
ttgcctgaga gtgttaagca actattgaca tatgcaagga acttttttaga gttctgctct    540 tttcaggcac ttcatcaagt gatgaaaaaa cctgattact tgagtgatca agagttccgt     600
cagctaatgt tgacatgat gcttgcttgg gagactccca gtgtcacaag tgagcaggaa      660
aacaaagatg cagcatctcc ctccaagcag gactcagagg atgaggatgg atggtcgcta     720
ttctattcaa gtcccactaa tatggcaatg caggttgatg aaaaaaagtc tgtcggacag     780
gaggcttttg caagaattgc tccggtttgt cctgccattg cagatgcaat aactgtacat     840 aatcttttg atgcactaac tagctcgtca ggccacaggc ttcattatat cgtatatgac      900
aaatacctcc gcacacttga caaaattttc aaggctgcaa aaagcactct aggaccttca     960
gctgccaatc ttcagcttgc caagggagaa atagtgcttg atatggatgg tgcaaatcct    1020
gttttaccgg ttcttaaaca cgtgggcatc tcagcatggc ctggtaaact gacacttacc    1080
aactgtgctc tatattttga ttcaatgggt ggtggtgaaa agcccatgcg atatgatctc    1140
actgaagaca caaaacaggt catcaaacct gagttgacag ggccattggg tgctcgtata    1200
tttgataaag ccattatgta taaatcaatt acagtaccag agccagtatt ttttgaattt    1260
acagagttta aaggcaatgc tcgtcgagac tactggttgg gaatttgcct ggagatcctt    1320
cgtgtacaat ggttcatacg aagatacaac tttaaaggga ttcaacgatc agaaatactt    1380
gcaagagcaa tccttgggat attccggtac cgtgcaataa gggaagcttt tcaagtcttc    1440
tcttcccaat acaaaacatt gcttatattt aacctggcag aaagtctccc cggcggagat    1500
atggtcttag aagctctgtc cagccgtgtc tctcgcataa ccactaatgt tgcttctgat    1560
atcggttctg ttcagtatat gaaatggccc tcaaacttat ctccagtctc actcaaattg    1620
cttgagcatt ttggcttgaa tctagaaaca gggacaaata tgggtgaaga attgacaatc    1680
gtaggagatt tttgtgttgg ggagacgagt ccattggaga tagctctgaa acagtcaatc    1740
ctagacacag acagagctga agctgctcag gcgactgtgg aacaagtgaa agtagaagga    1800
attgacacta acgttgcagt tatgaaggag ctattgttac ctttcatcaa actaggcttg    1860
catataaatc gcttagccta ttggcaagat ccttataaat caacggtgtt catgatcttg    1920
gtcagctata tgattatcag tgggtggatc ggtttcatat taccgtcaat attactccta    1980
gtagctatag taatgatgtg gcgtaagcaa ttcaacaaag ggaaagaacc aaaaaccgtt    2040
cgtgtgaaag ctccaccaag taaaaacgcg gtggagcagc ttctcgtact acaagatgca    2100
attagccagt tcgagtcgct aatccaagct gttaacgttg gtctcctcaa aataagagca    2160
attacccttg caattcttcc tcaggcgaca gatacaacgg ctatatcgct tgtggttgtg    2220
gcagttatat tggcggttgt tcctgttaag tacttaataa cggttgcgtt tgtagagtgg    2280
ttcacgaggg aagttgggtg gaggaaagcg agtagtgacc ggctagagag gcggataaga    2340
```

```
gaatggtggt ttagggtacc agcagctcct gttcagctca ttagagccga agatagcaag    2400
aagaagaaga aatgacactt ttcaattctc tcacacgcat tgtctctctt tctagacata    2460
ttgttttgat attagaattt tttattcttc ttcttttttt ttcccctttt taagtaagat    2520
tcgggtttat tcataaatat gagacgaact aactcgtttt ttgactttta actacccagt    2580
ttgacaaaaa caagttcttc aattggcaaa gtaatgtcac a                        2621

<210> SEQ ID NO 20
<211> LENGTH: 730
<212> TYPE: PRT
<213> ORGANISM: Arabidopsis thaliana

<400> SEQUENCE: 20

Met Glu Glu Asp Gly Gly Gly Gly Ala Lys Val Gly Met Leu Glu
1               5                   10                  15

Asn Phe Met Lys Thr His Gln Ser Ser Leu Lys Ser Leu Phe Gln Arg
            20                  25                  30

Lys Lys Ser Ser Ser Gly Arg Asp Gly Asp Ala Ser Pro Ser Pro Ile
        35                  40                  45

Ala Ser Pro Lys Pro Ile Pro Gln Leu Ser Leu Leu Ala Asn Ser Val
    50                  55                  60

Val Ser Arg Cys Ser Lys Ile Leu Asn Ile Gln Thr Glu Asp Leu Gln
65                  70                  75                  80

His His Phe Asp Val Glu Leu Pro Glu Ser Val Lys Gln Leu Leu Thr
                85                  90                  95

Tyr Ala Arg Asn Phe Leu Glu Phe Cys Ser Phe Gln Ala Leu His Gln
            100                 105                 110

Val Met Lys Lys Pro Asp Tyr Leu Ser Asp Gln Glu Phe Arg Gln Leu
        115                 120                 125

Met Phe Asp Met Met Leu Ala Trp Glu Thr Pro Ser Val Thr Ser Glu
    130                 135                 140

Gln Glu Asn Lys Asp Ala Ala Ser Pro Ser Lys Gln Asp Ser Glu Asp
145                 150                 155                 160

Glu Asp Gly Trp Ser Leu Phe Tyr Ser Ser Pro Thr Asn Met Ala Met
                165                 170                 175

Gln Val Asp Glu Lys Lys Ser Val Gly Gln Glu Ala Phe Ala Arg Ile
            180                 185                 190

Ala Pro Val Cys Pro Ala Ile Ala Asp Ala Ile Thr Val His Asn Leu
        195                 200                 205

Phe Asp Ala Leu Thr Ser Ser Gly His Arg Leu His Tyr Ile Val
    210                 215                 220

Tyr Asp Lys Tyr Leu Arg Thr Leu Asp Lys Ile Phe Lys Ala Ala Lys
225                 230                 235                 240

Ser Thr Leu Gly Pro Ser Ala Ala Asn Leu Gln Leu Ala Lys Gly Glu
                245                 250                 255

Ile Val Leu Asp Met Asp Gly Ala Asn Pro Val Leu Pro Val Leu Lys
            260                 265                 270

His Val Gly Ile Ser Ala Trp Pro Gly Lys Leu Thr Leu Thr Asn Cys
        275                 280                 285

Ala Leu Tyr Phe Asp Ser Met Gly Gly Gly Glu Lys Pro Met Arg Tyr
    290                 295                 300

Asp Leu Thr Glu Asp Thr Lys Gln Val Ile Lys Pro Glu Leu Thr Gly
305                 310                 315                 320

Pro Leu Gly Ala Arg Ile Phe Asp Lys Ala Ile Met Tyr Lys Ser Ile
                325                 330                 335
```

```
Thr Val Pro Glu Pro Val Phe Glu Phe Thr Glu Phe Lys Gly Asn
        340                 345                 350

Ala Arg Arg Asp Tyr Trp Leu Gly Ile Cys Leu Glu Ile Leu Arg Val
        355                 360                 365

Gln Trp Phe Ile Arg Arg Tyr Asn Phe Lys Gly Ile Gln Arg Ser Glu
        370                 375                 380

Ile Leu Ala Arg Ala Ile Leu Gly Ile Phe Arg Tyr Arg Ala Ile Arg
385                 390                 395                 400

Glu Ala Phe Gln Val Phe Ser Ser Gln Tyr Lys Thr Leu Leu Ile Phe
            405                 410                 415

Asn Leu Ala Glu Ser Leu Pro Gly Gly Asp Met Val Leu Glu Ala Leu
            420                 425                 430

Ser Ser Arg Val Ser Arg Ile Thr Thr Asn Val Ala Ser Asp Ile Gly
            435                 440                 445

Ser Val Gln Tyr Met Lys Trp Pro Ser Asn Leu Ser Pro Val Ser Leu
        450                 455                 460

Lys Leu Leu Glu His Phe Gly Leu Asn Leu Glu Thr Gly Thr Asn Met
465                 470                 475                 480

Gly Glu Glu Leu Thr Ile Val Gly Asp Phe Cys Val Gly Glu Thr Ser
                485                 490                 495

Pro Leu Glu Ile Ala Leu Lys Gln Ser Ile Leu Asp Thr Asp Arg Ala
            500                 505                 510

Glu Ala Ala Gln Ala Thr Val Glu Gln Val Lys Val Glu Gly Ile Asp
            515                 520                 525

Thr Asn Val Ala Val Met Lys Glu Leu Leu Leu Pro Phe Ile Lys Leu
530                 535                 540

Gly Leu His Ile Asn Arg Leu Ala Tyr Trp Gln Asp Pro Tyr Lys Ser
545                 550                 555                 560

Thr Val Phe Met Ile Leu Val Ser Tyr Met Ile Ile Ser Gly Trp Ile
                565                 570                 575

Gly Phe Ile Leu Pro Ser Ile Leu Leu Val Ala Ile Val Met Met
            580                 585                 590

Trp Arg Lys Gln Phe Asn Lys Gly Lys Glu Pro Lys Thr Val Arg Val
        595                 600                 605

Lys Ala Pro Pro Ser Lys Asn Ala Val Glu Gln Leu Leu Val Leu Gln
        610                 615                 620

Asp Ala Ile Ser Gln Phe Glu Ser Leu Ile Gln Ala Val Asn Val Gly
625                 630                 635                 640

Leu Leu Lys Ile Arg Ala Ile Thr Leu Ala Ile Leu Pro Gln Ala Thr
                645                 650                 655

Asp Thr Thr Ala Ile Ser Leu Val Val Val Ala Val Ile Leu Ala Val
            660                 665                 670

Val Pro Val Lys Tyr Leu Ile Thr Val Ala Phe Val Glu Trp Phe Thr
        675                 680                 685

Arg Glu Val Gly Trp Arg Lys Ala Ser Ser Asp Arg Leu Glu Arg Arg
        690                 695                 700

Ile Arg Glu Trp Trp Phe Arg Val Pro Ala Ala Pro Val Gln Leu Ile
705                 710                 715                 720

Arg Ala Glu Asp Ser Lys Lys Lys Lys
                725                 730

<210> SEQ ID NO 21
<211> LENGTH: 960
<212> TYPE: DNA
```

-continued

<213> ORGANISM: Arabidopsis thaliana

<400> SEQUENCE: 21

```
ttcaaacaaa ctgatatatt cattgtacac gagtcttttc tggttgaata tatttttaca      60
ttcattcaaa taagaaaaat gtctcatcgt acagatgcga tcatctggtt tctgaaaaga     120
agagagagac tagaatatgg aaaaattcaa attcaagccc aataaaccct gaacaaaatt     180
taaagcctgg cccttgtctg accatctggg ccttcttttg atttcaattt tgggaaattc     240
agattgcgtc gacgcatttc ttttgaggga tggatctgct ttctcgtcgg cggctaatca     300
aattcttcca gagggttttg aaagaaattt ctcgagatgg gtcaagctca aagtgacgag     360
aactcaattc cgacgacgac gacaacgaac actcctcctc cttctgcgaa ttcacctcgg     420
gattctgaag atacttcgtc gccatcgatg gattctcttc ttgcagaagc tgcagcatat     480
ggtgaagatg ataatgagaa tgagtctctt gaagccaaag cacagagagc tctcgattgt     540
ccttgtatag cagatttgcg taatggctct tgcgggtctc agttctccga ggcattcctt     600
tgctttctca aaagcactgc tgaagaaaag ggatcagact gcgtgaatcc atttgtagca     660
ttgcaaagct gtatcaatgc caatccggat gcattctcta atcagttac aggggacgaa     720
aaagaaaccg agaaaaagga gagcagcct cctgtgcaag accatagaat catccctcct     780
ctctgggcca agacccgcc tcgcagtggc aattccaagc tttagaatat caacaacaat     840
ggagtcagca tcagaagcta gtctctcctc ttttgattct tttctctaga cagcactttt     900
aagaatgtaa agaagagta gaagaccatg atcagtggtc gtgtagatca acattgttct     960
```

<210> SEQ ID NO 22
<211> LENGTH: 162
<212> TYPE: PRT
<213> ORGANISM: Arabidopsis thaliana

<400> SEQUENCE: 22

```
Met Gly Gln Ala Gln Ser Asp Glu Asn Ser Ile Pro Thr Thr Thr Thr
1               5                   10                  15

Thr Asn Thr Pro Pro Ser Ala Asn Ser Pro Arg Asp Ser Glu Asp
            20                  25                  30

Thr Ser Ser Pro Ser Met Asp Ser Leu Leu Ala Glu Ala Ala Ala Tyr
        35                  40                  45

Gly Glu Asp Asp Asn Glu Asn Glu Ser Leu Glu Ala Lys Ala Gln Arg
    50                  55                  60

Ala Leu Asp Cys Pro Cys Ile Ala Asp Leu Arg Asn Gly Ser Cys Gly
65                  70                  75                  80

Ser Gln Phe Ser Glu Ala Phe Leu Cys Phe Leu Lys Ser Thr Ala Glu
                85                  90                  95

Glu Lys Gly Ser Asp Cys Val Asn Pro Phe Val Ala Leu Gln Ser Cys
            100                 105                 110

Ile Asn Ala Asn Pro Asp Ala Phe Ser Lys Ser Val Thr Gly Asp Glu
        115                 120                 125

Lys Glu Thr Glu Lys Lys Glu Glu Gln Pro Val Gln Asp His Arg
    130                 135                 140

Ile Ile Pro Pro Leu Trp Ala Lys Asp Pro Pro Arg Ser Gly Asn Ser
145                 150                 155                 160

Lys Leu
```

<210> SEQ ID NO 23
<211> LENGTH: 924
<212> TYPE: DNA

<213> ORGANISM: Arabidopsis thaliana

<400> SEQUENCE: 23

```
atggctcttg ttcgtaaacg ccgtcaaatc aacctccgtc tccctgtccc accgctctct    60
gttcacctcc cctggttctc ctttgcctca tccaccgccc ccgtcatcaa caacggaatc   120
tcagcttccg atgtcgagaa actccacgtt ctcggaagag aagcagcgg  atcgtatac   180
aaagtccacc acaaaaccac gggggagata tacgctctga atcagtcaa  cggcgacatg   240
agtcctgctt tcacaagaca attagcgcgc gagatggaga tcctccgtcg cacggattct   300
ccttatgtcg tcaggtgtca agggatcttc gagaaaccaa tcgtcggaga ggtttcgatc   360
ctcatggagt atatggacgg tggaaaccta gaatctctcc gcggcgccgt tacggagaaa   420
caactagcgg gattttcccg ccagattttg aaaggtttaa gttatctcca ctcactcaag   480
atcgttcaca gagacatcaa acctgcgaat ctactcttaa actcgagaaa cgaagttaaa   540
atcgctgatt ttggagtgag caaaatcatt acccgatcgt tagattactg caattcctac   600
gtcggcactt gcgcttacat gagcccggag agatttgact ctgccgccgg agaaaactcc   660
gatgtttacg caggcgatat ctggagtttc ggagtgatga tacttgagct cttcgtcgga   720
cattttccgt tgcttcctca gggacagaga cctgactggg cgacgttaat gtgcgtcgtg   780
tgctttggag aaccaccgcg tgcgccgaa  ggatgttccg acgagtttag gagttttgtt   840
gactgttgtc tccgtaaaga atcgagtgag aggtggacgg cgtcgcagct tctcggtcac   900
cctttctcc  gtgaaagtct ttag                                          924
```

<210> SEQ ID NO 24
<211> LENGTH: 307
<212> TYPE: PRT
<213> ORGANISM: Arabidopsis thaliana

<400> SEQUENCE: 24

```
Met Ala Leu Val Arg Lys Arg Arg Gln Ile Asn Leu Arg Leu Pro Val
1               5                   10                  15

Pro Pro Leu Ser Val His Leu Pro Trp Phe Ser Phe Ala Ser Ser Thr
            20                  25                  30

Ala Pro Val Ile Asn Asn Gly Ile Ser Ala Ser Asp Val Glu Lys Leu
        35                  40                  45

His Val Leu Gly Arg Gly Ser Ser Gly Ile Val Tyr Lys Val His His
    50                  55                  60

Lys Thr Thr Gly Glu Ile Tyr Ala Leu Lys Ser Val Asn Gly Asp Met
65                  70                  75                  80

Ser Pro Ala Phe Thr Arg Gln Leu Ala Arg Glu Met Glu Ile Leu Arg
                85                  90                  95

Arg Thr Asp Ser Pro Tyr Val Val Arg Cys Gln Gly Ile Phe Glu Lys
            100                 105                 110

Pro Ile Val Gly Glu Val Ser Ile Leu Met Glu Tyr Met Asp Gly Gly
        115                 120                 125

Asn Leu Glu Ser Leu Arg Gly Ala Val Thr Glu Lys Gln Leu Ala Gly
    130                 135                 140

Phe Ser Arg Gln Ile Leu Lys Gly Leu Ser Tyr Leu His Ser Leu Lys
145                 150                 155                 160

Ile Val His Arg Asp Ile Lys Pro Ala Asn Leu Leu Leu Asn Ser Arg
                165                 170                 175

Asn Glu Val Lys Ile Ala Asp Phe Gly Val Ser Lys Ile Ile Thr Arg
            180                 185                 190
```

```
Ser Leu Asp Tyr Cys Asn Ser Tyr Val Gly Thr Cys Ala Tyr Met Ser
        195                 200                 205
Pro Glu Arg Phe Asp Ser Ala Ala Gly Glu Asn Ser Asp Val Tyr Ala
    210                 215                 220
Gly Asp Ile Trp Ser Phe Gly Val Met Ile Leu Glu Leu Phe Val Gly
225                 230                 235                 240
His Phe Pro Leu Leu Pro Gln Gly Gln Arg Pro Asp Trp Ala Thr Leu
                245                 250                 255
Met Cys Val Val Cys Phe Gly Glu Pro Pro Arg Ala Pro Glu Gly Cys
            260                 265                 270
Ser Asp Glu Phe Arg Ser Phe Val Asp Cys Cys Leu Arg Lys Glu Ser
        275                 280                 285
Ser Glu Arg Trp Thr Ala Ser Gln Leu Leu Gly His Pro Phe Leu Arg
    290                 295                 300
Glu Ser Leu
305

<210> SEQ ID NO 25
<211> LENGTH: 1673
<212> TYPE: DNA
<213> ORGANISM: Arabidopsis thaliana

<400> SEQUENCE: 25
aaaatattat ttaaatgtta atgttgttct ctcgaatcat tccttaagaa agattttcac      60
tttccaattt gcttcactgt cttgtcgatt ctgcttctcc aaaaaatttc ttctttagtt     120
ctgagttttt ctctgttctg aaaaacccca aattttgttt tttttggcca ttcaaaattt     180
cagaagaagg cgatacaaaa tcgtctttga attctctttg tttatgatct gttcaagtaa     240
aggaacggtc gtaattgcta ctagaagctc atttcccaga ttactaaacc ggattcaaaa     300
tcgaaatgat gttccgatta gtgtcatagc tactcgacga tcatcaatgt cggtggaggc     360
gtttccgatg aggttaaaat catcacagaa gaagaggaag atgaacattg gttgcggtgt     420
ttccccttct tcgccgacga cgacggtggt agatgaggaa gtagccatta ggcgaaaatt     480
ggcaatgaga cgggttttgg aggataacgg tggcgatgga agctccgtca gagatttctc     540
gctattcacg accaagagag gtgacacgtt gttcactcag tcatggactc ctgttgactc     600
cgctaagaac aggggacttg ttgttctgct tcatggtctg aacgaacaca gtggcaggta     660
tagtgatttt gcaaagcagc taaatgtaaa tggattcaag gtctatggaa tagattggat     720
cggtcatggt ggaagcgatg gacttcatgc ttacgttcct tctcttgatt atgctgtcgc     780
tgatttgaaa tcgtttattg agaaggtaat tgcggaaaac ccgggattgc cctgtttctg     840
cattggccac tcaacaggag gagccatcat cttaaaggct atgctagatg caaagattga     900
agctcgagtt tcagggattg tgctaacttc acccgcagtt ggagtccaac caacttatcc     960
tatcttcggc gtaattgcac cattcctctc gttcctcata ccgagatatc agttaagtgc    1020
tgcgaaaaag aaaataatgc cggtttctcg tgacccggaa gctctattgg ctaaatactc    1080
tgacccgcta gtctacactg gatttatccg agcaagaacc ggtaacgaga tccttagact    1140
tggtgctcat ttactgcaga atctgaacag aatcaaggtt ccgtttcttg tgatgcacgg    1200
cacagctgat acagttactg atcctaaagg tactcagaag ctatacaatg aggcttcctc    1260
atccgataag tcgatcaagc tgtacgacgg gttgttacac gatctgctct ttgaaccaga    1320
acgggaaact atagctggag tcatattgga ttggctaaac cggcgggttt aaattcctca    1380
aaccaaatgt agcacagttc cttactccct aggtaatata gagggatatg cgaaagacat    1440
```

```
aatcaatagt tcctctgttt ctgtcgattg atctcgacac tattttgaca ttacgcacac    1500
ttttattgta atgaatatac gatgttgtaa ctctgttagt ggtcatcgta accatttctt    1560
gtataaacga tactagattt atattttgtt gataggagaa taatcataat tatatatggg    1620
gtttataaga atatgaatcg tcagatgaat ttcaatagag catatttctg atc           1673
```

<210> SEQ ID NO 26
<211> LENGTH: 382
<212> TYPE: PRT
<213> ORGANISM: Arabidopsis thaliana

<400> SEQUENCE: 26

```
Met Ile Cys Ser Ser Lys Gly Thr Val Val Ile Ala Thr Arg Ser Ser
1               5                   10                  15

Phe Pro Arg Leu Leu Asn Arg Ile Gln Asn Arg Asn Asp Val Pro Ile
            20                  25                  30

Ser Val Ile Ala Thr Arg Arg Ser Ser Met Ser Val Glu Ala Phe Pro
        35                  40                  45

Met Arg Leu Lys Ser Ser Gln Lys Lys Arg Lys Met Asn Ile Gly Cys
    50                  55                  60

Gly Val Ser Pro Ser Ser Pro Thr Thr Thr Val Val Asp Glu Glu Val
65                  70                  75                  80

Ala Ile Arg Arg Lys Leu Ala Met Arg Arg Val Leu Glu Asp Asn Gly
                85                  90                  95

Gly Asp Gly Ser Ser Val Arg Asp Phe Ser Leu Phe Thr Thr Lys Arg
            100                 105                 110

Gly Asp Thr Leu Phe Thr Gln Ser Trp Thr Pro Val Asp Ser Ala Lys
        115                 120                 125

Asn Arg Gly Leu Val Val Leu Leu His Gly Leu Asn Glu His Ser Gly
    130                 135                 140

Arg Tyr Ser Asp Phe Ala Lys Gln Leu Asn Val Asn Gly Phe Lys Val
145                 150                 155                 160

Tyr Gly Ile Asp Trp Ile Gly His Gly Gly Ser Asp Gly Leu His Ala
                165                 170                 175

Tyr Val Pro Ser Leu Asp Tyr Ala Val Ala Asp Leu Lys Ser Phe Ile
            180                 185                 190

Glu Lys Val Ile Ala Glu Asn Pro Gly Leu Pro Cys Phe Cys Ile Gly
        195                 200                 205

His Ser Thr Gly Gly Ala Ile Ile Leu Lys Ala Met Leu Asp Ala Lys
    210                 215                 220

Ile Glu Ala Arg Val Ser Gly Ile Val Leu Thr Ser Pro Ala Val Gly
225                 230                 235                 240

Val Gln Pro Thr Tyr Pro Ile Phe Gly Val Ile Ala Pro Phe Leu Ser
                245                 250                 255

Phe Leu Ile Pro Arg Tyr Gln Leu Ser Ala Ala Lys Lys Lys Ile Met
            260                 265                 270

Pro Val Ser Arg Asp Pro Glu Ala Leu Leu Ala Lys Tyr Ser Asp Pro
        275                 280                 285

Leu Val Tyr Thr Gly Phe Ile Arg Ala Arg Thr Gly Asn Glu Ile Leu
    290                 295                 300

Arg Leu Gly Ala His Leu Leu Gln Asn Leu Asn Arg Ile Lys Val Pro
305                 310                 315                 320

Phe Leu Val Met His Gly Thr Ala Asp Thr Val Thr Asp Pro Lys Gly
                325                 330                 335

Thr Gln Lys Leu Tyr Asn Glu Ala Ser Ser Ser Asp Lys Ser Ile Lys
```

```
              340                 345                 350
Leu Tyr Asp Gly Leu Leu His Asp Leu Leu Phe Glu Pro Glu Arg Glu
          355                 360                 365

Thr Ile Ala Gly Val Ile Leu Asp Trp Leu Asn Arg Arg Val
  370                 375                 380

<210> SEQ ID NO 27
<211> LENGTH: 3007
<212> TYPE: DNA
<213> ORGANISM: Arabidopsis thaliana

<400> SEQUENCE: 27
atgactataa aaacaccggg aactccggtt tcgaagatgg acagaacacc agctgtaaca     60
ccaggtggaa gctcaagatc cagggaagag aagattgttg ttactgtaag gttaaggcca    120
atgaataaga gagaactgtt agctaaagac caagttgctt gggaatgtgt aaatgaccac    180
accattgtgt ctaaaccaca agttcaagaa cgtttgcatc atcagtcctc atttacattt    240
gataaagttt ttggaccaga gagtttaaca gagaatgtgt atgaagatgg tgttaagaat    300
gttgcattgt ctgctttgat ggcataaat gcaacaatat ttgcatatgg acaaacaagc    360
agtggaaaga catataccat gagaggagta acggagaaag ctgtcaatga tatttacaat    420
cacataatta gacccctga aagagatttt actatcaaga tttctggtct ggaaatatat    480
aatgaaaatg tcagagatct gctcaattca gattcgggac gtgcccttaa actccttgat    540
gatccagaga aggtactgt ggttgaaaaa ctggttgaag aaacagctaa taacgataac    600
catttgcggc atctgattag catttgtgaa gctcaaagac aagttggaga aactgctttg    660
aatgatacta gctcgcggtc acaccaaata atcagactga caatacaaag tactcaccgc    720
gaaaattcag attgtgtgag gtcatatatg gctagtctga actttgtgga cttagcagga    780
agcgaaagag catcacaatc gcaggcagat ggaacgagac tcaggaagg ttgtcatatc    840 aatctaagtc taatgacact tacaactgtc ataaggaaat taagtgtggg aaaagaagc    900 ggccatatac cttacagaga ctccaagctt actaggattt tacagcattc actaggtggg    960
aatgctcgaa cagccattat atgtacattg agtccagctt ggctcatgt tgaacaatca   1020 agaaatactc tatacttcgc caaccgagcc aaggaagtta caaacaatgc ccacgtgaac   1080
atggttgtct ctgataagca actagtgaaa catcttcaga agaagtggc tagattggag   1140 gccgagcgtc gcacccctgg tccatcgaca gaaaaggatt tcaagatcca gcagatggaa   1200
atggaaatcg agagcttag aagacaaaga gatgatgcac aaattcaact tgaggagtta   1260
cgccaaaagc ttcaagggga tcagcaacaa aataagggct taaatccttt tgaatctcca   1320
gacccaccgg tcagaaaatg tctttcctat tctgttgccg taacgcctag ctcggagaac   1380
aaaacgctaa accggaatga gagagcaaga aagactacga tgcgccaatc tatgatacgg   1440
caatcatcaa ctgctccatt tacattgatg catgaaatcc gcaaactcga cacccttcaa   1500
gaacagttag gggaggaagc aacgaaagcc cttgaagtgt acaaaagga agtagcttgc   1560 catagactag ggaatcaaga tgcagctcag acgatagcta agcttcaagc agagataagg   1620
gaaatgcgta ctgttaaacc atctgcaatg cttaaagagg ttggagatgt catagctcct   1680
aacaagagcg taagtgccaa tctcaaggaa gagataacaa ggctccattc acaaggaagc   1740
accattgcga atctagagga gcaacttgag agcgttcaga agtcaataga taagttggtg   1800
atgtctcttc cgagcaatat cagtgctgga gatgagactc caaagacaaa gaatcatcat   1860
catcaatcaa agaagaagaa gcttcttcct ctgacaccaa gcagcgcatc caaccgccag   1920
```

-continued

```
aacttcttga aatctccatg ctctccgctt tcagcttcta ggcaagtctt ggattgtgat    1980
gctgagaaca aagctcctca agaaaacaac agttctgcag ctagaggggc gacgacacca    2040
caggggtctg agaaagagac tccacagaaa ggagaagaaa gcggagatgt ctcgtcaaga    2100
gaaggtactc caggctacag aagatcaagc tcagtgaaca tgaagaaaat gcagcaaatg    2160
tttcaaaacg cagcagagga gaatgtaaga agcataagag catacgtaac cgaactcaaa    2220
gaacgagtag ctaaactaca gtaccagaaa caacttctcg tttgtcaggt gcttgagttg    2280
gaagcaaatg atggagctgg atatagtgta gagaacgagg agaacgat aatggaagat     2340
gaagagcaga atcaagtggc gtggcatata actttcatag gaaaagaca acagatcata     2400
gagctgtggc atgtctgcca tgtctccata atccacagga cacaattcta cctactgttc    2460
aaaggtgacc aagccgatca aatctacatg gaagtcgagc taagacggtt aacttggtta    2520
gaacaacatc tagcagaagt aggaaacgca actccagctc gaaactgcga tgaatctgtg    2580
gtttctctat catcaagtat aaaagcattg agaagagagc gagagttttt ggcgaaaagg    2640
gttaactcga gattgacgcc tgaggagaga gaggagctgt atatgaaatg ggatgtgcca    2700
ttggaaggga aacagaggaa acttcagttc gtgaacaagc tatggactga tccttatgat    2760
tcaaggcacg tgcaagagag tgcagagata gttgcgaagc tagttggatt ctgtgaaagt    2820
ggcaacatct ctaaagagat gtttgagctc aatttcgcag tgccttcaga taaaagacag    2880
tggaacattg gttgggacaa catctctaat cttcttcacc tatgaagact tattgtgtgt    2940
ttatgatttg taaagtaca cgacacttct ttgtctcctc tgaatttgat taaataagct     3000
ttaccag                                                             3007
```

<210> SEQ ID NO 28
<211> LENGTH: 974
<212> TYPE: PRT
<213> ORGANISM: Arabidopsis thaliana

<400> SEQUENCE: 28

```
Met Thr Ile Lys Thr Pro Gly Thr Pro Val Ser Lys Met Asp Arg Thr
1               5                   10                  15

Pro Ala Val Thr Pro Gly Gly Ser Ser Arg Ser Arg Glu Glu Lys Ile
            20                  25                  30

Val Val Thr Val Arg Leu Arg Pro Met Asn Lys Arg Glu Leu Leu Ala
        35                  40                  45

Lys Asp Gln Val Ala Trp Glu Cys Val Asn Asp His Thr Ile Val Ser
    50                  55                  60

Lys Pro Gln Val Gln Glu Arg Leu His His Gln Ser Ser Phe Thr Phe
65                  70                  75                  80

Asp Lys Val Phe Gly Pro Glu Ser Leu Thr Glu Asn Val Tyr Glu Asp
                85                  90                  95

Gly Val Lys Asn Val Ala Leu Ser Ala Leu Met Gly Ile Asn Ala Thr
            100                 105                 110

Ile Phe Ala Tyr Gly Gln Thr Ser Ser Gly Lys Thr Tyr Thr Met Arg
        115                 120                 125

Gly Val Thr Glu Lys Ala Val Asn Asp Ile Tyr Asn His Ile Ile Lys
    130                 135                 140

Thr Pro Glu Arg Asp Phe Thr Ile Lys Ile Ser Gly Leu Glu Ile Tyr
145                 150                 155                 160

Asn Glu Asn Val Arg Asp Leu Leu Asn Ser Asp Ser Gly Arg Ala Leu
                165                 170                 175

Lys Leu Leu Asp Asp Pro Glu Lys Gly Thr Val Val Glu Lys Leu Val
```

```
                    180                 185                 190
Glu Glu Thr Ala Asn Asn Asp Asn His Leu Arg His Leu Ile Ser Ile
                195                 200                 205
Cys Glu Ala Gln Arg Gln Val Gly Glu Thr Ala Leu Asn Asp Thr Ser
            210                 215                 220
Ser Arg Ser His Gln Ile Ile Arg Leu Thr Ile Gln Ser Thr His Arg
225                 230                 235                 240
Glu Asn Ser Asp Cys Val Arg Ser Tyr Met Ala Ser Leu Asn Phe Val
                245                 250                 255
Asp Leu Ala Gly Ser Glu Arg Ala Ser Gln Ser Gln Ala Asp Gly Thr
            260                 265                 270
Arg Leu Arg Glu Gly Cys His Ile Asn Leu Ser Leu Met Thr Leu Thr
        275                 280                 285
Thr Val Ile Arg Lys Leu Ser Val Gly Lys Arg Ser Gly His Ile Pro
    290                 295                 300
Tyr Arg Asp Ser Lys Leu Thr Arg Ile Leu Gln His Ser Leu Gly Gly
305                 310                 315                 320
Asn Ala Arg Thr Ala Ile Ile Cys Thr Leu Ser Pro Ala Leu Ala His
                325                 330                 335
Val Glu Gln Ser Arg Asn Thr Leu Tyr Phe Ala Asn Arg Ala Lys Glu
            340                 345                 350
Val Thr Asn Asn Ala His Val Asn Met Val Val Ser Asp Lys Gln Leu
        355                 360                 365
Val Lys His Leu Gln Lys Glu Val Ala Arg Leu Glu Ala Glu Arg Arg
    370                 375                 380
Thr Pro Gly Pro Ser Thr Glu Lys Asp Phe Lys Ile Gln Gln Met Glu
385                 390                 395                 400
Met Glu Ile Gly Glu Leu Arg Arg Gln Arg Asp Asp Ala Gln Ile Gln
                405                 410                 415
Leu Glu Glu Leu Arg Gln Lys Leu Gln Gly Asp Gln Gln Asn Lys
            420                 425                 430
Gly Leu Asn Pro Phe Glu Ser Pro Asp Pro Val Arg Lys Cys Leu
        435                 440                 445
Ser Tyr Ser Val Ala Val Thr Pro Ser Ser Glu Asn Lys Thr Leu Asn
    450                 455                 460
Arg Asn Glu Arg Ala Arg Lys Thr Thr Met Arg Gln Ser Met Ile Arg
465                 470                 475                 480
Gln Ser Ser Thr Ala Pro Phe Thr Leu Met His Glu Ile Arg Lys Leu
                485                 490                 495
Glu His Leu Gln Glu Gln Leu Gly Glu Glu Ala Thr Lys Ala Leu Glu
            500                 505                 510
Val Leu Gln Lys Glu Val Ala Cys His Arg Leu Gly Asn Gln Asp Ala
        515                 520                 525
Ala Gln Thr Ile Ala Lys Leu Gln Ala Glu Ile Arg Glu Met Arg Thr
    530                 535                 540
Val Lys Pro Ser Ala Met Leu Lys Glu Val Gly Asp Val Ile Ala Pro
545                 550                 555                 560
Asn Lys Ser Val Ser Ala Asn Leu Lys Glu Glu Ile Thr Arg Leu His
                565                 570                 575
Ser Gln Gly Ser Thr Ile Ala Asn Leu Glu Glu Gln Leu Glu Ser Val
            580                 585                 590
Gln Lys Ser Ile Asp Lys Leu Val Met Ser Leu Pro Ser Asn Ile Ser
        595                 600                 605
```

| Ala | Gly | Asp | Glu | Thr | Pro | Lys | Thr | Lys | Asn | His | His | Gln | Ser | Lys |
|---|---|---|---|---|---|---|---|---|---|---|---|---|---|---|
| 610 | | | | | 615 | | | | | 620 | | | | |

Lys Lys Lys Leu Leu Pro Leu Thr Pro Ser Ser Ala Ser Asn Arg Gln
625             630             635             640

Asn Phe Leu Lys Ser Pro Cys Ser Pro Leu Ser Ala Ser Arg Gln Val
            645             650             655

Leu Asp Cys Asp Ala Glu Asn Lys Ala Pro Gln Glu Asn Asn Ser Ser
        660             665             670

Ala Ala Arg Gly Ala Thr Thr Pro Gln Gly Ser Glu Lys Glu Thr Pro
    675             680             685

Gln Lys Gly Glu Glu Ser Gly Asp Val Ser Ser Arg Glu Gly Thr Pro
690             695             700

Gly Tyr Arg Arg Ser Ser Ser Val Asn Met Lys Lys Met Gln Gln Met
705             710             715             720

Phe Gln Asn Ala Ala Glu Glu Asn Val Arg Ser Ile Arg Ala Tyr Val
            725             730             735

Thr Glu Leu Lys Glu Arg Val Ala Lys Leu Gln Tyr Gln Lys Gln Leu
        740             745             750

Leu Val Cys Gln Val Leu Glu Leu Glu Ala Asn Asp Gly Ala Gly Tyr
    755             760             765

Ser Val Glu Asn Glu Glu Asn Thr Ile Met Glu Asp Glu Glu Gln Asn
770             775             780

Gln Val Ala Trp His Ile Thr Phe Ile Glu Glu Arg Gln Gln Ile Ile
785             790             795             800

Glu Leu Trp His Val Cys His Val Ser Ile Ile His Arg Thr Gln Phe
            805             810             815

Tyr Leu Leu Phe Lys Gly Asp Gln Ala Asp Gln Ile Tyr Met Glu Val
        820             825             830

Glu Leu Arg Arg Leu Thr Trp Leu Glu Gln His Leu Ala Glu Val Gly
    835             840             845

Asn Ala Thr Pro Ala Arg Asn Cys Asp Glu Ser Val Val Ser Leu Ser
850             855             860

Ser Ser Ile Lys Ala Leu Arg Arg Glu Arg Glu Phe Leu Ala Lys Arg
865             870             875             880

Val Asn Ser Arg Leu Thr Pro Glu Glu Arg Glu Glu Leu Tyr Met Lys
            885             890             895

Trp Asp Val Pro Leu Glu Gly Lys Gln Arg Lys Leu Gln Phe Val Asn
        900             905             910

Lys Leu Trp Thr Asp Pro Tyr Asp Ser Arg His Val Gln Glu Ser Ala
    915             920             925

Glu Ile Val Ala Lys Leu Val Gly Phe Cys Gly Ser Gly Asn Ile Ser
930             935             940

Lys Glu Met Phe Glu Leu Asn Phe Ala Val Pro Ser Asp Lys Arg Gln
945             950             955             960

Trp Asn Ile Gly Trp Asp Asn Ile Ser Asn Leu Leu His Leu
            965             970

<210> SEQ ID NO 29
<211> LENGTH: 753
<212> TYPE: DNA
<213> ORGANISM: Arabidopsis thaliana

<400> SEQUENCE: 29
atgtccatct ttttttctct catcagcttc gtcgtcttct ccgtcgctga cctcccgtcg     60
tgcttctcag ccgatcaaca gtacgaggag tgtcgctcac gtaatctgac atgtggatct    120

```
ggacacaggg tattcgagag taccacgtat ccgttctggg gtggattcaa taaacccaaa      180
ttctgcggtc attcgtcatt caaactctcc tgcgagggtg atcaaaacct aaccctagcg      240
atcgggaaca tcactcttcg cgttgtttct gcgaatctgg aggatcataa aatttccgtt      300
gccgatgata gtctactaga cggaggttgc ctaaacattt ggaacttcaa cgggaagaat      360
cagttcacat tagactccaa caccgagacg atcgatgtat tcgtcaactg ttccggcgta      420
gctccgttgc agatttcttg cgaagaaagc tacgaggatc cggtgacata tcatgtcttg      480
cgatcgtcgg attctgacga aggttgtatg aaatatgcag aaattccgat gctgaggtct      540
gctaaggacg agcttcaacg gtccgaacta acttttgtgg aagctttgag aaaaggattc      600
gatttgaggt acatcatgga agacaaagct tgccggagat gcattgattc cggtgggatt      660
tgtggttcgg cgttagattc ggagagtttc cggtgtctat gtgcggacag acctcacaac      720
tcctcctgcg acgataacac taaccaaggt tag                                   753

<210> SEQ ID NO 30
<211> LENGTH: 250
<212> TYPE: PRT
<213> ORGANISM: Arabidopsis thaliana

<400> SEQUENCE: 30

Met Ser Ile Phe Phe Phe Phe Ile Ser Phe Val Val Phe Ser Val Ala
 1               5                  10                  15

Asp Leu Pro Ser Cys Phe Ser Ala Asp Gln Gln Tyr Glu Glu Cys Arg
            20                  25                  30

Ser Arg Asn Leu Thr Cys Gly Ser Gly His Arg Val Phe Glu Ser Thr
        35                  40                  45

Thr Tyr Pro Phe Trp Gly Gly Phe Asn Lys Pro Lys Phe Cys Gly His
    50                  55                  60

Ser Ser Phe Lys Leu Ser Cys Glu Gly Asp Gln Asn Leu Thr Leu Ala
65                  70                  75                  80

Ile Gly Asn Ile Thr Leu Arg Val Val Ser Ala Asn Leu Glu Asp His
                85                  90                  95

Lys Ile Ser Val Ala Asp Asp Ser Leu Leu Asp Gly Gly Cys Leu Asn
            100                 105                 110

Ile Trp Asn Phe Asn Gly Lys Asn Gln Phe Thr Leu Asp Ser Asn Thr
        115                 120                 125

Glu Thr Ile Asp Val Phe Val Asn Cys Ser Gly Val Ala Pro Leu Gln
    130                 135                 140

Ile Ser Cys Glu Glu Ser Tyr Glu Asp Pro Val Thr Tyr His Val Leu
145                 150                 155                 160

Arg Ser Ser Asp Ser Asp Glu Gly Cys Met Lys Tyr Ala Glu Ile Pro
                165                 170                 175

Met Leu Arg Ser Ala Lys Asp Glu Leu Gln Arg Ser Glu Leu Thr Phe
            180                 185                 190

Val Glu Ala Leu Arg Lys Gly Phe Asp Leu Arg Tyr Ile Met Glu Asp
        195                 200                 205

Lys Ala Cys Arg Arg Cys Ile Asp Ser Gly Gly Ile Cys Gly Ser Ala
    210                 215                 220

Leu Asp Ser Glu Ser Phe Arg Cys Leu Cys Ala Asp Arg Pro His Asn
225                 230                 235                 240

Ser Ser Cys Asp Asp Asn Thr Asn Gln Gly
                245                 250
```

```
<210> SEQ ID NO 31
<211> LENGTH: 1818
<212> TYPE: DNA
<213> ORGANISM: Arabidopsis thaliana

<400> SEQUENCE: 31
atgaatcctt caactccaag tttactctac acatccatct tcttctactt cacaataata      60
gcaactcaaa ccctctctct tgatccaaag ttcaaggctt gtgagccgaa atcatgcggc     120
aaaggtcccc agatctccta tccattttat ctatctggaa agcaagaatc tttttgtggt     180
tatccaagtt ttgaactcac ttgtgatgat gaagaaaagc tccctgttct cgggatctcc     240
ggtgaggaat atgtcatcaa gacatatct tacttaacac agtcgtttca ggtcgtgaac     300
tcaaaggctt ctcatgatcc atgtcccaga ccgctgaaca atcttaccct ccataggact     360
cctttctttg tgaacccttc tcatatcaac ttcactatac tttacaattg ttccgatcac     420
ctgctggagg attttaggac ataccctctt acttgtgctc gaaacacgag tcttcttcga     480
tcttttgggg tctttgacag aaagaaactt ggaaaagaga acaaattgc atccatgtcg     540 tgccagaaac tagtggatgt tcctgtttta gctagtaatg agtctgatgt gatgggtatg     600
acttatgttg agattttgaa gagggggtttt gttctgaatt ggactgcaaa cagttgcttc     660
cgctgcatca ccagcggcgg gagatgtgga actgatcaac aagaattcgt atgcttgtgt     720
cctgatggac ctaaacttca tgatacttgc acgaatgcat tgcttccaag aaacatctca     780
tcagatccat ctgcaaagtc ttttgacatc gagaaagcag aggaattatt agtcggagtt     840 catatttttct cttacgaaga acttgaagaa gccactaata acttcgaccc atctaaagaa     900
ctcggtgatg gaggctttgg tactgtctat tacggtaagc ttaaagatgg acgaagcgta     960
gccgttaaac ggttatacga taacaacttc aaaagagcag agcaattcag gaatgaagtt    1020
gagatcttaa cgggtttacg ccatccaaac ctcgtggctc tctttggatg ctcctcaaaa    1080
cagagccggg acttactgct agtgtatgag tatgttgcaa acggcacgtt agctgatcat    1140
ctacatggtc acaggcaaa ccctagctca cttccttggt ctattcggct caaaatcgct    1200
gttgaaactg cctctgcctt gaagtatctc cacgcctcca agatcatcca ccgtgatgtt    1260
aaatccaaca acatccttct cgaccaaaac ttcaatgtca aggttgcgga ttttggactc    1320
tctagactgt ttcctatgga taaaacgcac gtatctaccg ctccacaagg aactccggga    1380
tatgtcgacc cggattacca cttatgctat caactctcaa acaaaagcga cgtgtacagc    1440
tttgcggtag tgttaatgga gcttatctct tcacttccag cagtcgacat cacaagaccg    1500
cgccaagaga tcaacctctc gaacatggca gtcgttaaaa tccagaacca cgagctccgc    1560
gacatggtgg atccgtcact tgggtttgac acggatacaa gagtgagaca gacggtgatc    1620
gctgtcgctg agctggcgtt ccaatgcttg cagtcggata agatcttag gccatgtatg    1680 tcgcacgtgc aggatacgtt gacgaggata cagaacaatg gatttggttc ggaaatggat    1740
gttgtagatg tgaacaagag tggaccgttg gttgcacagt ctccagatag tgtcattgtg    1800
aaatgggaca gtaagtaa                                                  1818

<210> SEQ ID NO 32
<211> LENGTH: 605
<212> TYPE: PRT
<213> ORGANISM: Arabidopsis thaliana

<400> SEQUENCE: 32

Met Asn Pro Ser Thr Pro Ser Leu Leu Tyr Thr Ser Ile Phe Phe Tyr
1               5                   10                  15
```

-continued

```
Phe Thr Ile Ile Ala Thr Gln Thr Leu Ser Leu Asp Pro Lys Phe Lys
             20                  25                  30

Ala Cys Glu Pro Lys Ser Cys Lys Gly Pro Gln Ile Ser Tyr Pro
         35                  40                  45

Phe Tyr Leu Ser Gly Lys Gln Glu Ser Phe Cys Gly Tyr Pro Ser Phe
 50                  55                  60

Glu Leu Thr Cys Asp Asp Glu Lys Leu Pro Val Leu Gly Ile Ser
 65              70                  75                  80

Gly Glu Glu Tyr Val Ile Lys Asn Ile Ser Tyr Leu Thr Gln Ser Phe
                 85                  90                  95

Gln Val Val Asn Ser Lys Ala Ser His Asp Pro Cys Pro Arg Pro Leu
             100                 105                 110

Asn Asn Leu Thr Leu His Arg Thr Pro Phe Phe Val Asn Pro Ser His
             115                 120                 125

Ile Asn Phe Thr Ile Leu Tyr Asn Cys Ser Asp His Leu Leu Glu Asp
 130                 135                 140

Phe Arg Thr Tyr Pro Leu Thr Cys Ala Arg Asn Thr Ser Leu Leu Arg
145                 150                 155                 160

Ser Phe Gly Val Phe Asp Arg Lys Lys Leu Gly Lys Glu Lys Gln Ile
                 165                 170                 175

Ala Ser Met Ser Cys Gln Lys Leu Val Asp Val Pro Val Leu Ala Ser
             180                 185                 190

Asn Glu Ser Asp Val Met Gly Met Thr Tyr Val Glu Ile Leu Lys Arg
             195                 200                 205

Gly Phe Val Leu Asn Trp Thr Ala Asn Ser Cys Phe Arg Cys Ile Thr
 210                 215                 220

Ser Gly Gly Arg Cys Gly Thr Asp Gln Gln Glu Phe Val Cys Leu Cys
225                 230                 235                 240

Pro Asp Gly Pro Lys Leu His Asp Thr Cys Thr Asn Ala Leu Leu Pro
                 245                 250                 255

Arg Asn Ile Ser Ser Asp Pro Ser Ala Lys Ser Phe Asp Ile Glu Lys
             260                 265                 270

Ala Glu Glu Leu Leu Val Gly Val His Ile Phe Ser Tyr Glu Glu Leu
             275                 280                 285

Glu Glu Ala Thr Asn Asn Phe Asp Pro Ser Lys Glu Leu Gly Asp Gly
 290                 295                 300

Gly Phe Gly Thr Val Tyr Tyr Gly Lys Leu Lys Asp Gly Arg Ser Val
305                 310                 315                 320

Ala Val Lys Arg Leu Tyr Asp Asn Asn Phe Lys Arg Ala Glu Gln Phe
                 325                 330                 335

Arg Asn Glu Val Glu Ile Leu Thr Gly Leu Arg His Pro Asn Leu Val
             340                 345                 350

Ala Leu Phe Gly Cys Ser Ser Lys Gln Ser Arg Asp Leu Leu Leu Val
             355                 360                 365

Tyr Glu Tyr Val Ala Asn Gly Thr Leu Ala Asp His Leu His Gly Pro
 370                 375                 380

Gln Ala Asn Pro Ser Ser Leu Pro Trp Ser Ile Arg Leu Lys Ile Ala
385                 390                 395                 400

Val Glu Thr Ala Ser Ala Leu Lys Tyr Leu His Ala Ser Lys Ile Ile
                 405                 410                 415

His Arg Asp Val Lys Ser Asn Asn Ile Leu Leu Asp Gln Asn Phe Asn
             420                 425                 430

Val Lys Val Ala Asp Phe Gly Leu Ser Arg Leu Phe Pro Met Asp Lys
             435                 440                 445
```

```
Thr His Val Ser Thr Ala Pro Gln Gly Thr Pro Gly Tyr Val Asp Pro
    450                 455                 460

Asp Tyr His Leu Cys Tyr Gln Leu Ser Asn Lys Ser Asp Val Tyr Ser
465                 470                 475                 480

Phe Ala Val Val Leu Met Glu Leu Ile Ser Ser Leu Pro Ala Val Asp
                485                 490                 495

Ile Thr Arg Pro Arg Gln Glu Ile Asn Leu Ser Asn Met Ala Val Val
            500                 505                 510

Lys Ile Gln Asn His Glu Leu Arg Asp Met Val Asp Pro Ser Leu Gly
        515                 520                 525

Phe Asp Thr Asp Thr Arg Val Arg Gln Thr Val Ile Ala Val Ala Glu
    530                 535                 540

Leu Ala Phe Gln Cys Leu Gln Ser Asp Lys Asp Leu Arg Pro Cys Met
545                 550                 555                 560

Ser His Val Gln Asp Thr Leu Thr Arg Ile Gln Asn Asn Gly Phe Gly
                565                 570                 575

Ser Glu Met Asp Val Val Asp Val Asn Lys Ser Gly Pro Leu Val Ala
            580                 585                 590

Gln Ser Pro Asp Ser Val Ile Val Lys Trp Asp Ser Lys
        595                 600                 605

<210> SEQ ID NO 33
<211> LENGTH: 1016
<212> TYPE: DNA
<213> ORGANISM: Arabidopsis thaliana

<400> SEQUENCE: 33
aaagaagttg tcagaaaaaa aaaaaaaaaa aagtgtcaag aagatcatat ctcaattcat      60
tatattatgg caaatttcga gaatctttct tctgattttc agacaatagc catggatata     120
tattcttcca taactcaagc tgcagatcta acaacaaca acagtaacct tcattttcaa     180
acatttcatc cttcctctac ttctctcgaa tcgctcttcc ttcatcatca tcaacaacaa     240
ttacttcact ttcccggaaa ctctccagac agtagtaaca atttctcttc aacttcaagt     300
ttcctccata gtgatcacaa catcgtcgat gagaccaaga agagaaaagc tttgttacct     360
actttgtctt catcagagac tagcggcgtc tccgataata cgaatgttat tgccactgaa     420
acaggttctt tgagaagagg taagaggttg aagaagaaga aggaagaaga agacgagaaa     480
gagagagaag ttgttcatgt gagagccaga agaggccaag ccactgatag ccacagctta     540
gcagaacggg ttcggcgagg gaaaataaac gagagattaa gatgcttgca agatatggtg     600
cccggatgtt ataaggctat gggaatggct acgatgcttg acgagataat taattatgtc     660
cagtctctac agaatcaagt cgagttcctc tcgatgaaac tcactgcagc aagttcgttt     720
tatgacttta actcagagac agatgcagtt gattccatgc agagagcaaa ggcacgtgag     780
acagtggaga tggggagaca aacaagagat gggagtcctg tcttccattt atcaacatgg     840
tcccttttgac ttttgttttc tcttttctct tttccttctt ttttattgtt ttcgaaatta     900
ttcttctatt tatttggatg cgatatgtca tatatacgac ccaacttggg ataatatttg     960
taatctgtat acttgtaatt tcgacgatat aaatttattg gtgacttata attgtc          1016

<210> SEQ ID NO 34
<211> LENGTH: 260
<212> TYPE: PRT
<213> ORGANISM: Arabidopsis thaliana

<400> SEQUENCE: 34
```

Met Ala Asn Phe Glu Asn Leu Ser Ser Asp Phe Gln Thr Ile Ala Met
1               5                   10                  15

Asp Ile Tyr Ser Ser Ile Thr Gln Ala Ala Asp Leu Asn Asn Asn Asn
            20                  25                  30

Ser Asn Leu His Phe Gln Thr Phe His Pro Ser Ser Thr Ser Leu Glu
        35                  40                  45

Ser Leu Phe Leu His His His Gln Gln Gln Leu Leu His Phe Pro Gly
    50                  55                  60

Asn Ser Pro Asp Ser Ser Asn Asn Phe Ser Ser Thr Ser Ser Phe Leu
65              70                  75                  80

His Ser Asp His Asn Ile Val Asp Glu Thr Lys Lys Arg Lys Ala Leu
                85                  90                  95

Leu Pro Thr Leu Ser Ser Ser Glu Thr Ser Gly Val Ser Asp Asn Thr
            100                 105                 110

Asn Val Ile Ala Thr Glu Thr Gly Ser Leu Arg Arg Gly Lys Arg Leu
        115                 120                 125

Lys Lys Lys Lys Glu Glu Glu Asp Glu Lys Glu Arg Glu Val Val His
    130                 135                 140

Val Arg Ala Arg Arg Gly Gln Ala Thr Asp Ser His Ser Leu Ala Glu
145                 150                 155                 160

Arg Val Arg Arg Gly Lys Ile Asn Glu Arg Leu Arg Cys Leu Gln Asp
                165                 170                 175

Met Val Pro Gly Cys Tyr Lys Ala Met Gly Met Ala Thr Met Leu Asp
            180                 185                 190

Glu Ile Ile Asn Tyr Val Gln Ser Leu Gln Asn Gln Val Glu Phe Leu
        195                 200                 205

Ser Met Lys Leu Thr Ala Ala Ser Ser Phe Tyr Asp Phe Asn Ser Glu
    210                 215                 220

Thr Asp Ala Val Asp Ser Met Gln Arg Ala Lys Ala Arg Glu Thr Val
225                 230                 235                 240

Glu Met Gly Arg Gln Thr Arg Asp Gly Ser Pro Val Phe His Leu Ser
                245                 250                 255

Thr Trp Ser Leu
            260

<210> SEQ ID NO 35
<211> LENGTH: 2352
<212> TYPE: DNA
<213> ORGANISM: Arabidopsis thaliana

<400> SEQUENCE: 35
atgtggaaca acctgactgg gcgtattccg ttggagatag aagaatttc ttccttgaaa      60 ctcctactgt tgaatgggaa caagttcacg ggtagtttac ccctgaact tggtaacctt     120 caaaacctaa acaggcttca agtagatgag ataacataa caggttcagt tccattttca     180
tttggaaact tgagaagcat aaaacatctc cacttaaaca ataacacgat aagtggagaa     240
attcctgttg agctatccaa attgcccaag cttgttcaca tgatactgga caacaataac     300
ttgactggga cattgccgct agagttagct caattgccat ccttgaccat acttcagctg     360
gataacaaca acttcgaagg ttcaactatt ccagaggctt acggacactt ttctagatta     420
gtaaaattaa gtttaaggaa ctgtggactg caaggatcta ttcctgattt aagcaggata     480
gaaaatctta gctatctaga cctaagttgg aaccacctca caggcactat accagaatcc     540
aagctttctg acaatatgac aacaattgaa ctatcttata ccacctaac tggatctata      600

```
ccacaaagtt tctcagattt gaactctctt caattactgt cacttgagaa caacagttta    660
tctggttctg tcccaacaga aatttggcag gacaagtctt tcgagaataa caagctgcaa    720
gttgatctca ggaacaacaa cttctctgat gccacaggaa acctgagaac accagacaat    780
aatgtgaaag tatccccagg aatctgcttg tgcacagcac ctctttcgat tgattatagg    840
ctaaagagcc ctagcttctt tttctttact ccatatattg aacgccaatt cagggagtat    900
attacctcgt ccctccaact ggagactcat caactagcga ttgatagact tgtcgatgag    960
aacaggctgc gtccaagaat gtacttaaag ctagtcccca aaggcagaat aacatttaac   1020
aagagtgaag tcatacgtat acgggacagg tttatgtcat ggagttttaa taaaactgac   1080
ttttttggac catatgagct gctggacttc cctcttcaag gaccgtatgg ctctgtcgtc   1140
gctgccactg ttttatcagt gactgcaaca cttctatatg ttaggaaacg tcgtgaaaac   1200
tcacatacgc tcaccaaaaa acgtgttttc agaacaatat ctcgggaaat caaaggggtg   1260
aagaagttca gttttgtaga actgtcggat gcaactaatg ttttgacag ctccacactg    1320
attggtagag gtagctatgg aaaggtctac aaaggcattt tgtcaaataa aaccgaagtt   1380
gccatcaaac gaggagaaga aacttctctg cagagcgaaa aagagtttct gaatgagatc   1440
gatctacttt cgaggttaca tcaccggaat cttgtgtcgc ttattggcta cagtagtgac   1500
atcggggaac agatgctggt atatgagtat atgcctaatg gaaatgtgcg tgattggctt   1560
tcagtggttt tacattgtca cgcagctaat gctgcagaca cattgagctt agcatgagg   1620
tcacatgtgg cgttaggttc agctaaaggg attctttacc ttcacactga agcaaatccg   1680
ccagttattc accgcgatat caaaaccagc aacatactct tggactgtca gcttcatgct   1740
aaggttgctg attttggatt gtcacggttg gctcctgctt ttggggaggg agatggtgag   1800
cccgcccatg tatcaacagt agtaagagga acaccgggat atctggatcc agagtatttc   1860
atgactcagc aattgacggt gagaagtgat gtgtacagct ttggagtagt gttgcttgag   1920
cttttgactg gaatgcaccc attctttgag ggtacacata ttatccgcga ggtactttc    1980
ttgactgagc tcccacgtag atctgataat ggagtagcta atctgtgag gaccgcgaat    2040
gaatgtggaa cggttttgtc agtggcggat agtcggatgg gacaatgttc gcccgataaa   2100
gtgaagaagt tggcggaatt agctttatgg tgttgtgaag atagaccaga gacgagacca   2160
ccaatgtcaa aagtggtgaa agaacttgaa ggtatttgcc aatctgtgcg agaacccgaa   2220
atgttctcag aaacaacgaa attactctgc tccaaaacat cgccgtcatc ttcttctgta   2280
ccctcgccat tgtctttact tcctggaagt aacttggaca gtggcttttt ccacgctgta   2340
aaacctcgtt ga                                                       2352
```

<210> SEQ ID NO 36
<211> LENGTH: 783
<212> TYPE: PRT
<213> ORGANISM: Arabidopsis thaliana

<400> SEQUENCE: 36

Met Trp Asn Asn Leu Thr Gly Arg Ile Pro Leu Glu Ile Gly Arg Ile
1               5                   10                  15

Ser Ser Leu Lys Leu Leu Leu Asn Gly Asn Lys Phe Thr Gly Ser
            20                  25                  30

Leu Pro Pro Glu Leu Gly Asn Leu Gln Asn Leu Asn Arg Leu Gln Val
        35                  40                  45

Asp Glu Asn Asn Ile Thr Gly Ser Val Pro Phe Ser Phe Gly Asn Leu
    50                  55                  60

-continued

Arg Ser Ile Lys His Leu His Leu Asn Asn Asn Thr Ile Ser Gly Glu
65                  70                  75                  80

Ile Pro Val Glu Leu Ser Lys Leu Pro Lys Leu Val His Met Ile Leu
            85                  90                  95

Asp Asn Asn Leu Thr Gly Thr Leu Pro Leu Glu Leu Ala Gln Leu
            100                 105                 110

Pro Ser Leu Thr Ile Leu Gln Leu Asp Asn Asn Asn Phe Glu Gly Ser
        115                 120                 125

Thr Ile Pro Glu Ala Tyr Gly His Phe Ser Arg Leu Val Lys Leu Ser
        130                 135                 140

Leu Arg Asn Cys Gly Leu Gln Gly Ser Ile Pro Asp Leu Ser Arg Ile
145                 150                 155                 160

Glu Asn Leu Ser Tyr Leu Asp Leu Ser Trp Asn His Leu Thr Gly Thr
                165                 170                 175

Ile Pro Glu Ser Lys Leu Ser Asp Asn Met Thr Thr Ile Glu Leu Ser
            180                 185                 190

Tyr Asn His Leu Thr Gly Ser Ile Pro Gln Ser Phe Ser Asp Leu Asn
        195                 200                 205

Ser Leu Gln Leu Leu Ser Leu Glu Asn Asn Ser Leu Ser Gly Ser Val
210                 215                 220

Pro Thr Glu Ile Trp Gln Asp Lys Ser Phe Glu Asn Asn Lys Leu Gln
225                 230                 235                 240

Val Asp Leu Arg Asn Asn Asn Phe Ser Asp Ala Thr Gly Asn Leu Arg
                245                 250                 255

Thr Pro Asp Asn Asn Val Lys Val Ser Pro Gly Ile Cys Leu Cys Thr
            260                 265                 270

Ala Pro Leu Ser Ile Asp Tyr Arg Leu Lys Ser Pro Ser Phe Phe Phe
        275                 280                 285

Phe Thr Pro Tyr Ile Glu Arg Gln Phe Arg Glu Tyr Ile Thr Ser Ser
290                 295                 300

Leu Gln Leu Glu Thr His Gln Leu Ala Ile Asp Arg Leu Val Asp Glu
305                 310                 315                 320

Asn Arg Leu Arg Pro Arg Met Tyr Leu Lys Leu Val Pro Lys Gly Arg
                325                 330                 335

Ile Thr Phe Asn Lys Ser Glu Val Ile Arg Ile Arg Asp Arg Phe Met
            340                 345                 350

Ser Trp Ser Phe Asn Lys Thr Asp Phe Phe Gly Pro Tyr Glu Leu Leu
        355                 360                 365

Asp Phe Pro Leu Gln Gly Pro Tyr Gly Ser Val Val Ala Ala Thr Val
        370                 375                 380

Leu Ser Val Thr Ala Thr Leu Leu Tyr Val Arg Lys Arg Arg Glu Asn
385                 390                 395                 400

Ser His Thr Leu Thr Lys Lys Arg Val Phe Arg Thr Ile Ser Arg Glu
                405                 410                 415

Ile Lys Gly Val Lys Lys Phe Ser Phe Val Glu Leu Ser Asp Ala Thr
            420                 425                 430

Asn Gly Phe Asp Ser Ser Thr Leu Ile Gly Arg Gly Ser Tyr Gly Lys
        435                 440                 445

Val Tyr Lys Gly Ile Leu Ser Asn Lys Thr Glu Val Ala Ile Lys Arg
        450                 455                 460

Gly Glu Glu Thr Ser Leu Gln Ser Gly Lys Glu Phe Leu Asn Glu Ile
465                 470                 475                 480

Asp Leu Leu Ser Arg Leu His His Arg Asn Leu Val Ser Leu Ile Gly
                485                 490                 495

Tyr Ser Ser Asp Ile Gly Glu Gln Met Leu Val Tyr Glu Tyr Met Pro
            500                 505                 510
Asn Gly Asn Val Arg Asp Trp Leu Ser Val Val Leu His Cys His Ala
        515                 520                 525
Ala Asn Ala Ala Asp Thr Leu Ser Phe Ser Met Arg Ser His Val Ala
530                 535                 540
Leu Gly Ser Ala Lys Gly Ile Leu Tyr Leu His Thr Glu Ala Asn Pro
545                 550                 555                 560
Pro Val Ile His Arg Asp Ile Lys Thr Ser Asn Ile Leu Leu Asp Cys
                565                 570                 575
Gln Leu His Ala Lys Val Ala Asp Phe Gly Leu Ser Arg Leu Ala Pro
            580                 585                 590
Ala Phe Gly Glu Gly Asp Gly Glu Pro Ala His Val Ser Thr Val Val
        595                 600                 605
Arg Gly Thr Pro Gly Tyr Leu Asp Pro Glu Tyr Phe Met Thr Gln Gln
610                 615                 620
Leu Thr Val Arg Ser Asp Val Tyr Ser Phe Gly Val Val Leu Leu Glu
625                 630                 635                 640
Leu Leu Thr Gly Met His Pro Phe Phe Glu Gly Thr His Ile Ile Arg
                645                 650                 655
Glu Val Leu Phe Leu Thr Glu Leu Pro Arg Arg Ser Asp Asn Gly Val
            660                 665                 670
Ala Lys Ser Val Arg Thr Ala Asn Glu Cys Gly Thr Val Leu Ser Val
        675                 680                 685
Ala Asp Ser Arg Met Gly Gln Cys Ser Pro Asp Lys Val Lys Lys Leu
690                 695                 700
Ala Glu Leu Ala Leu Trp Cys Cys Glu Asp Arg Pro Gly Thr Arg Pro
705                 710                 715                 720
Pro Met Ser Lys Val Val Lys Glu Leu Glu Gly Ile Cys Gln Ser Val
                725                 730                 735
Arg Glu Pro Glu Met Phe Ser Glu Thr Thr Lys Leu Leu Cys Ser Lys
            740                 745                 750
Thr Ser Pro Ser Ser Ser Ser Val Pro Ser Pro Leu Ser Leu Leu Pro
        755                 760                 765
Gly Ser Asn Leu Asp Ser Gly Phe Phe His Ala Val Lys Pro Arg
770                 775                 780

<210> SEQ ID NO 37
<211> LENGTH: 528
<212> TYPE: DNA
<213> ORGANISM: Arabidopsis thaliana

<400> SEQUENCE: 37
atgaagagag accggtccga ttacgaagaa tccatgaagc atatagacat agtagaaagt    60
ctaatgatgt tatctcgaag tttcgtggtc aaacaaatcg atgtaaagca atctaccgga   120
agcaaaacga accataataa ccacttcgaa tgcaaaacgt gtaaccggaa atttgattcc   180
ttccaagctc ttggaggtca tagagctagc acaagaaaac ctaagctgat cgttgaccaa   240
gaacaggtga agcatcgtaa caaagagaat gatatgcata agtgtacaat ttgcgatcaa   300
atgtttggga ccggtcaagc tctaggcggt cacatgagaa agcataggac gagcatgata   360
accgagcaat cgattgtccc ttctgtggtt tattccagac cggttttTaa tcgttgcagt   420
agcagcaagg agatcttgga cttaaatcta actccattgg aaaatgatct tgtgttaatc   480
tttgggaaga atttggttcc acaaattgat ttgaagtttg tgaattag              528

<210> SEQ ID NO 38
<211> LENGTH: 175
<212> TYPE: PRT
<213> ORGANISM: Arabidopsis thaliana

<400> SEQUENCE: 38

```
Met Lys Arg Asp Arg Ser Asp Tyr Glu Glu Ser Met Lys His Ile Asp
1               5                   10                  15

Ile Val Glu Ser Leu Met Met Leu Ser Arg Ser Phe Val Val Lys Gln
            20                  25                  30

Ile Asp Val Lys Gln Ser Thr Gly Ser Lys Thr Asn His Asn Asn His
        35                  40                  45

Phe Glu Cys Lys Thr Cys Asn Arg Lys Phe Asp Ser Phe Gln Ala Leu
    50                  55                  60

Gly Gly His Arg Ala Ser His Lys Lys Pro Lys Leu Ile Val Asp Gln
65                  70                  75                  80

Glu Gln Val Lys His Arg Asn Lys Glu Asn Asp Met His Lys Cys Thr
                85                  90                  95

Ile Cys Asp Gln Met Phe Gly Thr Gly Gln Ala Leu Gly Gly His Met
            100                 105                 110

Arg Lys His Arg Thr Ser Met Ile Thr Glu Gln Ser Ile Val Pro Ser
        115                 120                 125

Val Val Tyr Ser Arg Pro Val Phe Asn Arg Cys Ser Ser Lys Glu
    130                 135                 140

Ile Leu Asp Leu Asn Leu Thr Pro Leu Glu Asn Asp Leu Val Leu Ile
145                 150                 155                 160

Phe Gly Lys Asn Leu Val Pro Gln Ile Asp Leu Lys Phe Val Asn
                165                 170                 175
```

<210> SEQ ID NO 39
<211> LENGTH: 1019
<212> TYPE: DNA
<213> ORGANISM: Arabidopsis thaliana

<400> SEQUENCE: 39

```
ctggttactg tcttgcttgc ttccgacgat ctatcttccc cgagtagatt tggtacttcc     60
ttctttcgat ttttagaaat ggctgctcct cctgctagag ctcgtgctga ttacgattac    120
ctcattaaac ttctgctgat cggagacagc ggtgttggta agagttgcct tctcttacgt    180
ttctcagatg gctcgtttac caccagtttc attacaacta tgggattga ttttaagata    240
cggactattg agctcgatgg gaagagaatt aagctgcaaa tctgggatac tgccggacag    300
gagcggttcc gcacaatcac aactgcgtac taccgtggag ccatggggat tttgcttgtg    360
tatgatgtga ctgatgaatc atctttcaac aacatcagga attggatccg taacattgag    420
cagcatgctt ctgatagtgt caacaagatt ctagttggga caaaagcaga tatggatgaa    480
agcaaaagag ctgtgccaaa atctaagggc caagctcttg cagatgaata tggaatgaag    540
tttttcgaga ctagtgccaa gactaactta acgttgagg aagttttctt ctctattgct    600
aaagacatta agcaaagact tgcagatacc gatgcacgag ctgagccgca acaatcaaa    660
atcaaccaat ccgaccaagg tgcgggaaca tctcaagcta ctcagaaatc agcatgttgc    720
ggcacataaa aattgggtcc acgacgcctg tcaaaggaga gaatctggct agtgaaagag    780
aaatggtatt tggaaagaaa aaatgaaaaa ggaaatcaat cttcttttgc ttttcttcta    840
tatgagatgg tgtttctacg tattctttta agattctctc tttccctaat ggtatagtgt    900
```

```
gactgtgaag gacacaattc gtattccata tttctggaat ggattctctg acatcagatt      960
atgacttatg ataatatcag tttatctcac tcacacacca atgatattgg attctatgt     1019

<210> SEQ ID NO 40
<211> LENGTH: 216
<212> TYPE: PRT
<213> ORGANISM: Arabidopsis thaliana

<400> SEQUENCE: 40

Met Ala Ala Pro Pro Ala Arg Ala Arg Ala Asp Tyr Asp Tyr Leu Ile
1               5                   10                  15

Lys Leu Leu Leu Ile Gly Asp Ser Gly Val Gly Lys Ser Cys Leu Leu
            20                  25                  30

Leu Arg Phe Ser Asp Gly Ser Phe Thr Thr Ser Phe Ile Thr Thr Ile
        35                  40                  45

Gly Ile Asp Phe Lys Ile Arg Thr Ile Glu Leu Asp Gly Lys Arg Ile
    50                  55                  60

Lys Leu Gln Ile Trp Asp Thr Ala Gly Gln Glu Arg Phe Arg Thr Ile
65                  70                  75                  80

Thr Thr Ala Tyr Tyr Arg Gly Ala Met Gly Ile Leu Leu Val Tyr Asp
                85                  90                  95

Val Thr Asp Glu Ser Ser Phe Asn Asn Ile Arg Asn Trp Ile Arg Asn
            100                 105                 110

Ile Glu Gln His Ala Ser Asp Ser Val Asn Lys Ile Leu Val Gly Asn
        115                 120                 125

Lys Ala Asp Met Asp Glu Ser Lys Arg Ala Val Pro Lys Ser Lys Gly
    130                 135                 140

Gln Ala Leu Ala Asp Glu Tyr Gly Met Lys Phe Phe Glu Thr Ser Ala
145                 150                 155                 160

Lys Thr Asn Leu Asn Val Glu Glu Val Phe Phe Ser Ile Ala Lys Asp
                165                 170                 175

Ile Lys Gln Arg Leu Ala Asp Thr Asp Ala Arg Ala Glu Pro Gln Thr
            180                 185                 190

Ile Lys Ile Asn Gln Ser Asp Gln Gly Ala Gly Thr Ser Gln Ala Thr
        195                 200                 205

Gln Lys Ser Ala Cys Cys Gly Thr
    210                 215

<210> SEQ ID NO 41
<211> LENGTH: 1056
<212> TYPE: DNA
<213> ORGANISM: Arabidopsis thaliana

<400> SEQUENCE: 41
aaaaaaactt ctgaatctcc gaaaaaagcc aatcggggga agaaaaaaat tcaacggccg       60
tctggttact gtcttgcttg cttccgacga tctatcttcc ccgagtagat ttgaaatggc      120
tgctcctcct gctagagctc gtgctgatta cgattacctc attaaacttc tgctgatcgg      180
agacagcggt gttggtaaga gttgccttct cttacgtttc tcagatggct cgtttaccac      240
cagtttcatt acaactattg ggattgattt taagatacgg actattgagc tcgatgggaa      300
gagaattaag ctgcaaatct gggatactgc cggacaggag cggttccgca caatcacaac      360
tgcgtactac cgtggagcca tggggatttt gcttgtgtat gatgtgactg atgaatcatc      420
tttcaacaac atcaggaatt ggatccgtaa cattgagcag catgcttctg atagtgtcaa      480
caagattcta gttgggaaca agcagatat ggatgaaagc aaaagagctg tgccaaaatc      540
```

```
taagggccaa gctcttgcag atgaatatgg aatgaagttt ttcgagacta gtgccaagac    600
taacttaaac gttgaggaag ttttcttctc tattgctaaa gacattaagc aaagacttgc    660
agataccgat gcacgagctg agccgcaaac aatcaaaatc aaccaatccg accaaggtgc    720
gggaacatct caagctactc agaaatcagc atgttgcggc ataaaaaat tgggtccacg     780 acgcctgtca aggagagaa tctggctagt gaaagagaaa tggtatttgg aaagaaaaaa     840
tgaaaaagga aatcaatctt cttttgcttt tcttctatat gagatggtgt ttctacgtat    900
tcttttaaga ttctctcttt ccctaatggt atagtgtgac tgtgaaggac acaattcgta    960
ttccatattt ctggaatgga ttctctgaca tcagattatg acttatgata atatcagttt    1020
atctcactca cacaccaatg atattggatt ctatgt                              1056
```

<210> SEQ ID NO 42
<211> LENGTH: 216
<212> TYPE: PRT
<213> ORGANISM: Arabidopsis thaliana

<400> SEQUENCE: 42

```
Met Ala Ala Pro Pro Ala Arg Ala Arg Ala Asp Tyr Asp Tyr Leu Ile
1               5                   10                  15

Lys Leu Leu Leu Ile Gly Asp Ser Gly Val Gly Lys Ser Cys Leu Leu
            20                  25                  30

Leu Arg Phe Ser Asp Gly Ser Phe Thr Thr Ser Phe Ile Thr Thr Ile
        35                  40                  45

Gly Ile Asp Phe Lys Ile Arg Thr Ile Glu Leu Asp Gly Lys Arg Ile
    50                  55                  60

Lys Leu Gln Ile Trp Asp Thr Ala Gly Gln Glu Arg Phe Arg Thr Ile
65                  70                  75                  80

Thr Thr Ala Tyr Tyr Arg Gly Ala Met Gly Ile Leu Leu Val Tyr Asp
                85                  90                  95

Val Thr Asp Glu Ser Ser Phe Asn Asn Ile Arg Asn Trp Ile Arg Asn
            100                 105                 110

Ile Glu Gln His Ala Ser Asp Ser Val Asn Lys Ile Leu Val Gly Asn
        115                 120                 125

Lys Ala Asp Met Asp Glu Ser Lys Arg Ala Val Pro Lys Ser Lys Gly
    130                 135                 140

Gln Ala Leu Ala Asp Glu Tyr Gly Met Lys Phe Glu Thr Ser Ala
145                 150                 155                 160

Lys Thr Asn Leu Asn Val Glu Glu Val Phe Phe Ser Ile Ala Lys Asp
                165                 170                 175

Ile Lys Gln Arg Leu Ala Asp Thr Asp Ala Arg Ala Glu Pro Gln Thr
            180                 185                 190

Ile Lys Ile Asn Gln Ser Asp Gln Gly Ala Gly Thr Ser Gln Ala Thr
        195                 200                 205

Gln Lys Ser Ala Cys Cys Gly Thr
    210                 215
```

<210> SEQ ID NO 43
<211> LENGTH: 1294
<212> TYPE: DNA
<213> ORGANISM: Arabidopsis thaliana

<400> SEQUENCE: 43

```
atattccaaa attaaagaga atttaattta ttgttttcct tccagaaaaa tattaatatt     60 cttttctaaac taaaaaatgg agtcttcaaa tagcacagaa gcagagacat agagcgggaa    120
```

-continued

```
cgcgtttagt cacagctttc ttctccttta gctttctctct ctacacttgc ttctctctct      180
ctctcctttg ggttatcctt cttgagatct gtgcttgcgt ttcttcttca ttcgacgaca      240
ctttatctcg ggagatttca gatttgtcga tttgttcagc aatggcgcca ccgattgagg      300
tttctaccaa aagctacgtt gagaaacatg tttcacttcc tactcttaat gagaggatac      360
tttcgtccat gagtcacaga tcagtagctg cacacccatg gcatgatctc gagataggac      420
ctgaagcccc aattatcttc aattgtgtgg ttgagatagg aaaagggagc aaggtgaaat      480
atgaactcga caaaactacg ggtctcatta aggtcgaccg tattctttac tcatctgtcg      540 tatcccaca caactatggg ttcattccgc gtacccttg tgaggacagt gaccctattg      600
atgttcttgt cattatgcag gaaccggtga tcccaggatg ctttcttcgg gccaaagcta      660
ttggtctgat gccaatgatt gatcagggtg agaaagacga caagatcatt gctgtctgcg      720
ctgacgatcc agagtatcgc cattacaacg acatcagtga gcttccgcct catcgtatgg      780
ctgagatccg ccgtttcttt gaagactata agaaaaacga gaacaaggaa gtagccgtta      840
acgacttcct tccggcaact gcagcctacg acgcagttca gcattccatg gatctctatg      900 cagactacg cgtggagaac ctaagacgtt gaatcaccac ctcaagcaat ggaatgaaag      960
ctcacaactg cattattcac aaatataaat atacatataa atgtcaggct tctcaaagga     1020
tatatttgtt gtgtatgtcc tctgatgaat ccggtagatg atgccgataa ttcttttttt     1080
tttttgtcgt atgaaaccga taatcaaaga ctaaaacagg gattttctc atttgtggtc     1140 atcacttttt aaattttggt gtcatttctc atcttaatca atttgttttt gagttttatt     1200
cttctattag atctttttata catcaaagaa tagatgaaga ttcctcccta aaaccttata     1260
gtatgtcatt tattcacaat atgttatacg tgtt                                  1294
```

<210> SEQ ID NO 44
<211> LENGTH: 216
<212> TYPE: PRT
<213> ORGANISM: Arabidopsis thaliana

<400> SEQUENCE: 44

```
Met Ala Pro Pro Ile Glu Val Ser Thr Lys Ser Tyr Val Glu Lys His
1               5                   10                  15

Val Ser Leu Pro Thr Leu Asn Glu Arg Ile Leu Ser Ser Met Ser His
            20                  25                  30

Arg Ser Val Ala Ala His Pro Trp His Asp Leu Glu Ile Gly Pro Glu
        35                  40                  45

Ala Pro Ile Ile Phe Asn Cys Val Val Glu Ile Gly Lys Gly Ser Lys
    50                  55                  60

Val Lys Tyr Glu Leu Asp Lys Thr Thr Gly Leu Ile Lys Val Asp Arg
65                  70                  75                  80

Ile Leu Tyr Ser Ser Val Val Tyr Pro His Asn Tyr Gly Phe Ile Pro
                85                  90                  95

Arg Thr Leu Cys Glu Asp Ser Asp Pro Ile Asp Val Leu Val Ile Met
            100                 105                 110

Gln Glu Pro Val Ile Pro Gly Cys Phe Leu Arg Ala Lys Ala Ile Gly
        115                 120                 125

Leu Met Pro Met Ile Asp Gln Gly Glu Lys Asp Lys Ile Ile Ala
    130                 135                 140

Val Cys Ala Asp Asp Pro Glu Tyr Arg His Tyr Asn Asp Ile Ser Glu
145                 150                 155                 160

Leu Pro Pro His Arg Met Ala Glu Ile Arg Arg Phe Phe Glu Asp Tyr
                165                 170                 175
```

Lys Lys Asn Glu Asn Lys Glu Val Ala Val Asn Asp Phe Leu Pro Ala
            180                 185                 190

Thr Ala Ala Tyr Asp Ala Val Gln His Ser Met Asp Leu Tyr Ala Asp
        195                 200                 205

Tyr Val Val Glu Asn Leu Arg Arg
    210                 215

<210> SEQ ID NO 45
<211> LENGTH: 1006
<212> TYPE: DNA
<213> ORGANISM: Arabidopsis thaliana

<400> SEQUENCE: 45
ctttcctatc cctaaaaccc gagagagcat cttcttctcc tcttagggta gaagaaggac        60
gaaaatcgga ggaggaagaa gaagatcgat tcgatttgtg atcaacgatg agctccttca       120
atggaaacag caacatcgac aacctcctaa tccaaaccct acttggacgt ctccaaattc       180 gtcccctaa ctctcatttc ctctctcaat ccctagacga cctcctcttc aaatccgacg        240
acagcgacgg cgatgatgac ggagaaggtc agaccagtct cgacagagaa gaagctaggc       300
ttgagaaaga gctaatccga gtcatcgtct ctggtcgaag cgattctctc aagccgaatt       360
caggtcaagc cgtgacagtc aacgaacacc acatctgcgt tgggtttcat gaggatgagg       420
aatcggatta tcgtgtttgg gagtggcatg gtcatatcat gttgtttgat gaagagaatg       480
ggtacacgcc tgagtatatc tacgggaatt acttcgagag gttgcctgtg aagcttccta       540
ataaccgccg tgtggagaag gagaagaaga aggagatgaa agaagaggag gtggagaatt       600
tggggcttag agagttgatc gatggtggtg acgctgctcc tggtaggatt cttcatagga       660
acaacatcaa catcggttcc tcaagggtct aagttcctaa gagcgtcttg gtagggagag       720
gtcacattgt tcgggaagat ttcagatgtg tgaacaactc gcgacaacaa aacataaggt       780
gctggtgggt ctacgggttc tattccgttt tatttaaacc gggaaatcca tgggtgaatc       840
tgttttcttt aagaaattca tctgaagttg ttctgaacc aaatttacaa tacatgttaa       900
tgaagagaga aagattaca atgcatggtc atcgaactcg gaagctttca agtttcccca        960
tgtttgttta ttttgtgttc ttaaatcaga atcatatgtt ttgctc                     1006

<210> SEQ ID NO 46
<211> LENGTH: 194
<212> TYPE: PRT
<213> ORGANISM: Arabidopsis thaliana

<400> SEQUENCE: 46

Met Ser Ser Phe Asn Gly Asn Ser Asn Ile Asp Asn Leu Leu Ile Gln
1               5                   10                  15

Thr Leu Leu Gly Arg Leu Gln Ile Arg Pro Pro Asn Ser His Phe Leu
            20                  25                  30

Ser Gln Ser Leu Asp Asp Leu Leu Phe Lys Ser Asp Ser Asp Gly
        35                  40                  45

Asp Asp Asp Gly Glu Gly Gln Thr Ser Leu Asp Arg Glu Glu Ala Arg
    50                  55                  60

Leu Glu Lys Glu Leu Ile Arg Val Ile Val Ser Gly Arg Ser Asp Ser
65                  70                  75                  80

Leu Lys Pro Asn Ser Gly Gln Ala Val Thr Val Asn Glu His His Ile
                85                  90                  95

Cys Val Gly Phe His Glu Asp Glu Glu Ser Asp Tyr Arg Val Trp Glu
            100                 105                 110

```
Trp His Gly His Ile Met Leu Phe Asp Glu Glu Asn Gly Tyr Thr Pro
        115                 120                 125

Glu Tyr Ile Tyr Gly Asn Tyr Phe Glu Arg Leu Pro Val Lys Leu Pro
    130                 135                 140

Asn Asn Arg Arg Val Glu Lys Glu Lys Lys Glu Met Lys Glu Glu
145                 150                 155                 160

Glu Val Glu Asn Leu Gly Leu Arg Glu Leu Ile Asp Gly Gly Asp Ala
            165                 170                 175

Ala Pro Gly Arg Ile Leu His Arg Asn Asn Ile Asn Ile Gly Ser Ser
        180                 185                 190

Arg Val

<210> SEQ ID NO 47
<211> LENGTH: 1929
<212> TYPE: DNA
<213> ORGANISM: Arabidopsis thaliana

<400> SEQUENCE: 47
atggtgagcg ataagatagt agaatcaagc caccgcaaac accgtaggtc gtattctcct      60
tccgacgaag tcgttaaatc ttccaagcgg cacaagcacc atcatcacaa gcatcgacac     120
agtcatcatc ttgatgagga cggcaatgaa aagaatgttt atccattttt ggggaatcct     180
ggtaacgatg gtgaacttga tttggaggaa ggggagaatt gaagaagaa gggaagcatt      240 gatagagaaa gcaatagaga caactacaga ggtaggagta gtagagataa agctaggtct     300
agtagtagag agactgggag ggagaatgaa agagagagac gtaaggatca agatagggat     360
agaggaagaa gagaagacca gagtgatcag gagatctata aaagtggtgg tgatggatat     420
ggggaagtta ggcatgatgc agaagatgac ttagattctt taaaaagcca taaacctaac     480
ggtgaaactc agggcaacgt tgaaaggtct gaagttgata tgatgatga cggtgaagat      540 gttgtttggg gagttgaaga acaagaagct gcagagatga aaagaatcga ggaaagcaag     600
aggattacgc aagccatatt ggagaaatat aagaaaaagt tggagcagtc ctctactgtg     660
gcagatgttc aagctaaagc tgggttggat actgaggccg tagatggtga agtcgccaag     720
ctatcttcag cagttgggga aacacctgca cggcttgtga tatcagactc agatatgaca     780
ctagcttccg caggcagccc aaagagtgac atgttcagtg atgatatctt ggggagtct      840 cctctagctg atggtactcg gaaagggaat gcacttgttc cttttgtaag gagtggactc     900
aatgataatt gggatgatgc agaaggttat tacagttatc agcttggtga actacttgat     960
gatagatatg aaatcatggc tactcatggg aaaggtgtat tctctaccgt ggtgcgtgca    1020
aaagacacaa aacctgagct aggtgaacct gaggaagtgg ctataaaaat tattcggaaa    1080
aatgagacaa tgcataaggc tggccaggct gagattcgga tattgaagaa gctagtttgc    1140
tctgacccag agaataagca ccactgcgtc cgtcttcttt caacttttga atataggaac    1200
cacctttgct tggtgtttga gtctcttcat ctgaatctcc gtgaagttgt gaagaagatt    1260
ggtgtcaaca ttggtctaaa actatatgat gttagagtgt atgctgagca gttattcata    1320
tcccttaaac atctcaagaa ctgtgggtt cttcactgcg atataaagcc tgataacata     1380
ctaatgaatg agggaagaaa catgttaaag ctttgtgatt ttggtagtgc aatgtttgct    1440
ggtgaaaacc aagttacacc atatcttgtt agtcgtttct acagagctcc agaaatcatt    1500
cttggactac cctacgacca tccgttagat atttggtcag ttggttgttg tctgtatgag    1560
ctttatagcg ggaaaattat gttccctggc tccacaaaca atgatatgtt acgcctgcat    1620
```

```
atggaactga aaggtccctt ccctaaaaag atgcttcgca aaggagcatt tatcgatcaa    1680
cactttgata aggacttatg cttctatgct acagaggagg atagtgttac tggaaagaca    1740
ataaggagaa taatggtcaa cgtaaagcca aagatttag gttcagtaat tagacgacgt     1800
tatgaggatg aagatcccaa ggtgttggtt catttcagga atcttttgga caaaattttc    1860
acacttgatc ctcaaaagag acttacagtg tcacaggcat tagctcaccc attcatcacg    1920
ggcaagtga                                                            1929
```

<210> SEQ ID NO 48
<211> LENGTH: 642
<212> TYPE: PRT
<213> ORGANISM: Arabidopsis thaliana

<400> SEQUENCE: 48

```
Met Val Ser Asp Lys Ile Val Glu Ser Ser His Arg Lys His Arg Arg
1               5                   10                  15

Ser Tyr Ser Pro Ser Asp Glu Val Val Lys Ser Ser Arg His Lys
            20                  25                  30

His His His His Lys His Arg His Ser His His Leu Asp Glu Asp Gly
        35                  40                  45

Asn Glu Lys Asn Val Tyr Pro Phe Leu Gly Asn Pro Gly Asn Asp Gly
    50                  55                  60

Glu Leu Asp Leu Glu Glu Gly Glu Asn Leu Lys Lys Lys Gly Ser Ile
65                  70                  75                  80

Asp Arg Glu Ser Asn Arg Asp Asn Tyr Arg Gly Arg Ser Ser Arg Asp
                85                  90                  95

Lys Ala Arg Ser Ser Ser Arg Glu Thr Gly Arg Glu Asn Glu Arg Glu
            100                 105                 110

Arg Arg Lys Asp Gln Asp Arg Asp Arg Gly Arg Arg Glu Asp Gln Ser
        115                 120                 125

Asp Gln Glu Ile Tyr Lys Ser Gly Gly Asp Gly Tyr Gly Glu Val Arg
    130                 135                 140

His Asp Ala Glu Asp Asp Leu Asp Ser Leu Lys Ser His Lys Pro Asn
145                 150                 155                 160

Gly Glu Thr Gln Gly Asn Val Glu Arg Ser Glu Val Asp Asn Asp Asp
                165                 170                 175

Asp Gly Glu Asp Val Val Trp Gly Val Glu Glu Gln Glu Ala Ala Glu
            180                 185                 190

Met Lys Arg Ile Glu Glu Ser Lys Arg Ile Thr Gln Ala Ile Leu Glu
        195                 200                 205

Lys Tyr Lys Lys Lys Leu Glu Gln Ser Ser Thr Val Ala Asp Val Gln
    210                 215                 220

Ala Lys Ala Gly Leu Asp Thr Glu Ala Val Asp Gly Glu Val Ala Lys
225                 230                 235                 240

Leu Ser Ser Ala Val Gly Glu Thr Pro Ala Arg Leu Val Ile Ser Asp
                245                 250                 255

Ser Asp Met Thr Leu Ala Ser Ala Gly Ser Pro Lys Ser Asp Met Phe
            260                 265                 270

Ser Asp Asp Ile Phe Gly Glu Ser Pro Leu Ala Asp Gly Thr Arg Lys
        275                 280                 285

Gly Asn Ala Leu Val Pro Phe Val Arg Ser Gly Leu Asn Asp Asn Trp
    290                 295                 300

Asp Asp Ala Glu Gly Tyr Tyr Ser Tyr Gln Leu Gly Glu Leu Leu Asp
305                 310                 315                 320
```

-continued

Asp Arg Tyr Glu Ile Met Ala Thr His Gly Lys Gly Val Phe Ser Thr
            325                 330                 335

Val Val Arg Ala Lys Asp Thr Lys Pro Glu Leu Gly Glu Pro Glu Glu
        340                 345                 350

Val Ala Ile Lys Ile Ile Arg Lys Asn Glu Thr Met His Lys Ala Gly
        355                 360                 365

Gln Ala Glu Ile Arg Ile Leu Lys Lys Leu Val Cys Ser Asp Pro Glu
    370                 375                 380

Asn Lys His His Cys Val Arg Leu Leu Ser Thr Phe Glu Tyr Arg Asn
385                 390                 395                 400

His Leu Cys Leu Val Phe Glu Ser Leu His Leu Asn Leu Arg Glu Val
            405                 410                 415

Val Lys Lys Ile Gly Val Asn Ile Gly Leu Lys Leu Tyr Asp Val Arg
        420                 425                 430

Val Tyr Ala Glu Gln Leu Phe Ile Ser Leu Lys His Leu Lys Asn Cys
        435                 440                 445

Gly Val Leu His Cys Asp Ile Lys Pro Asp Asn Ile Leu Met Asn Glu
    450                 455                 460

Gly Arg Asn Met Leu Lys Leu Cys Asp Phe Gly Ser Ala Met Phe Ala
465                 470                 475                 480

Gly Glu Asn Gln Val Thr Pro Tyr Leu Val Ser Arg Phe Tyr Arg Ala
            485                 490                 495

Pro Glu Ile Ile Leu Gly Leu Pro Tyr Asp His Pro Leu Asp Ile Trp
        500                 505                 510

Ser Val Gly Cys Cys Leu Tyr Glu Leu Tyr Ser Gly Lys Ile Met Phe
        515                 520                 525

Pro Gly Ser Thr Asn Asn Asp Met Leu Arg Leu His Met Glu Leu Lys
    530                 535                 540

Gly Pro Phe Pro Lys Lys Met Leu Arg Lys Gly Ala Phe Ile Asp Gln
545                 550                 555                 560

His Phe Asp Lys Asp Leu Cys Phe Tyr Ala Thr Glu Glu Asp Ser Val
            565                 570                 575

Thr Gly Lys Thr Ile Arg Arg Ile Met Val Asn Val Lys Leu Pro Lys Asp
        580                 585                 590

Leu Gly Ser Val Ile Arg Arg Tyr Glu Asp Glu Pro Lys Val
        595                 600                 605

Leu Val His Phe Arg Asn Leu Leu Asp Lys Ile Phe Thr Leu Asp Pro
    610                 615                 620

Gln Lys Arg Leu Thr Val Ser Gln Ala Leu Ala His Pro Phe Ile Thr
625                 630                 635                 640

Gly Lys

<210> SEQ ID NO 49
<211> LENGTH: 417
<212> TYPE: DNA
<213> ORGANISM: Arabidopsis thaliana
<400> SEQUENCE: 49
atggctccga aagcggcaga gaagaaaccg gctgggaaga agccagcaga aaaagctccg      60
gcagagaaat taccaaaggc ggagaagaag atcaccaagg aaggtggaag cgaaaagaag     120
aagaagaaat cgaagaagaa catcgagacg tacaagatct acatcttcaa ggttctgaaa     180
caagttcatc ctgatatcgg aatctccggg aaagcgatgg ggatcatgaa cagtttcatc     240
aacgacatct tcgagaaact agctcaggaa tcatcgcgat ggctaggta caacaagaaa     300

-continued

```
ccgacgatca cttctcggga aattcagacg gcggtgagac ttgtgttgcc tggagagctc      360
tcgaaacacg ctgtttctga aggcactaag gcggttacta aattcactag ctcgtag        417
```

<210> SEQ ID NO 50
<211> LENGTH: 138
<212> TYPE: PRT
<213> ORGANISM: Arabidopsis thaliana

<400> SEQUENCE: 50

```
Met Ala Pro Lys Ala Ala Glu Lys Lys Pro Ala Gly Lys Lys Pro Ala
1               5                   10                  15

Glu Lys Ala Pro Ala Glu Lys Leu Pro Lys Ala Glu Lys Lys Ile Thr
            20                  25                  30

Lys Glu Gly Gly Ser Glu Lys Lys Lys Lys Ser Lys Lys Asn Ile
        35                  40                  45

Glu Thr Tyr Lys Ile Tyr Ile Phe Lys Val Leu Lys Gln Val His Pro
    50                  55                  60

Asp Ile Gly Ile Ser Gly Lys Ala Met Gly Ile Met Asn Ser Phe Ile
65                  70                  75                  80

Asn Asp Ile Phe Glu Lys Leu Ala Gln Glu Ser Ser Arg Leu Ala Arg
                85                  90                  95

Tyr Asn Lys Lys Pro Thr Ile Thr Ser Arg Glu Ile Gln Thr Ala Val
            100                 105                 110

Arg Leu Val Leu Pro Gly Glu Leu Ser Lys His Ala Val Ser Glu Gly
        115                 120                 125

Thr Lys Ala Val Thr Lys Phe Thr Ser Ser
    130                 135
```

<210> SEQ ID NO 51
<211> LENGTH: 2205
<212> TYPE: DNA
<213> ORGANISM: Arabidopsis thaliana

<400> SEQUENCE: 51

```
atggctgcga ttgaattaca caagccggag atcaacgccg atgacgacga tgacgaatcc      60
ccggtggagc aggttcgtct cactgtatcg aaccacgacg atccttctct accagtgtgg     120
acgtttcgga tgtggttttt agggcttctc tcttgtattc tcctctcgtt tctcaacact     180
ttcttcggat acagaactca gcctctgatg atcactatga tctctgttca agttgttacg     240
ttgcctttag gaagcttat ggctagggtt tgcctgaga ccaagtataa gattggttcg       300
tgggagtttt cttttaatcc gggtcccttt aacgtcaagg aacatgtgtt gatctctatg     360
tttgctaatg ctggtgctgg atttggatct ggtactgctt acgctgttgg tattgttgat     420
atcatcatgg cttttatata aaggaagatt agtttcttgg ctagttggat tcttgtcatc     480
actactcaga ttcttgggta tggttgggct ggtatcatga aaagttagt tgttgatcct     540 gcacagatgt ggtggcctac gagtgttctt caagtctctc tgtttcgtgc tcttcatgag     600
aaggacaatg caagaatgtc acgaggaaag ttctttgtga ttgcgtttgt ttgtagcttc     660
gcgtggtaca tattcccagc ttatttgttc ttgaccttat catcaatatc ttgggtttgt     720
tgggcattcc cgaagtctat cacagctcag cagttaggat ctggaatgtc aggacttggg     780
attggtgcat tgctcttga ttggtctgtt atagcttctt accttggaag ccctcttgtg      840 actccttttct ttgcaattgt caatgtcctt gttggttacg ttttggtcat gtatatggtt     900
ataccaatat catattgggg catgaatgtg tatgaagcaa acaagtttcc aattttctcc     960
tctgatctgt tgataagca aggcaacttt acaatatct ccaccattgt caacaacaag       1020
```

```
tttgaattgg acatggagaa ttatcaacaa caaggtcggg tttatctcag tacgttcttt      1080
gctatcagtt acgggattgg tttcgcagca atcgtttcca cactgactca tgttgctctc      1140
ttcaatggaa agggaatttg gcaacaagta cgagcttcaa ctaaagctaa aatggacata      1200
cacacaaggt tgatgaagaa gtacaaagac ataccaggtt ggtggtttta cagtctgctt      1260
gcgatctcat tggtgctatc tcttgtcctc tgcattttca tgaaagacga gatccaaatg      1320
ccttggtggg gactccttct agcatcattc atggcccctta cattcactgt accagtcagc      1380
attatcacag ctactactaa tcagactcca ggtctgaaca ttatcacaga atatctcatg      1440
ggtgtgttgt taccggggag accaatagct aacgtctgct tcaaaactta tgggtacata      1500
agcatgtcac aagctatatc attccttaac gacttcaagc taggccatta catgaagata      1560
ccaccaagat cgatgttctt agtccagttc ataggaacgg tgatagcagg aacagtgaat      1620
atatcagtgg catggtactt gctgacatca gtagaaaaca tctgccagaa ggagttgctt      1680
cctccaaaca gtccatggac atgtccaagt gacagagttt tcttcgacgc atcagtgatt      1740
tggggattag taggacccaa gagaatcttt ggtcggctag aaaactaccc tgcactaaac      1800
tggttcttct taggtggact aataggaccg gtcctcgtgt ggcttctcca aaaagccttc      1860
ccaacgaaaa catggatctc gcagatcaat ctcccagttc ttttaggagc aacagcagca      1920
atgccgccag cgacaagcgt gaacttcaac tgctggatca tagtaggagt gatattcaat      1980
tactttgtgt tcaagtactg caaaaagtgg tggcagaggt ataactacgt gctatcggca      2040
gctttggatg cgggattggc gttcatggga gtgttgttat actttagttt gacgatgaat      2100
ggaatatcga taaatcattg gtggggtgct aagggtgaga attgtcctct gcttcttgt       2160 cctactgctc ctggtgttct agttgatggt tgtcctgttt tttaa                     2205
```

<210> SEQ ID NO 52
<211> LENGTH: 734
<212> TYPE: PRT
<213> ORGANISM: Arabidopsis thaliana

<400> SEQUENCE: 52

```
Met Ala Ala Ile Glu Leu His Lys Pro Glu Ile Asn Ala Asp Asp Asp
1               5                   10                  15

Asp Asp Glu Ser Pro Val Glu Gln Val Arg Leu Thr Val Ser Asn His
            20                  25                  30

Asp Asp Pro Ser Leu Pro Val Trp Thr Phe Arg Met Trp Phe Leu Gly
        35                  40                  45

Leu Leu Ser Cys Ile Leu Leu Ser Phe Leu Asn Thr Phe Phe Gly Tyr
    50                  55                  60

Arg Thr Gln Pro Leu Met Ile Thr Met Ile Ser Val Gln Val Val Thr
65                  70                  75                  80

Leu Pro Leu Gly Lys Leu Met Ala Arg Val Leu Pro Glu Thr Lys Tyr
                85                  90                  95

Lys Ile Gly Ser Trp Glu Phe Ser Phe Asn Pro Gly Pro Phe Asn Val
            100                 105                 110

Lys Glu His Val Leu Ile Ser Met Phe Ala Asn Ala Gly Ala Gly Phe
        115                 120                 125

Gly Ser Gly Thr Ala Tyr Ala Val Gly Ile Val Asp Ile Ile Met Ala
    130                 135                 140

Phe Tyr Lys Arg Lys Ile Ser Phe Leu Ala Ser Trp Ile Leu Val Ile
145                 150                 155                 160

Thr Thr Gln Ile Leu Gly Tyr Gly Trp Ala Gly Ile Met Arg Lys Leu
```

-continued

```
            165                 170                 175
Val Val Asp Pro Ala Gln Met Trp Trp Pro Thr Ser Val Leu Gln Val
            180                 185                 190
Ser Leu Phe Arg Ala Leu His Glu Lys Asp Asn Ala Arg Met Ser Arg
            195                 200                 205
Gly Lys Phe Val Ile Ala Phe Val Cys Ser Phe Ala Trp Tyr Ile
            210                 215                 220
Phe Pro Ala Tyr Leu Phe Leu Thr Leu Ser Ser Ile Ser Trp Val Cys
225                 230                 235                 240
Trp Ala Phe Pro Lys Ser Ile Thr Ala Gln Gln Leu Gly Ser Gly Met
            245                 250                 255
Ser Gly Leu Gly Ile Gly Ala Phe Ala Leu Asp Trp Ser Val Ile Ala
            260                 265                 270
Ser Tyr Leu Gly Ser Pro Leu Val Thr Pro Phe Phe Ala Ile Val Asn
            275                 280                 285
Val Leu Val Gly Tyr Val Leu Val Met Tyr Met Val Ile Pro Ile Ser
            290                 295                 300
Tyr Trp Gly Met Asn Val Tyr Glu Ala Asn Lys Phe Pro Ile Phe Ser
305                 310                 315                 320
Ser Asp Leu Phe Asp Lys Gly Gln Leu Tyr Asn Ile Ser Thr Ile
            325                 330                 335
Val Asn Asn Lys Phe Glu Leu Asp Met Glu Asn Tyr Gln Gln Gln Gly
            340                 345                 350
Arg Val Tyr Leu Ser Thr Phe Phe Ala Ile Ser Tyr Gly Ile Gly Phe
            355                 360                 365
Ala Ala Ile Val Ser Thr Leu Thr His Val Ala Leu Phe Asn Gly Lys
            370                 375                 380
Gly Ile Trp Gln Gln Val Arg Ala Ser Thr Lys Ala Lys Met Asp Ile
385                 390                 395                 400
His Thr Arg Leu Met Lys Lys Tyr Lys Asp Ile Pro Gly Trp Trp Phe
            405                 410                 415
Tyr Ser Leu Leu Ala Ile Ser Leu Val Leu Ser Leu Val Leu Cys Ile
            420                 425                 430
Phe Met Lys Asp Glu Ile Gln Met Pro Trp Trp Gly Leu Leu Leu Ala
            435                 440                 445
Ser Phe Met Ala Leu Thr Phe Thr Val Pro Val Ser Ile Ile Thr Ala
            450                 455                 460
Thr Thr Asn Gln Thr Pro Gly Leu Asn Ile Ile Thr Glu Tyr Leu Met
465                 470                 475                 480
Gly Val Leu Leu Pro Gly Arg Pro Ile Ala Asn Val Cys Phe Lys Thr
            485                 490                 495
Tyr Gly Tyr Ile Ser Met Ser Gln Ala Ile Ser Phe Leu Asn Asp Phe
            500                 505                 510
Lys Leu Gly His Tyr Met Lys Ile Pro Pro Arg Ser Met Phe Leu Val
            515                 520                 525
Gln Phe Ile Gly Thr Val Ile Ala Gly Thr Val Asn Ile Ser Val Ala
            530                 535                 540
Trp Tyr Leu Leu Thr Ser Val Glu Asn Ile Cys Gln Lys Glu Leu Leu
545                 550                 555                 560
Pro Pro Asn Ser Pro Trp Thr Cys Pro Ser Asp Arg Val Phe Phe Asp
            565                 570                 575
Ala Ser Val Ile Trp Gly Leu Val Gly Pro Lys Arg Ile Phe Gly Arg
            580                 585                 590
```

| Leu | Gly | Asn | Tyr | Pro | Ala | Leu | Asn | Trp | Phe | Phe | Leu | Gly | Gly | Leu | Ile |
|---|---|---|---|---|---|---|---|---|---|---|---|---|---|---|---|
| | 595 | | | | 600 | | | | | 605 | | | | | |

| Gly | Pro | Val | Leu | Val | Trp | Leu | Leu | Gln | Lys | Ala | Phe | Pro | Thr | Lys | Thr |
|---|---|---|---|---|---|---|---|---|---|---|---|---|---|---|---|
| 610 | | | | | 615 | | | | | 620 | | | | | |

| Trp | Ile | Ser | Gln | Ile | Asn | Leu | Pro | Val | Leu | Leu | Gly | Ala | Thr | Ala | Ala |
|---|---|---|---|---|---|---|---|---|---|---|---|---|---|---|---|
| 625 | | | | | 630 | | | | | 635 | | | | | 640 |

| Met | Pro | Pro | Ala | Thr | Ser | Val | Asn | Phe | Asn | Cys | Trp | Ile | Ile | Val | Gly |
|---|---|---|---|---|---|---|---|---|---|---|---|---|---|---|---|
| | | | | 645 | | | | | 650 | | | | | 655 | |

| Val | Ile | Phe | Asn | Tyr | Phe | Val | Phe | Lys | Tyr | Cys | Lys | Lys | Trp | Trp | Gln |
|---|---|---|---|---|---|---|---|---|---|---|---|---|---|---|---|
| | | | 660 | | | | | 665 | | | | | 670 | | |

| Arg | Tyr | Asn | Tyr | Val | Leu | Ser | Ala | Ala | Leu | Asp | Ala | Gly | Leu | Ala | Phe |
|---|---|---|---|---|---|---|---|---|---|---|---|---|---|---|---|
| | | 675 | | | | | 680 | | | | | 685 | | | |

| Met | Gly | Val | Leu | Leu | Tyr | Phe | Ser | Leu | Thr | Met | Asn | Gly | Ile | Ser | Ile |
|---|---|---|---|---|---|---|---|---|---|---|---|---|---|---|---|
| | 690 | | | | | 695 | | | | | 700 | | | | |

| Asn | His | Trp | Trp | Gly | Ala | Lys | Gly | Glu | Asn | Cys | Pro | Leu | Ala | Ser | Cys |
|---|---|---|---|---|---|---|---|---|---|---|---|---|---|---|---|
| 705 | | | | | 710 | | | | | 715 | | | | | 720 |

| Pro | Thr | Ala | Pro | Gly | Val | Leu | Val | Asp | Gly | Cys | Pro | Val | Phe |
|---|---|---|---|---|---|---|---|---|---|---|---|---|---|
| | | | | 725 | | | | | 730 | | | | |

<210> SEQ ID NO 53
<211> LENGTH: 1127
<212> TYPE: DNA
<213> ORGANISM: Arabidopsis thaliana

<400> SEQUENCE: 53

```
gaagaagaga agaagaagaa ccttacaatt gcttttgtaa atattgtagg tagtttaagg     60
acgtcactac ctacatacat ggatttatgt ggaactcaga tgctgcgcct ctcatcgcct    120
catttcaaaa cccttcattt ggtgaggcat gcacaaggag tccacaatat agcattagaa    180
gagaagggag agaaacctga atcagaaaag cttttgacg cccaccttc tccaaagggt     240
ttgcaacagg tttcggaaag gcgcaaccaa atccttgaat caggattact aaacactgtc    300
gagttagtga taacctctcc gctgtgcaga gcaatggaaa cttcaatagg aatatttagg    360
ggacaaggat atgtaaatat atccgaagac tttgcaaaag ctaacaactt ccctccaatt    420
gtagcacttg agatctgtag agaacgcatg ggactctatc catgtgatcg tagagcaagt    480
ataagtactc gccgcacttt ttttcctgag atcgacttta caatgataga gagtgatgaa    540
gacgctctat ggcaagacaa ggaaagggaa aaattagaag atgttgctac tagaggtctt    600
cactttgtta atggttatg ggagagacca gaaaagaga tagcaattgt aagccacggg     660
attttcttgc aacaaacact tgtgcgctg catggaaaag ttggcatacc tcttgaagat    720
agtctcctta caaggtttgc caattgtgaa ctccggtcga ttcggataga aagagtgac     780
atggaagcgg atacattaat gacttgtaac tgtagaaatt acgttactcc accttcaact    840
tccttccatt cacacgcttg aatagaaggc atgcatatgt tatatatgaa ctgtgtttc    900
ttttccaagc cacactcatg gatcggagtt tcagaaccaa ggaaaatcga agctactatt    960
cccatttgcc attaccaagc taccagcacc aatacattgt aatcaatcac tagtaacaaa    1020
aaaatctata atttcaaaga tacgtttaca tcgaaaaaaa gaaagataac gtttgcaaat   1080
gatataaaag cttttccttt tttttttttt taattattat gaaaaaa                  1127
```

<210> SEQ ID NO 54
<211> LENGTH: 260
<212> TYPE: PRT
<213> ORGANISM: Arabidopsis thaliana

<400> SEQUENCE: 54

```
Met Asp Leu Cys Gly Thr Gln Met Leu Arg Leu Ser Ser Pro His Phe
1               5                   10                  15

Lys Thr Leu His Leu Val Arg His Ala Gln Gly Val His Asn Ile Ala
            20                  25                  30

Leu Glu Glu Lys Gly Glu Lys Pro Glu Ser Glu Lys Leu Phe Asp Ala
        35                  40                  45

His Leu Ser Pro Lys Gly Leu Gln Gln Val Ser Glu Arg Arg Asn Gln
    50                  55                  60

Ile Leu Glu Ser Gly Leu Leu Asn Thr Val Glu Leu Val Ile Thr Ser
65                  70                  75                  80

Pro Leu Cys Arg Ala Met Glu Thr Ser Ile Gly Ile Phe Arg Gly Gln
                85                  90                  95

Gly Tyr Val Asn Ile Ser Glu Asp Phe Ala Lys Ala Asn Asn Phe Pro
            100                 105                 110

Pro Ile Val Ala Leu Glu Ile Cys Arg Glu Arg Met Gly Leu Tyr Pro
        115                 120                 125

Cys Asp Arg Arg Ala Ser Ile Ser Thr Arg Arg Thr Phe Phe Pro Glu
    130                 135                 140

Ile Asp Phe Thr Met Ile Glu Ser Asp Glu Asp Ala Leu Trp Gln Asp
145                 150                 155                 160

Lys Glu Arg Glu Lys Leu Glu Asp Val Ala Thr Arg Gly Leu His Phe
                165                 170                 175

Val Lys Trp Leu Trp Glu Arg Pro Lys Glu Ile Ala Ile Val Ser
            180                 185                 190

His Gly Ile Phe Leu Gln Gln Thr Leu Cys Ala Leu His Gly Lys Val
    195                 200                 205

Gly Ile Pro Leu Glu Asp Ser Leu Leu Thr Arg Phe Ala Asn Cys Glu
            210                 215                 220

Leu Arg Ser Ile Arg Ile Glu Lys Ser Asp Met Glu Ala Asp Thr Leu
225                 230                 235                 240

Met Thr Cys Asn Cys Arg Asn Tyr Val Thr Pro Pro Ser Thr Ser Phe
                245                 250                 255

His Ser His Ala
        260
```

<210> SEQ ID NO 55
<211> LENGTH: 696
<212> TYPE: DNA
<213> ORGANISM: Arabidopsis thaliana

<400> SEQUENCE: 55

| | | | | | |
|---|---|---|---|---|---|
| atggatgcaa | gattcttgta | ccccttggag | agctgtaaaa | tcattcactt | gttgcgacat | 60 |
| ggacaagcgt | tgcacaatgt | agaagctgag | aaagatagaa | atgcgttgtt | gtctcctcat | 120 |
| cttttgatg | ctccgcttac | cgatcatggt | caccaacagg | ttgagaatct | ccgcgaacga | 180 |
| gttgtttcaa | gcgggctact | aaagagggtt | gagctagttg | taacttctcc | gttgtttaga | 240 |
| actatgcaaa | ccgcagttgg | tgttttttgga | aatgaataca | aacaatcgag | tatgacaagt | 300 |
| agccctccca | tttttggcact | tgaggttgct | cgagaccgta | atggagtccg | tcctcctgac | 360 |
| atgagaagaa | acgttagcga | gtatcaaact | cttttccccca | ccatcgattt | ctctcagatt | 420 |
| gaaagtgaag | aggacaacct | atggagaccg | gatgttaggg | agtccgaaga | ggagattttg | 480 |
| gcgagagggt | tagagttcat | gaatggttta | tggaagaggc | cagagaagga | ggtcgcagtt | 540 |
| gttagccatg | gaatagtttt | gcagcatatg | ttgtatgtgt | ttgcaaacga | ttgtgacctg | 600 |

```
tcaattagac atgaactttg caagaggttt gccaattgcg aaattcgtac tgtcgtgatt      660
gtagacaaag gcatggcttc atctacggag aattga                                696
```

<210> SEQ ID NO 56
<211> LENGTH: 231
<212> TYPE: PRT
<213> ORGANISM: Arabidopsis thaliana

<400> SEQUENCE: 56

```
Met Asp Ala Arg Phe Leu Tyr Pro Leu Glu Ser Cys Lys Ile Ile His
1               5                   10                  15

Leu Leu Arg His Gly Gln Ala Leu His Asn Val Glu Ala Glu Lys Asp
            20                  25                  30

Arg Asn Ala Leu Leu Ser Pro His Leu Phe Asp Ala Pro Leu Thr Asp
        35                  40                  45

His Gly His Gln Gln Val Glu Asn Leu Arg Glu Arg Val Val Ser Ser
    50                  55                  60

Gly Leu Leu Lys Arg Val Glu Leu Val Val Thr Ser Pro Leu Phe Arg
65                  70                  75                  80

Thr Met Gln Thr Ala Val Gly Val Phe Gly Asn Glu Tyr Lys Gln Ser
                85                  90                  95

Ser Met Thr Ser Ser Pro Pro Ile Leu Ala Leu Glu Val Ala Arg Asp
            100                 105                 110

Arg Asn Gly Val Arg Pro Pro Asp Met Arg Arg Asn Val Ser Glu Tyr
        115                 120                 125

Gln Thr Leu Phe Pro Thr Ile Asp Phe Ser Gln Ile Glu Ser Glu Glu
    130                 135                 140

Asp Asn Leu Trp Arg Pro Asp Val Arg Glu Ser Glu Glu Ile Leu
145                 150                 155                 160

Ala Arg Gly Leu Glu Phe Met Lys Trp Leu Trp Lys Arg Pro Glu Lys
                165                 170                 175

Glu Val Ala Val Val Ser His Gly Ile Val Leu Gln His Met Leu Tyr
            180                 185                 190

Val Phe Ala Asn Asp Cys Asp Leu Ser Ile Arg His Glu Leu Cys Lys
        195                 200                 205

Arg Phe Ala Asn Cys Glu Ile Arg Thr Val Val Ile Val Asp Lys Gly
    210                 215                 220

Met Ala Ser Ser Thr Glu Asn
225                 230
```

<210> SEQ ID NO 57
<211> LENGTH: 2114
<212> TYPE: DNA
<213> ORGANISM: Arabidopsis thaliana

<400> SEQUENCE: 57

```
agaattttc cgtccaaatt gttttggtc aaagcctcaa tggtcttgaa ttgacctgtt       60
cttaaaaccc gacccggatc cacctgcttc tttcaactaa cacacgctcc tgatccaaac      120
cattttttca ttttttcaaat cattatcaac tctctcgctt cttcaacgat cgcataaatt     180
ccctctttgt ctgctcgatt cctgatctct agggtttggg ttccggagac gaaggggtg      240 tttcgtgtgt aattgagata ttgagattat tgctttgtaa aactcaaaat ctatggcggt     300
ttctagcgcc ttcgttgtta caccgaagct ggagaagctg ttagcgaatc accataatcc     360
aacgtattct tcttctccgg ccccgttgga tgtaattggg atacgtgctc ttccgatgaa     420
caataggaac aagcgaggtc tgatccagag agcgcgttgc gagatttctc cgtctaataa     480
```

-continued

```
ggcagctagc atctcagctc tcgagcagct caagacttct gctattgacc gatacactaa    540
ggaaagaagc agcattgtgg tgattgggct tagcattcac acagctcctg ttgagatgcg    600
tgagaagctt gccattccag aagctgaatg gccacgagct attgctgaat tgtgtggttt    660
gaatcatatt gaagaagctg ctgtactcag tacctgcaac cgaatggaga tttatgtttt    720
ggctctatct cagcatcgtg gagtcaaaga agtgactgag tggatgtcta agacaagtgg    780
aatcccggtt tcagaaatct gtcagcatcg ttttctattg tacaacaagg atgtcacgca    840
acatatattt gaagtctcag ctggtctaga ctctcttgtc ctaggtgaag gtcagatact    900
tgcacaggtt aaacaagttg ttaaagtagg tcaaggagtc aatggttttg ggaggaatat    960
cagtgggcta tttaaacacg caatcacagt tggaaagcgt gtcagaacag agacaaaatat 1020
cgctgctggg gctgtttccg ttagctcggc tgcagttgaa cttgctctca tgaagcttcc   1080
cgaatcttct catgcatcat ctgctaggat gttggtagtt ggtgctggaa agatggggaa   1140
gcttgtaatc aagcacttgg ttgctaaagg ttgcaccaaa atggtggttg tgaatcgaag   1200
cgaagagaaa gttgcagctg tccgcaatga gatgccgcct ggcgttgaga ttatttataa   1260
accccttgat gagatgctgt cttgtgctgc agaagctgat gtagtctttta ctagcacagc   1320
atctgagaca ccattattct tgaaggagca agtagagact ctccctcctg ttagagatgc   1380
gaggctcttt gttgatatct ctgttcctag aaatgtcggg tcctgcgtcg ctgaaataga   1440
cggtacacgg gttttcaacg tggatgacct caaggaagtc gttgctgcga ataaagaaga   1500
cagggtgagg aaagcaatgg acgctcaggc tataattaca gatgaatcaa acactttga    1560
agcgtggagg gactcgttgg agacggttcc aacaatcaag aaattaaggg gatatacaga   1620
gagaattata gctgcagaga ttgagaaatc cttgcccaaa atgggcattg acatgaacaa   1680
gaagatgagg aaaacagtag atgatctaat ccgaggtata gtgaacaagc tcctgcacgg   1740
tccaatgcag catttgagat gcgatgggaa cgatagcaga acgctgagtg agacactaga   1800
taacatgcag gctctgaaca ggatgtatgg acttgatgca gagatactcg aggagaagat   1860
tagagcaaag gtgaaaaaaa agtagagaga agagagcctt tgtttcatcc atttttttagg  1920
ttcgtagagg ttaaaaaccg gcacctttgt aatatacaca cttgagtaga gggtgaagac   1980
agcctctggg gaagatgatc ttctggttca tgcccttgat gggaagcata ccataattgt   2040
tttattgcgt tcttttgtta aagttaaaag tttaaaactt tgtacacata atatatatac   2100
atttttttt ccct                                                      2114
```

<210> SEQ ID NO 58
<211> LENGTH: 530
<212> TYPE: PRT
<213> ORGANISM: Arabidopsis thaliana

<400> SEQUENCE: 58

```
Met Ala Val Ser Ser Ala Phe Val Val Thr Pro Lys Leu Glu Lys Leu
1               5                   10                  15

Leu Ala Asn His His Asn Pro Thr Tyr Ser Ser Pro Ala Pro Leu
            20                  25                  30

Asp Val Ile Gly Ile Arg Ala Leu Pro Met Asn Asn Arg Asn Lys Arg
        35                  40                  45

Gly Leu Ile Gln Arg Ala Arg Cys Glu Ile Ser Pro Ser Asn Lys Ala
    50                  55                  60

Ala Ser Ile Ser Ala Leu Glu Gln Leu Lys Thr Ser Ala Ile Asp Arg
65                  70                  75                  80
```

-continued

```
Tyr Thr Lys Glu Arg Ser Ser Ile Val Val Ile Gly Leu Ser Ile His
             85                  90                  95

Thr Ala Pro Val Glu Met Arg Glu Lys Leu Ala Ile Pro Glu Ala Glu
            100                 105                 110

Trp Pro Arg Ala Ile Ala Glu Leu Cys Gly Leu Asn His Ile Glu Glu
            115                 120                 125

Ala Ala Val Leu Ser Thr Cys Asn Arg Met Glu Ile Tyr Val Leu Ala
130                 135                 140

Leu Ser Gln His Arg Gly Val Lys Glu Val Thr Glu Trp Met Ser Lys
145                 150                 155                 160

Thr Ser Gly Ile Pro Val Ser Glu Ile Cys Gln His Arg Phe Leu Leu
            165                 170                 175

Tyr Asn Lys Asp Val Thr Gln His Ile Phe Glu Val Ser Ala Gly Leu
            180                 185                 190

Asp Ser Leu Val Leu Gly Glu Gly Gln Ile Leu Ala Gln Val Lys Gln
            195                 200                 205

Val Val Lys Val Gly Gln Gly Val Asn Gly Phe Gly Arg Asn Ile Ser
210                 215                 220

Gly Leu Phe Lys His Ala Ile Thr Val Gly Lys Arg Val Arg Thr Glu
225                 230                 235                 240

Thr Asn Ile Ala Ala Gly Ala Val Ser Val Ser Ser Ala Ala Val Glu
            245                 250                 255

Leu Ala Leu Met Lys Leu Pro Glu Ser Ser His Ala Ser Ser Ala Arg
            260                 265                 270

Met Leu Val Val Gly Ala Gly Lys Met Gly Lys Leu Val Ile Lys His
            275                 280                 285

Leu Val Ala Lys Gly Cys Thr Lys Met Val Val Asn Arg Ser Glu
290                 295                 300

Glu Lys Val Ala Ala Val Arg Asn Glu Met Pro Pro Gly Val Glu Ile
305                 310                 315                 320

Ile Tyr Lys Pro Leu Asp Glu Met Leu Ser Cys Ala Ala Glu Ala Asp
            325                 330                 335

Val Val Phe Thr Ser Thr Ala Ser Glu Thr Pro Leu Phe Leu Lys Glu
            340                 345                 350

Gln Val Glu Thr Leu Pro Pro Val Arg Asp Ala Arg Leu Phe Val Asp
            355                 360                 365

Ile Ser Val Pro Arg Asn Val Gly Ser Cys Val Ala Glu Ile Asp Gly
            370                 375                 380

Thr Arg Val Phe Asn Val Asp Asp Leu Lys Glu Val Val Ala Ala Asn
385                 390                 395                 400

Lys Glu Asp Arg Val Arg Lys Ala Met Asp Ala Gln Ala Ile Ile Thr
            405                 410                 415

Asp Glu Ser Lys His Phe Glu Ala Trp Arg Asp Ser Leu Glu Thr Val
            420                 425                 430

Pro Thr Ile Lys Lys Leu Arg Gly Tyr Thr Glu Arg Ile Ile Ala Ala
            435                 440                 445

Glu Ile Glu Lys Ser Leu Pro Lys Met Gly Ile Asp Met Asn Lys Lys
            450                 455                 460

Met Arg Lys Thr Val Asp Asp Leu Ile Arg Gly Ile Val Asn Lys Leu
465                 470                 475                 480

Leu His Gly Pro Met Gln His Leu Arg Cys Asp Gly Asn Asp Ser Arg
            485                 490                 495

Thr Leu Ser Glu Thr Leu Asp Asn Met Gln Ala Leu Asn Arg Met Tyr
            500                 505                 510
```

Gly Leu Asp Ala Glu Ile Leu Glu Glu Lys Ile Arg Ala Lys Val Glu
            515                 520                 525

Lys Lys
    530

<210> SEQ ID NO 59
<211> LENGTH: 969
<212> TYPE: DNA
<213> ORGANISM: Arabidopsis thaliana

<400> SEQUENCE: 59
acttacttag tgagtactcc aaacataaga aacatgccaa acactagcag ctctcaaagc     60
ttcactatct tcgttgatgg ttggttaatc cgtcacaggt atttcgttga acagcttatg    120
tgtgcttctt ccttggatga aactaatcgt atctctctcg aagaacaaca atctctcgtg    180
gcccagtttc tatctcactg tcttcaatac taccaagaga aattcgcctc cgtttccctc    240 gccgggaca acgttttcac tttcttctgc ccaccgtggt ttaactccta cgctaaactt     300
attttatggg tcggcgattt caagccttct cttgtgttta aactcaccga ggtctccgtg    360
gccgacctca cgcgccacca gaaagaccgg atctcgagtc ttaagtcgga gactaggagg    420
aaagagagag aagttatgcg agatttcgcc ctcgtgcaac aaagcgtggc ggatccgccg    480
gtgatgctcg cggcgaggcg cgtgggagcg gtgggaatgg tggacggaga agaaacggat    540
ttggaggagg cgatggaggt gcttaaagct gggatggcgg cagcgatgaa caacgctgat    600
cagctacggt gttcgacggt ggggaaagtg gtggagattc ttactccgcc gcaagcgatt    660
aaagtgttga ggacaatcgg acagcttcac ctccgtctga gagacagaga ccaagaaaga    720
gcttaaaaaa aaagatactt aatttgcttt gctctgcttc ttcaacaacg atggagtcat    780
cactaatttt tgttttcgg gctcaaccac ttgatcctga gatttagatt tccttttggt     840
gatttatgat ttttaaaaga tttgagaatt gggcttttttt gtttgtagtg atatgatgtc    900 atgttttta tttttggctt ctcgtttctt ccttaaatca gttcttacta aatctcatca    960
gttactttt                                                             969

<210> SEQ ID NO 60
<211> LENGTH: 230
<212> TYPE: PRT
<213> ORGANISM: Arabidopsis thaliana

<400> SEQUENCE: 60

Met Pro Asn Thr Ser Ser Ser Gln Ser Phe Thr Ile Phe Val Asp Gly
1               5                   10                  15

Trp Leu Ile Arg His Arg Tyr Phe Val Glu Gln Leu Met Cys Ala Ser
            20                  25                  30

Ser Leu Asp Glu Thr Asn Arg Ile Ser Leu Glu Glu Gln Gln Ser Leu
        35                  40                  45

Val Ala Gln Phe Leu Ser His Cys Leu Gln Tyr Tyr Gln Glu Lys Phe
    50                  55                  60

Ala Ser Val Ser Leu Ala Gly Asp Asn Val Phe Thr Phe Phe Cys Pro
65                  70                  75                  80

Pro Trp Phe Asn Ser Tyr Ala Lys Leu Ile Leu Trp Val Gly Asp Phe
                85                  90                  95

Lys Pro Ser Leu Val Phe Lys Leu Thr Glu Val Ser Val Ala Asp Leu
            100                 105                 110

Thr Arg His Gln Lys Asp Arg Ile Ser Ser Leu Lys Ser Glu Thr Arg
        115                 120                 125

```
Arg Lys Glu Arg Glu Val Met Arg Asp Phe Ala Leu Val Gln Gln Ser
    130                 135                 140

Val Ala Asp Pro Pro Val Met Leu Ala Ala Arg Arg Val Gly Ala Val
145                 150                 155                 160

Gly Met Val Asp Gly Glu Glu Thr Asp Leu Glu Glu Ala Met Glu Val
                165                 170                 175

Leu Lys Ala Gly Met Ala Ala Ala Met Asn Asn Ala Asp Gln Leu Arg
            180                 185                 190

Cys Ser Thr Val Gly Lys Val Val Glu Ile Leu Thr Pro Pro Gln Ala
        195                 200                 205

Ile Lys Val Leu Arg Thr Ile Gly Gln Leu His Leu Arg Leu Arg Asp
    210                 215                 220

Arg Asp Gln Glu Arg Ala
225                 230

<210> SEQ ID NO 61
<211> LENGTH: 1974
<212> TYPE: DNA
<213> ORGANISM: Arabidopsis thaliana

<400> SEQUENCE: 61
```

| | | | | | |
|---|---|---|---|---|---|
| aagcttttc | actctctcta | cgccacgacg | actgtgaagc | gagaaatggc | tacttccgat | 60 |
| caagatcgcc | gtcacagagt | cactcgcaac | cgtccaccaa | tagctcgacc | ctctacttct | 120 |
| tcatctcgtc | ccgttgtatc | tcctcctaga | tcaaaagttt | cgaagcgtgt | gcttctccgt | 180 |
| gtagcttccg | tcgcatgcgg | gattcaattc | ggatgggctc | ttcagctttc | tctcctcaca | 240 |
| ccttacgttc | aagagctggg | gatcccacac | gcttgggcta | gtgtgatttg | gctttgcggt | 300 |
| cctctctctg | gtttgttcgt | gcaaccgctc | gttgggcata | gtagcgatag | gtgtactagt | 360 |
| aagtacggtc | gtcggagacc | gtttattgtc | gccggagctg | tggcgatttc | tatctctgtt | 420 |
| atggttattg | gtcatgcggc | ggatattgga | tgggcatttg | gggatagaga | agggaagatt | 480 |
| aagccgaggg | cgattgttgc | ttttgtttta | gggttttgga | ttcttgatgt | tgctaataat | 540 |
| atgactcaag | gtccttgtag | agctctcctt | gctgatctta | ctgagaatga | taatcgcaga | 600 |
| acccgagttg | caaatggcta | cttctctctc | tttatggctg | ttggcaatgt | tcttggctat | 660 |
| gctactggat | catacaatgg | ttggtacaag | atcttcactt | ttacgaagac | agttgcatgt | 720 |
| aatgtggaat | gtgccaatct | caagtctgcc | ttctacatag | atgttgtctt | tattgcaata | 780 |
| actacgatcc | taagcgtctc | agcggctcat | gaggtgccac | ttgcttcatt | ggcttctgaa | 840 |
| gcacatgggc | aaaccagtgg | aacagacgaa | gcttttcttt | ctgagatatt | tggaactttc | 900 |
| agatattttc | caggaaatgt | ttggataatc | ttgcttgtta | cagcattgac | atggattggt | 960 |
| tggtttccat | ttattctgtt | tgatactgat | tggatgggtc | gagagatcta | tggcggtgaa | 1020 |
| ccgaacatag | ggacttcata | tagtgctggg | gtcagtatgg | gtgcacttgg | tttgatgttg | 1080 |
| aattctgttt | ttcttggaat | cacttctgtg | ctcatggaga | actttgcag | aaagtggggg | 1140 |
| gctggttttg | tttggggaat | atcaaatatc | ttaatgctta | tttgctttct | tggaatgata | 1200 |
| atcacctcat | ttgttgcgtc | tcaccttggc | tacattggcc | atgaacaacc | tcctgccagc | 1260 |
| atcgtgtttg | ctgctgtgtt | aatctttaca | attctgggca | ttccattggc | gataacttac | 1320 |
| agcgtcccat | atgcgttgat | ttccatacgt | attgaatccc | tgggcttagg | tcaaggctta | 1380 |
| tctttgggtg | tgctaaattt | ggcgatagtc | atcccacagg | taattgtgtc | tgttggcagt | 1440 |
| ggcccatggg | atcaactgtt | tggaggtggg | aattcaccgg | cacttgcagt | aggagcagct | 1500 |

```
acaggcttca ttggcggaat tgtagctatc ttggctcttc cacggacaag gattcagaag    1560
cccatccctc tcccatgaga ttctctcttt tgttatataa gatgagtgtc aagcgaggaa    1620
cgcataaggg gagtgcttgg aaatggcaag gagatggaac acttaatgtg atccttgtcg    1680
aaaattcgtg caatggcttc tcgtgtgact aacttatttg cagctactag gacttaatcc    1740
cctctacttt ggggactatg atccttgtat acacgaggca ccatagaacc aatgaaaata    1800
atacatcatt cagtttgtga ggtatatgca tctctccttt attggaagtt ccagttcggg    1860
atcttctctg ttttttttgt tgttgttgta aattaatgta aaaacctgtg tacaacagag    1920
tgtttgtaag ggcccctgag ttctgtaact gtttataaag ttcatttttct ttag          1974

<210> SEQ ID NO 62
<211> LENGTH: 510
<212> TYPE: PRT
<213> ORGANISM: Arabidopsis thaliana

<400> SEQUENCE: 62

Met Ala Thr Ser Asp Gln Asp Arg Arg His Arg Val Thr Arg Asn Arg
 1               5                  10                  15

Pro Pro Ile Ala Arg Pro Ser Thr Ser Ser Arg Pro Val Val Ser
                20                  25                  30

Pro Pro Arg Ser Lys Val Ser Lys Arg Val Leu Leu Arg Val Ala Ser
            35                  40                  45

Val Ala Cys Gly Ile Gln Phe Gly Trp Ala Leu Gln Leu Ser Leu Leu
        50                  55                  60

Thr Pro Tyr Val Gln Glu Leu Gly Ile Pro His Ala Trp Ala Ser Val
 65                  70                  75                  80

Ile Trp Leu Cys Gly Pro Leu Ser Gly Leu Phe Val Gln Pro Leu Val
                 85                  90                  95

Gly His Ser Ser Asp Arg Cys Thr Ser Lys Tyr Gly Arg Arg Arg Pro
            100                 105                 110

Phe Ile Val Ala Gly Ala Val Ala Ile Ser Ile Ser Val Met Val Ile
        115                 120                 125

Gly His Ala Ala Asp Ile Gly Trp Ala Phe Gly Asp Arg Glu Gly Lys
    130                 135                 140

Ile Lys Pro Arg Ala Ile Val Ala Phe Val Leu Gly Phe Trp Ile Leu
145                 150                 155                 160

Asp Val Ala Asn Asn Met Thr Gln Gly Pro Cys Arg Ala Leu Leu Ala
                165                 170                 175

Asp Leu Thr Glu Asn Asp Asn Arg Arg Thr Arg Val Ala Asn Gly Tyr
            180                 185                 190

Phe Ser Leu Phe Met Ala Val Gly Asn Val Leu Gly Tyr Ala Thr Gly
        195                 200                 205

Ser Tyr Asn Gly Trp Tyr Lys Ile Phe Thr Phe Thr Lys Thr Val Ala
    210                 215                 220

Cys Asn Val Glu Cys Ala Asn Leu Lys Ser Ala Phe Tyr Ile Asp Val
225                 230                 235                 240

Val Phe Ile Ala Ile Thr Thr Ile Leu Ser Val Ser Ala Ala His Glu
                245                 250                 255

Val Pro Leu Ala Ser Leu Ala Ser Glu Ala His Gly Gln Thr Ser Gly
            260                 265                 270

Thr Asp Glu Ala Phe Leu Ser Glu Ile Phe Gly Thr Phe Arg Tyr Phe
        275                 280                 285

Pro Gly Asn Val Trp Ile Ile Leu Leu Val Thr Ala Leu Thr Trp Ile
    290                 295                 300
```

Gly Trp Phe Pro Phe Ile Leu Phe Asp Thr Asp Trp Met Gly Arg Glu
305                 310                 315                 320

Ile Tyr Gly Gly Glu Pro Asn Ile Gly Thr Ser Tyr Ser Ala Gly Val
            325                 330                 335

Ser Met Gly Ala Leu Gly Leu Met Leu Asn Ser Val Phe Leu Gly Ile
        340                 345                 350

Thr Ser Val Leu Met Glu Lys Leu Cys Arg Lys Trp Gly Ala Gly Phe
    355                 360                 365

Val Trp Gly Ile Ser Asn Ile Leu Met Ala Ile Cys Phe Leu Gly Met
    370                 375                 380

Ile Ile Thr Ser Phe Val Ala Ser His Leu Gly Tyr Ile Gly His Glu
385                 390                 395                 400

Gln Pro Pro Ala Ser Ile Val Phe Ala Ala Val Leu Ile Phe Thr Ile
            405                 410                 415

Leu Gly Ile Pro Leu Ala Ile Thr Tyr Ser Val Pro Tyr Ala Leu Ile
        420                 425                 430

Ser Ile Arg Ile Glu Ser Leu Gly Leu Gly Gln Gly Leu Ser Leu Gly
    435                 440                 445

Val Leu Asn Leu Ala Ile Val Ile Pro Gln Val Ile Val Ser Val Gly
    450                 455                 460

Ser Gly Pro Trp Asp Gln Leu Phe Gly Gly Asn Ser Pro Ala Leu
465                 470                 475                 480

Ala Val Gly Ala Ala Thr Gly Phe Ile Gly Ile Val Ala Ile Leu
            485                 490                 495

Ala Leu Pro Arg Thr Arg Ile Gln Lys Pro Ile Pro Leu Pro
            500                 505                 510

<210> SEQ ID NO 63
<211> LENGTH: 381
<212> TYPE: DNA
<213> ORGANISM: Arabidopsis thaliana

<400> SEQUENCE: 63
atggcgtcaa actcaagaag ttcaatctca ccatggacgt ttagtcaaaa caagatgttc      60
gagagggcct tggcagttta cgacaaggac acacccgacc gatggcacaa tgtggcaaaa     120
gctgtcggag ggaaaactgt agaagaagtg aagcgccact atgacattct cgtcgaggat     180
ctcatcaaca tcgagactgg tcgtgtccct tgcccaatt acaagacctt cgaatctaac      240
tcaagaagca tcaatgactt tgacacaagg tatataacta aatatctata tatgatgctc     300
tcgatatatt ttgataatca ttctagtgat tttgagaaat tctctcaaaa agttcttgta     360
agttatattt ctttggttta a                                              381

<210> SEQ ID NO 64
<211> LENGTH: 126
<212> TYPE: PRT
<213> ORGANISM: Arabidopsis thaliana

<400> SEQUENCE: 64

Met Ala Ser Asn Ser Arg Ser Ser Ile Ser Pro Trp Thr Phe Ser Gln
1               5                   10                  15

Asn Lys Met Phe Glu Arg Ala Leu Ala Val Tyr Asp Lys Asp Thr Pro
            20                  25                  30

Asp Arg Trp His Asn Val Ala Lys Ala Val Gly Gly Lys Thr Val Glu
        35                  40                  45

Glu Val Lys Arg His Tyr Asp Ile Leu Val Glu Asp Leu Ile Asn Ile

```
            50                  55                  60
Glu Thr Gly Arg Val Pro Leu Pro Asn Tyr Lys Thr Phe Glu Ser Asn
 65                  70                  75                  80

Ser Arg Ser Ile Asn Asp Phe Asp Thr Arg Tyr Ile Thr Lys Tyr Leu
                 85                  90                  95

Tyr Met Met Leu Ser Ile Tyr Phe Asp Asn His Ser Ser Asp Phe Glu
            100                 105                 110

Lys Phe Ser Gln Lys Val Leu Val Ser Tyr Ile Ser Leu Val
        115                 120                 125

<210> SEQ ID NO 65
<211> LENGTH: 1778
<212> TYPE: DNA
<213> ORGANISM: Arabidopsis thaliana

<400> SEQUENCE: 65
atttatttct ctacttgtcc acttttctac agccgcatca tccttctccc ttgtgcgata      60
tcgtttgcgt gagatttgtc tgaaaagtag ctaaccatgg gtaaagagaa gtttcacatc     120
aacattgtgg tcattggcca cgtcgattct ggaaagtcga caaccactgg acacttgatc     180
tacaagttgg gtggtattga caagcgtgtg atcgagaggt tcgagaagga ggctgctgag     240
atgaacaaga ggtccttcaa gtacgcatgg gtgttggaca aacttaaggc tgagcgtgag     300
cgtggtatca ccattgacat tgctctctgg aagttcgaga ccaccaagta ctactgcact     360
gtcattgatg ctcctggtca tcgtgatttc atcaagaaca tgatcactgg tacctcccag     420
gctgattgtg ctgtccttat cattgactcc accactggtg ttttgaggc tggtatctcc     480 aaggatggtc agacccgtga gcacgctctc cttgctttca cccttggtgt caagcagatg     540
atctgctgtt gtaacaagat ggatgccact accccccaagt actccaaggc caggtacgat     600
gaaatcatca aggaggtgtc ttcctacttg aagaaggttg gttacaaccc cgacaaaatc     660
ccatttgtgc ccatctctgg atttgagggt gacaacatga ttgagaggtc caccaacctt     720
gactggtaca agggaccaac tctccttgag gctcttgacc agatcaacga gcccaagagg     780
ccgtcagaca agccccttcg tctcccactt caggatgtct acaagattgg tggtattgga     840
acggtgccag tgggacgtgt tgagactggt atgatcaagc tggtatggt gtgacctt     900 gctcccacag gattgaccac tgaggtcaag tctgttgaga tgcaccacga gtctcttctt     960
gaggcacttc aggtgacaa cgttgggttc aatgttaaga atgttgccgt gaaggatctt    1020
aagagagggt acgtcgcctc caactccaag gatgaccctg ccaagggtgc tgctaacttc    1080
acctcccagg tcatcatcat gaaccacccct ggtcagattg gtaacggtta cgccccagtc    1140
ttggattgcc acacctctca cattgcagtc aagttctctg agatcttgac caagattgac    1200
aggcgttctg gtaaggagat tgagaaggag cccaaattct tgaagaatgg tgatgctggt    1260
atggtgaaga tgactccaac caagcccatg gttgtggaga ccttctctga gtacccacca    1320
cttggacgtt tcgctgttag ggacatgagg cagactgttg cagtcggtgt tatcaagagt    1380
gttgacaaga aggacccaac cggagccaag gttaccaagg ctgcagttaa gaagggtgca    1440
aagtgaactc gaatcctcaa aactctatcc gcagatgaat caaaaaacaa tattagtttc    1500
tttactttag tttggtattt ggtcgcgtgt tatagcttcg tttcttctcc atcggaactc    1560
tgttcccgga actgggttct tgatcggagg tggcggagct actttgcacc tattttgctt    1620
ttgaattgtt atcaatttg aacctatttg gagattcggt tatatgatgt gattttccga    1680
ggatattctc tcttttttg ttgcgtgtat cacattcgaa ttcagtctct tggataactt    1740
```

```
gtggaaaaac ttataacttc aagaaaaacc ttataaac                              1778
```

<210> SEQ ID NO 66
<211> LENGTH: 449
<212> TYPE: PRT
<213> ORGANISM: Arabidopsis thaliana

<400> SEQUENCE: 66

```
Met Gly Lys Glu Lys Phe His Ile Asn Ile Val Val Ile Gly His Val
1               5                   10                  15

Asp Ser Gly Lys Ser Thr Thr Thr Gly His Leu Ile Tyr Lys Leu Gly
            20                  25                  30

Gly Ile Asp Lys Arg Val Ile Glu Arg Phe Glu Lys Glu Ala Ala Glu
        35                  40                  45

Met Asn Lys Arg Ser Phe Lys Tyr Ala Trp Val Leu Asp Lys Leu Lys
    50                  55                  60

Ala Glu Arg Glu Arg Gly Ile Thr Ile Asp Ile Ala Leu Trp Lys Phe
65                  70                  75                  80

Glu Thr Thr Lys Tyr Tyr Cys Thr Val Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Ile Asp Ser Thr Thr Gly Gly Phe Glu Ala Gly Ile Ser
        115                 120                 125

Lys Asp Gly Gln Thr Arg Glu His Ala Leu Leu Ala Phe Thr Leu Gly
    130                 135                 140

Val Lys Gln Met Ile Cys Cys Cys Asn Lys Met Asp Ala Thr Thr Pro
145                 150                 155                 160

Lys Tyr Ser Lys Ala Arg Tyr Asp Glu Ile Ile Lys Glu Val Ser Ser
                165                 170                 175

Tyr Leu Lys Lys Val Gly Tyr Asn Pro Asp Lys Ile Pro Phe Val Pro
            180                 185                 190

Ile Ser Gly Phe Glu Gly Asp Asn Met Ile Glu Arg Ser Thr Asn Leu
        195                 200                 205

Asp Trp Tyr Lys Gly Pro Thr Leu Leu Glu Ala Leu Asp Gln Ile Asn
    210                 215                 220

Glu Pro Lys Arg Pro Ser Asp Lys Pro Leu Arg Leu Pro Leu Gln Asp
225                 230                 235                 240

Val Tyr Lys Ile Gly Gly Ile Gly Thr Val Pro Val Gly Arg Val Glu
                245                 250                 255

Thr Gly Met Ile Lys Pro Gly Met Val Val Thr Phe Ala Pro Thr Gly
            260                 265                 270

Leu Thr Thr Glu Val Lys Ser Val Glu Met His His Glu Ser Leu Leu
        275                 280                 285

Glu Ala Leu Pro Gly Asp Asn Val Gly Phe Asn Val Lys Asn Val Ala
    290                 295                 300

Val Lys Asp Leu Lys Arg Gly Tyr Val Ala Ser Asn Ser Lys Asp Asp
305                 310                 315                 320

Pro Ala Lys Gly Ala Ala Asn Phe Thr Ser Gln Val Ile Ile Met Asn
                325                 330                 335

His Pro Gly Gln Ile Gly Asn Gly Tyr Ala Pro Val Leu Asp Cys His
            340                 345                 350

Thr Ser His Ile Ala Val Lys Phe Ser Glu Ile Leu Thr Lys Ile Asp
        355                 360                 365

Arg Arg Ser Gly Lys Glu Ile Glu Lys Glu Pro Lys Phe Leu Lys Asn
```

```
                    370             375             380
Gly Asp Ala Gly Met Val Lys Met Thr Pro Thr Lys Pro Met Val Val
385                 390                 395                 400

Glu Thr Phe Ser Glu Tyr Pro Pro Leu Gly Arg Phe Ala Val Arg Asp
                405                 410                 415

Met Arg Gln Thr Val Ala Val Gly Val Ile Lys Ser Val Asp Lys Lys
                420                 425                 430

Asp Pro Thr Gly Ala Lys Val Thr Lys Ala Ala Val Lys Lys Gly Ala
                435                 440                 445

Lys

<210> SEQ ID NO 67
<211> LENGTH: 731
<212> TYPE: DNA
<213> ORGANISM: Arabidopsis thaliana

<400> SEQUENCE: 67
gcgtctctcc tctctctgtt tcttttcttt ttgtttcatt ttcttatctc ctcacactct      60
tcgaacaagg aagaaccta atctcaagat gaatagggag aagttgatga agatggctaa     120
taccgtccgc actggcggaa agggtactgt cagaagaaag aagaaggctg tgcacaagac     180
caatacaact gatgacaaga ggcttcaaag cactcttaag agaattggag ttaactccat     240
tcccgctatt gaagaagtta acatctttaa ggatgatgtt gttattcagt tcatcaaccc     300
taaggttcaa gcttcaattg ctgcaaacac atgggttgtt agcggttctc ctcagaccaa     360
aaaattgcaa gatatccttc ctcagatcat cagccaactt ggaccagaca acatggacaa     420
cctgaagaag ctagcagaac agttccgaaa acaggcttct ggtgaaggta atgccgcctc     480
agcaaccata caagaagagg atgatgacga tgtcccagag cttgttggag agacattcga     540
aactgctgct gaagagaaag caccagctgc tgctgcttct tcttagagag aaaagagcga     600
gaccacatcc aaaaaaaaac cgcactttga ttttacata tctttataat atgtttgttc     660
gctcgatcct ttttgtagtt tccgaccaga atcttgtttt ccatctaatg acttaaggtt     720
tttatccaat t                                                          731

<210> SEQ ID NO 68
<211> LENGTH: 165
<212> TYPE: PRT
<213> ORGANISM: Arabidopsis thaliana

<400> SEQUENCE: 68

Met Asn Arg Glu Lys Leu Met Lys Met Ala Asn Thr Val Arg Thr Gly
1               5                   10                  15

Gly Lys Gly Thr Val Arg Arg Lys Lys Lys Ala Val His Lys Thr Asn
                20                  25                  30

Thr Thr Asp Asp Lys Arg Leu Gln Ser Thr Leu Lys Arg Ile Gly Val
            35                  40                  45

Asn Ser Ile Pro Ala Ile Glu Glu Val Asn Ile Phe Lys Asp Asp Val
        50                  55                  60

Val Ile Gln Phe Ile Asn Pro Lys Val Gln Ala Ser Ile Ala Ala Asn
65                  70                  75                  80

Thr Trp Val Val Ser Gly Ser Pro Gln Thr Lys Lys Leu Gln Asp Ile
                85                  90                  95

Leu Pro Gln Ile Ile Ser Gln Leu Gly Pro Asp Asn Met Asp Asn Leu
            100                 105                 110

Lys Lys Leu Ala Glu Gln Phe Gln Lys Gln Ala Ser Gly Glu Gly Asn
```

```
                115                  120                 125
Ala Ala Ser Ala Thr Ile Gln Glu Glu Asp Asp Asp Val Pro Glu
        130                 135             140

Leu Val Gly Glu Thr Phe Glu Thr Ala Ala Glu Glu Lys Ala Pro Ala
145                 150                 155                 160

Ala Ala Ala Ser Ser
            165

<210> SEQ ID NO 69
<211> LENGTH: 452
<212> TYPE: DNA
<213> ORGANISM: Arabidopsis thaliana

<400> SEQUENCE: 69
agattcgata ccgtctgcaa ctctcagcta cttttcccc aattttgagc tcaacatcga      60
accctagctc aacgaaccaa tcatgtcttc caagcaagga ggaaaggcga aacctttgaa    120
gcagcctaaa gctgataaga aggaatacga cgagactgac ttagctaaca ttcagaagaa    180
gaaagatgag gaaaaggccc ttaaagagct tagagccaag gcatcgcaga agggatcctt    240
tggaggttct ggacttaaga gagtggcaa gaaatgatcc gttttatcca tgaagtgtgt    300
tttaaaatgc aaatttatca agtgaaaaaa acagataatc ctgtgttgat gtaactttt    360 atcataattc gagaagagta acttcgcttc tccatacata tgtttgcttt ctccattttt    420
tcatgaaaaa gaaaagtggt atctacccta aa                                 452

<210> SEQ ID NO 70
<211> LENGTH: 64
<212> TYPE: PRT
<213> ORGANISM: Arabidopsis thaliana

<400> SEQUENCE: 70

Met Ser Ser Lys Gln Gly Gly Lys Ala Lys Pro Leu Lys Gln Pro Lys
1               5                   10                  15

Ala Asp Lys Lys Glu Tyr Asp Glu Thr Asp Leu Ala Asn Ile Gln Lys
            20                  25                  30

Lys Lys Asp Glu Glu Lys Ala Leu Lys Glu Leu Arg Ala Lys Ala Ser
        35                  40                  45

Gln Lys Gly Ser Phe Gly Gly Ser Gly Leu Lys Lys Ser Gly Lys Lys
    50                  55                  60

<210> SEQ ID NO 71
<211> LENGTH: 1297
<212> TYPE: DNA
<213> ORGANISM: Arabidopsis thaliana

<400> SEQUENCE: 71
actctcaaaa tcatcttctt cacccaaaaa cccctaaaag ccttatccct tcttcttccc      60
atggctgctt cagcttcgtc tctcgctctc tcttccttca accctaaatc tcttcctttc    120
ggcgtctcca gacctgcctc cgtttccctc ttatctcctt ccctctcctt taaactcaat    180
tccgactccg tttccttctc catcgccgcc aaatggaact ctcccgcttc tcgcttcgcc    240
cgtaacgttg cgattacctc agagttcgag gtggaagaag atggtttcgc tgacgtcgct    300
ccgccaaaag agcaatcttt ctctgctgac cttaaactct tcgttggtaa ccttcctttc    360
aacgttgaca gtgctcagct cgctcagctc tttgagagtg ccggaaatgt tgagatggtt    420
gaggtaatct atgacaaaat tacaggaaga agcagaggtt ttggattcgt gactatgtct    480
tcagtttctg aagttgaggc agctgctcag cagttcaatg gctatgagtt ggatggtaga    540
```

-continued

```
ccttttgagag tcaatgctgg tcccccacca ccaaagaggg aagatggttt ctccagagga    600
cctaggagca gctttggaag ctcaggttct ggatatggag gaggtggtgg ttctggtgct    660
ggttcaggaa accgtgttta tgtgggtaac ctctcttggg gagttgatga catggctctt    720
gagagtttgt tctcggagca aggaaaggtt gttgaggcca gagtcatcta cgacagggac    780
agtggtcgat ccaagggttt tggatttgtg acatacgact cttctcaaga ggtccaaaat    840
gccatcaagt ccttggatgg tgctgatttg acggtagac aaattagagt ctcggaagct    900
gaggctaggc ctccaaggcg ccaatattga gcaccaatct atgacttcct attctcaaaa    960
acgcatattc tggagggcgc ttcgaagtaa agagggtttg tgagatgatg gcagtttcag   1020
acggtactaa gctcttagct tcgcctatgt ttgttgcctt ggatgcaaga aggtcgtaaa   1080
ggaatggtct ttttttttt gagaaacgta taattaagat agaaactgga gagaccatgt   1140
tcttgtctgt ctgaatgctg ccattgactg cttcgctttg gttttgattc aatttttttt   1200
tctctctata tcgtggtctc ttcttcctaa tgcttctctg tttatttgat cctctgctca   1260
aatgaatatg aacacacttg aaaaccggtt aaaactc                             1297
```

<210> SEQ ID NO 72
<211> LENGTH: 289
<212> TYPE: PRT
<213> ORGANISM: Arabidopsis thaliana

<400> SEQUENCE: 72

```
Met Ala Ala Ser Ala Ser Ser Leu Ala Leu Ser Ser Phe Asn Pro Lys
1               5                  10                  15

Ser Leu Pro Phe Gly Val Ser Arg Pro Ala Ser Val Ser Leu Leu Ser
            20                  25                  30

Pro Ser Leu Ser Phe Lys Leu Asn Ser Asp Ser Val Ser Phe Ser Ile
        35                  40                  45

Ala Ala Lys Trp Asn Ser Pro Ala Ser Arg Phe Ala Arg Asn Val Ala
    50                  55                  60

Ile Thr Ser Glu Phe Glu Val Glu Glu Asp Gly Phe Ala Asp Val Ala
65                  70                  75                  80

Pro Pro Lys Glu Gln Ser Phe Ser Ala Asp Leu Lys Leu Phe Val Gly
                85                  90                  95

Asn Leu Pro Phe Asn Val Asp Ser Ala Gln Leu Ala Gln Leu Phe Glu
            100                 105                 110

Ser Ala Gly Asn Val Glu Met Val Glu Val Ile Tyr Asp Lys Ile Thr
        115                 120                 125

Gly Arg Ser Arg Gly Phe Gly Phe Val Thr Met Ser Ser Val Ser Glu
    130                 135                 140

Val Glu Ala Ala Ala Gln Gln Phe Asn Gly Tyr Glu Leu Asp Gly Arg
145                 150                 155                 160

Pro Leu Arg Val Asn Ala Gly Pro Pro Pro Lys Arg Glu Asp Gly
                165                 170                 175

Phe Ser Arg Gly Pro Arg Ser Ser Phe Gly Ser Ser Gly Ser Gly Tyr
            180                 185                 190

Gly Gly Gly Gly Gly Ser Gly Ala Gly Ser Gly Asn Arg Val Tyr Val
        195                 200                 205

Gly Asn Leu Ser Trp Gly Val Asp Asp Met Ala Leu Glu Ser Leu Phe
    210                 215                 220

Ser Glu Gln Gly Lys Val Val Glu Ala Arg Val Ile Tyr Asp Arg Asp
225                 230                 235                 240
```

```
Ser Gly Arg Ser Lys Gly Phe Gly Phe Val Thr Tyr Asp Ser Ser Gln
                245                 250                 255

Glu Val Gln Asn Ala Ile Lys Ser Leu Asp Gly Ala Asp Leu Asp Gly
            260                 265                 270

Arg Gln Ile Arg Val Ser Glu Ala Glu Ala Arg Pro Pro Arg Arg Gln
        275                 280                 285

Tyr

<210> SEQ ID NO 73
<211> LENGTH: 937
<212> TYPE: DNA
<213> ORGANISM: Arabidopsis thaliana

<400> SEQUENCE: 73
atttgtgcct actcatttcc tccaaacgtc aaacatagca gcagccatgg ctgccaccaa      60
cacaatcctc gcattctcat ctccttctcg tcttctcatt cctccttcct ccaatccttc     120
aactctccgt tcctctttcc gcggcgtctc tctcaacaac aacaatctcc accgtctcca     180
atctgtttcc ttcgccgtta agctccgtcg aaagcgttg acagttgttt ccgcggcgaa      240
gaaggctgtt gcagtgctta aaggtacttc tgatgtcgaa ggagttgtta ctttgaccca     300
agatgactca ggtcctacaa ctgtgaatgt tcgtatcact ggtctcactc cagggcctca     360
tggatttcat ctccatgagt ttggtgatac aactaatgga tgtatctcaa caggaccaca     420
tttcaaccct aacaacatga cacacggagc tccagaagat gagtgccgtc atgcgggtga     480
cctgggaaac ataaatgcca atgccgatgg cgtggcagaa acaacaatag tggacaatca     540
gattcctctg actggtccta attctgttgt tggaagagcc tttgtggttc acgagcttaa     600
ggatgacctc ggaaagggtg gccatgagct tagtctgacc actggaaacg caggcgggag     660
attggcatgt ggtgtgattg gcttgacgcc gctctaagtc agaggctaag caagtactct     720
tatgtctact gtgttgatct tgtctgtttg aacagatgta agaatcttag caaataatgt     780
ttggcttaat aaactttgat gtttatgttc attgcatcaa ttttctctt tttgaatttg      840 tgacagtgat gtgtttactt ttgatacaac tttgtgtttg atcgtttaag tacattttgg     900
tttatttagc atcctttta ttcagttcaa gattgtg                               937

<210> SEQ ID NO 74
<211> LENGTH: 216
<212> TYPE: PRT
<213> ORGANISM: Arabidopsis thaliana

<400> SEQUENCE: 74

Met Ala Ala Thr Asn Thr Ile Leu Ala Phe Ser Ser Pro Ser Arg Leu
1               5                   10                  15

Leu Ile Pro Pro Ser Ser Asn Pro Ser Thr Leu Arg Ser Ser Phe Arg
            20                  25                  30

Gly Val Ser Leu Asn Asn Asn Leu His Arg Leu Gln Ser Val Ser
        35                  40                  45

Phe Ala Val Lys Ala Pro Ser Lys Ala Leu Thr Val Val Ser Ala Ala
    50                  55                  60

Lys Lys Ala Val Ala Val Leu Lys Gly Thr Ser Asp Val Glu Gly Val
65                  70                  75                  80

Val Thr Leu Thr Gln Asp Asp Ser Gly Pro Thr Val Asn Val Arg
                85                  90                  95

Ile Thr Gly Leu Thr Pro Gly Pro His Gly Phe His Leu His Glu Phe
            100                 105                 110
```

```
Gly Asp Thr Thr Asn Gly Cys Ile Ser Thr Gly Pro His Phe Asn Pro
        115                 120                 125
Asn Asn Met Thr His Gly Ala Pro Glu Asp Glu Cys Arg His Ala Gly
    130                 135                 140
Asp Leu Gly Asn Ile Asn Ala Asn Ala Asp Gly Val Ala Glu Thr Thr
145                 150                 155                 160
Ile Val Asp Asn Gln Ile Pro Leu Thr Gly Pro Asn Ser Val Val Gly
                165                 170                 175
Arg Ala Phe Val Val His Glu Leu Lys Asp Asp Leu Gly Lys Gly Gly
            180                 185                 190
His Glu Leu Ser Leu Thr Thr Gly Asn Ala Gly Gly Arg Leu Ala Cys
        195                 200                 205
Gly Val Ile Gly Leu Thr Pro Leu
    210                 215

<210> SEQ ID NO 75
<211> LENGTH: 2150
<212> TYPE: DNA
<213> ORGANISM: Arabidopsis thaliana

<400> SEQUENCE: 75
gtgcgataat ggccatggca gagctctcaa cccccaaaac gacgtcgcct tttctcaact     60
cttcgtctcg gcttcgtctc tcttcaaaat tgcaccttc  aaaccacttt cgccatcttc    120
ttcttccacc tctccacaca acaactccca actccaaaat ctcttgctcc gtttctcaaa    180
agtaaccaag ctcctgttgc tgtgcaagaa aatggattgg tgaagacgaa gaaagagtgt    240
tatggagtgt tctgcctcac ctatgatctt aaagctgaag aagagacaag atcatggaag    300
aagttaatta atattgcagt ttcaggtgct gcaggaatga tttctaacca tcttctcttc    360
aaacttgctt caggggaagt atttggtcca gatcaaccca ttgcattgaa actgctagga    420
tcagagagat caattcaagc tcttgaaggt gttgcaatgg aactggagga ttcattgttc    480
ccattgttga gagaagttga tataggaaca gatccaaatg aagtgttcca agatgtggag    540
tgggctattc tgattggagc aaaacctcga ggccctggaa tggaacgtgc tgacttgttg    600
gacatcaatg gccaaatctt tgctgagcag ggcaaagctc tgaacaaagc tgcctctcct    660
aacgtcaagg ttcttgtagt gggaaaccct tgcaacacca tgccttgat  ttgtcttaaa    720
aatgctccca acattcctgc aaagaacttc catgccctca cgaggttaga cgaaaatcgt    780
gccaaatgcc agcttgctct taaagccggt gttttctatg acaaagtgtc taatatgacc    840
atatggggaa atcactccac gactcaggtg ccagacttct taaatgccag aattaatggc    900
ctgcctgtga aggaggttat tacagatcac aaatggttag aagagggatt cactgagagt    960
gtgcagaaga gaggtgggtt attaattcag aaatgggtc  gatcttctgc tgcttctact   1020
gctgttttcca ttgttgatgc tataaagtct cttgtaactc ctactcctga gggtgattgg   1080
ttttcgactg gggtgtacac ggatggaaat ccttatggta ttgaagaggg ccttgtcttc   1140
agtatgccat gccggtcgaa gggagatgga gattatgaac ttgtcaagga tgtagaaatt   1200
gatgactacc ttcgccaacg aatcgccaag tcggaagcgg aactgttggc tgagaagaga   1260
tgtgttgcac acctcactgg agagggcatt gcctactgtg atcttggtcc ggtagatact   1320
atgcttcctg gggaagtttg attttgcag  gacgttgaac atctcaagta agcattctct   1380
tccgggttgt tagctgtaca gagcacagcc acattactta tgattattgt tcagaataag   1440
aaaatgaaac tcttatttct tatttacatg catctgtatg tgattttct  tgagcaatgc   1500
tccaaaagtc atatacagta gtatttgtaa acacttgaaa cgttctatg  ctttattcca   1560
```

```
gtttcagaac tcaaactaga taatgcatag ctaatatcaa acacaaatct tatgagcttt    1620 ttctttttcca caaaccaatc tcaaaacagc tccctatatg tgaaagtatc accaacaaag   1680
ttacaaagag tatatactgt acacaagaat taagaagcaa gaatggatga tggtcttgtt    1740
ggtggatgcc ctgaaaaggc tatgcgtagt ctcttgtatt cgtctctgga gtagtctagt    1800
gaaaaacaga gctgtcttat cacttccctc ttctcttctg ctacttcttc tagttccctc    1860
ctctgcttct ccacctcctt ctccatctcc atagtcctat cgtctctcgc tttttatttca   1920 cttccaagtc gacttatctc cgactctagc tcactcacct ttctgcttaa cgtctctatg    1980
catctccctt tctctacctt ttccagtgtc agcacctcga tttcgctctt cagcttttcc    2040
tcctcttcta ttttctcatt gttcaccttt cttctctcat cttcaagata acgcacattg    2100
gcttccagct ctttgaattg gtcatcccgg tgtatttttt cttccaacag              2150
```

<210> SEQ ID NO 76
<211> LENGTH: 334
<212> TYPE: PRT
<213> ORGANISM: Arabidopsis thaliana

<400> SEQUENCE: 76

```
Met Ile Ser Asn His Leu Leu Phe Lys Leu Ala Ser Gly Glu Val Phe
1               5                   10                  15

Gly Pro Asp Gln Pro Ile Ala Leu Lys Leu Leu Gly Ser Glu Arg Ser
            20                  25                  30

Ile Gln Ala Leu Glu Gly Val Ala Met Glu Leu Glu Asp Ser Leu Phe
        35                  40                  45

Pro Leu Leu Arg Glu Val Asp Ile Gly Thr Asp Pro Asn Glu Val Phe
    50                  55                  60

Gln Asp Val Glu Trp Ala Ile Leu Ile Gly Ala Lys Pro Arg Gly Pro
65                  70                  75                  80

Gly Met Glu Arg Ala Asp Leu Leu Asp Ile Asn Gly Gln Ile Phe Ala
                85                  90                  95

Glu Gln Gly Lys Ala Leu Asn Lys Ala Ala Ser Pro Asn Val Lys Val
            100                 105                 110

Leu Val Val Gly Asn Pro Cys Asn Thr Asn Ala Leu Ile Cys Leu Lys
        115                 120                 125

Asn Ala Pro Asn Ile Pro Ala Lys Asn Phe His Ala Leu Thr Arg Leu
    130                 135                 140

Asp Glu Asn Arg Ala Lys Cys Gln Leu Ala Leu Lys Ala Gly Val Phe
145                 150                 155                 160

Tyr Asp Lys Val Ser Asn Met Thr Ile Trp Gly Asn His Ser Thr Thr
                165                 170                 175

Gln Val Pro Asp Phe Leu Asn Ala Arg Ile Asn Gly Leu Pro Val Lys
            180                 185                 190

Glu Val Ile Thr Asp His Lys Trp Leu Glu Gly Phe Thr Glu Ser
        195                 200                 205

Val Gln Lys Arg Gly Gly Leu Leu Ile Gln Lys Trp Gly Arg Ser Ser
    210                 215                 220

Ala Ala Ser Thr Ala Val Ser Ile Val Asp Ala Ile Lys Ser Leu Val
225                 230                 235                 240

Thr Pro Thr Pro Glu Gly Asp Trp Phe Ser Thr Gly Val Tyr Thr Asp
                245                 250                 255

Gly Asn Pro Tyr Gly Ile Glu Gly Leu Val Phe Ser Met Pro Cys
            260                 265                 270
```

```
Arg Ser Lys Gly Asp Gly Asp Tyr Glu Leu Val Lys Asp Val Glu Ile
    275                 280                 285

Asp Asp Tyr Leu Arg Gln Arg Ile Ala Lys Ser Glu Ala Glu Leu Leu
    290                 295                 300

Ala Glu Lys Arg Cys Val Ala His Leu Thr Gly Glu Gly Ile Ala Tyr
305                 310                 315                 320

Cys Asp Leu Gly Pro Val Asp Thr Met Leu Pro Gly Glu Val
                325                 330

<210> SEQ ID NO 77
<211> LENGTH: 2175
<212> TYPE: DNA
<213> ORGANISM: Arabidopsis thaliana

<400> SEQUENCE: 77
```

| | | | | | |
|---|---|---|---|---|---|
| ctgaaatctc | actttcacag | tttgtgtctg | tgcgataatg | gccatggcag | agctctcaac | 60 |
| ccccaaaacg | acgtcgcctt | ttctcaactc | ttcgtctcgg | cttcgtctct | cttcaaaatt | 120 |
| gcacctttca | aaccactttc | gccatcttct | tcttccacct | ctccacacaa | caactcccaa | 180 |
| ctccaaaatc | tcttgctccg | tttctcaaaa | ccaagctcct | gttgctgtgc | aagaaaatgg | 240 |
| attggtgaag | acgaagaaag | agtgttatgg | agtgttctgc | ctcacctatg | atcttaaagc | 300 |
| tgaagaagag | acaagatcat | ggaagaagtt | aattaatatt | gcagtttcag | gtgctgcagg | 360 |
| aatgatttct | aaccatcttc | tcttcaaact | tgcttcaggg | gaagtatttg | gtccagatca | 420 |
| acccattgca | ttgaaactgc | taggatcaga | gagatcaatt | caagctcttg | aaggtgttgc | 480 |
| aatggaactg | gaggattcat | tgttcccatt | gttgagagaa | gttgatatag | aacagatcc | 540 |
| aaatgaagtg | ttccaagatg | tggagtgggc | tattctgatt | ggagcaaaac | ctcgaggccc | 600 |
| tggaatggaa | cgtgctgact | tgttggacat | caatggccaa | atctttgctg | agcagggcaa | 660 |
| agctctgaac | aaagctgcct | ctcctaacgt | caaggttctt | gtagtgggaa | acccttgcaa | 720 |
| caccaatgcc | ttgatttgtc | ttaaaaatgc | tcccaacatt | cctgcaaaga | acttccatgc | 780 |
| cctcacgagg | ttagacgaaa | atcgtgccaa | atgccagctt | gctcttaaag | ccggtgtttt | 840 |
| ctatgacaaa | gtgtctaata | tgaccatatg | gggaaatcac | tccacgactc | aggtgccaga | 900 |
| cttcttaaat | gccagaatta | atggcctgcc | tgtgaaggag | gttattacag | atcacaaatg | 960 |
| gttagaagag | ggattcactg | agagtgtgca | gaagagaggt | gggttattaa | ttcagaaatg | 1020 |
| gggtcgatct | tctgctgctt | ctactgctgt | ttccattgtt | gatgctataa | agtctcttgt | 1080 |
| aactcctact | cctgagggtg | attggttttc | gactggggtg | tacacggatg | gaaatcctta | 1140 |
| tggtattgaa | gagggccttg | tcttcagtat | gccatgccgg | tcgaagggag | atggagatta | 1200 |
| tgaacttgtc | aaggatgtag | aaattgatga | ctaccttcgc | caacgaatcg | ccaagtcgga | 1260 |
| agcggaactg | ttggctgaga | agagatgtgt | tgcacacctc | actggagagg | gcattgccta | 1320 |
| ctgtgatctt | ggtccggtag | atactatgct | tcctggggaa | gtttgatttt | tgcaggacgt | 1380 |
| tgaacatctc | aagtaagcat | tctcttccgg | gttgttagct | gtacagagca | cagccacatt | 1440 |
| acttatgatt | attgttcaga | ataagaaaat | gaaactctta | tttcttattt | acatgcatct | 1500 |
| gtatgtgatt | tttcttgagc | aatgctccaa | aagtcatata | cagtagtatt | tgtaaacact | 1560 |
| tgaaacgttt | ctatgctta | ttccagtttc | agaactcaaa | ctagataatg | catagctaat | 1620 |
| atcaaacaca | aatcttatga | gcttttcctt | ttccacaaac | caatctcaaa | acagctccct | 1680 |
| atatgtgaaa | gtatcaccaa | caaagttaca | aagagtatat | actgtacaca | agaattaaga | 1740 |
| agcaagaatg | gatgatggtc | ttgttggtgg | atgccctgaa | aaggctatgc | gtagtctctt | 1800 |

```
gtattcgtct ctggagtagt ctagtgaaaa acagagctgt cttatcactt ccctcttctc    1860
ttctgctact tcttctagtt ccctcctctg cttctccacc tccttctcca tctccatagt    1920
cctatcgtct ctcgctttta tttcacttcc aagtcgactt atctccgact ctagctcact    1980 caccttttctg cttaacgtct ctatgcatct ccctttctct accttttcca gtgtcagcac    2040
ctcgatttcg ctcttcagct tttcctcctc ttctattttc tcattgttca cctttcttct    2100
ctcatcttca agataacgca cattggcttc cagctctttg aattggtcat cccggtgtat    2160
tttttcttcc aacag                                                     2175
```

```
<210> SEQ ID NO 78
<211> LENGTH: 442
<212> TYPE: PRT
<213> ORGANISM: Arabidopsis thaliana

<400> SEQUENCE: 78

Met Ala Met Ala Glu Leu Ser Thr Pro Lys Thr Thr Ser Pro Phe Leu
1               5                   10                  15

Asn Ser Ser Arg Leu Arg Leu Ser Ser Lys Leu His Leu Ser Asn
            20                  25                  30

His Phe Arg His Leu Leu Leu Pro Leu His Thr Thr Thr Pro Asn
        35                  40                  45

Ser Lys Ile Ser Cys Ser Val Ser Gln Asn Gln Ala Pro Val Ala Val
    50                  55                  60

Gln Glu Asn Gly Leu Val Lys Thr Lys Lys Glu Cys Tyr Gly Val Phe
65                  70                  75                  80

Cys Leu Thr Tyr Asp Leu Lys Ala Glu Glu Thr Arg Ser Trp Lys
                85                  90                  95

Lys Leu Ile Asn Ile Ala Val Ser Gly Ala Ala Gly Met Ile Ser Asn
            100                 105                 110

His Leu Leu Phe Lys Leu Ala Ser Gly Glu Val Phe Gly Pro Asp Gln
        115                 120                 125

Pro Ile Ala Leu Lys Leu Leu Gly Ser Glu Arg Ser Ile Gln Ala Leu
    130                 135                 140

Glu Gly Val Ala Met Glu Leu Glu Asp Ser Leu Phe Pro Leu Leu Arg
145                 150                 155                 160

Glu Val Asp Ile Gly Thr Asp Pro Asn Glu Val Phe Gln Asp Val Glu
                165                 170                 175

Trp Ala Ile Leu Ile Gly Ala Lys Pro Arg Gly Pro Gly Met Glu Arg
            180                 185                 190

Ala Asp Leu Leu Asp Ile Asn Gly Gln Ile Phe Ala Glu Gln Gly Lys
        195                 200                 205

Ala Leu Asn Lys Ala Ala Ser Pro Asn Val Lys Val Leu Val Val Gly
    210                 215                 220

Asn Pro Cys Asn Thr Asn Ala Leu Ile Cys Leu Lys Asn Ala Pro Asn
225                 230                 235                 240

Ile Pro Ala Lys Asn Phe His Ala Leu Thr Arg Leu Asp Glu Asn Arg
                245                 250                 255

Ala Lys Cys Gln Leu Ala Leu Lys Ala Gly Val Phe Tyr Asp Lys Val
            260                 265                 270

Ser Asn Met Thr Ile Trp Gly Asn His Ser Thr Thr Gln Val Pro Asp
        275                 280                 285

Phe Leu Asn Ala Arg Ile Asn Gly Leu Pro Val Lys Glu Val Ile Thr
    290                 295                 300

Asp His Lys Trp Leu Glu Glu Gly Phe Thr Glu Ser Val Gln Lys Arg
```

```
                305                 310                 315                 320
Gly Gly Leu Leu Ile Gln Lys Trp Gly Arg Ser Ser Ala Ala Ser Thr
                    325                 330                 335

Ala Val Ser Ile Val Asp Ala Ile Lys Ser Leu Val Thr Pro Thr Pro
                340                 345                 350

Glu Gly Asp Trp Phe Ser Thr Gly Val Tyr Thr Asp Gly Asn Pro Tyr
            355                 360                 365

Gly Ile Glu Glu Gly Leu Val Phe Ser Met Pro Cys Arg Ser Lys Gly
        370                 375                 380

Asp Gly Asp Tyr Glu Leu Val Lys Asp Val Glu Ile Asp Asp Tyr Leu
385                 390                 395                 400

Arg Gln Arg Ile Ala Lys Ser Glu Ala Glu Leu Leu Ala Glu Lys Arg
                405                 410                 415

Cys Val Ala His Leu Thr Gly Glu Gly Ile Ala Tyr Cys Asp Leu Gly
                420                 425                 430

Pro Val Asp Thr Met Leu Pro Gly Glu Val
            435                 440

<210> SEQ ID NO 79
<211> LENGTH: 2235
<212> TYPE: DNA
<213> ORGANISM: Arabidopsis thaliana

<400> SEQUENCE: 79
caatcctctt tcttactact ctgtcgcttg gcgcgctctc tctccatagt tccagttctg      60
aaatctcact ttcacagttt gtgtctgtgc gataatggcc atggcagagc tctcaacccc     120
caaaacgacg tcgccttttc tcaactcttc gtctcggctt cgtctctctt caaaattgca     180
cctttcaaac cactttcgcc atcttcttct tccacctctc cacacaacaa ctcccaactc     240
caaaatctct tgctccgttt ctcaaaatag ccaagctcct gttgctgtgc aagaaaatgg     300
attggtgaag acgaagaaag agtgttatgg agtgttctgc ctcacctatg atcttaaagc     360
tgaagaagag acaagatcat ggaagaagtt aattaatatt gcagtttcag gtgctgcagg     420
aatgatttct aaccatcttc tcttcaaact tgcttcaggg gaagtatttg gtccagatca     480
acccattgca ttgaaactgc taggatcaga gagatcaatt caagctcttg aaggtgttgc     540
aatggaactg gaggattcat tgttcccatt gttgagagaa gttgatatag aacagatcc      600 aaatgaagtg ttccaagatg tggagtgggc tattctgatt ggagcaaaac ctcgaggccc     660
tggaatggaa cgtgctgact tgttggacat caatggccaa atctttgctg agcagggcaa     720
agctctgaac aaagctgcct ctcctaacgt caaggttctt gtagtgggaa acccttgcaa     780
caccaatgcc ttgatttgtc ttaaaaatgc tcccaacatt cctgcaaaga acttccatgc     840
cctcacgagg ttagacgaaa atcgtgccaa atgccagctt gctcttaaag ccggtgtttt     900
ctatgacaaa gtgtctaata tgaccatatg gggaaatcac tccacgactc aggtgccaga     960
cttcttaaat gccagaatta atggcctgcc tgtgaaggag ttattacag atcacaaatg    1020 gttagaagag ggattcactg agagtgtgca agagaggt gggttattaa ttcagaaatg     1080
gggtcgatct tctgctgctt ctactgctgt ttccattgtt gatgctataa agtctcttgt     1140
aactcctact cctgagggtg attggttttc gactggggtg tacacggatg gaaatcctta     1200
tggtattgaa gagggccttg tcttcagtat gccatgccgg tcgaagggag atggagatta     1260
tgaacttgtc aaggatgtag aaattgatga ctaccttcgc caacgaatcg ccaagtcgga     1320
agcggaactg ttggctgaga agagatgtgt tgcacacctc actggagagg gcattgccta     1380
```

```
ctgtgatctt ggtccggtag atactatgct tcctggggaa gtttgatttt tgcaggacgt   1440
tgaacatctc aagtaagcat tctcttccgg gttgttagct gtacagagca cagccacatt   1500
acttatgatt attgttcaga ataagaaaat gaaactctta tttcttattt acatgcatct   1560
gtatgtgatt tttcttgagc aatgctccaa aagtcatata cagtagtatt tgtaaacact   1620
tgaaacgttt ctatgcttta ttccagtttc agaactcaaa ctagataatg catagctaat   1680
atcaaacaca aatcttatga gcttttctt ttccacaaac caatctcaaa acagctccct     1740
atatgtgaaa gtatcaccaa caaagttaca aagagtatat actgtacaca agaattaaga   1800
agcaagaatg gatgatggtc ttgttggtgg atgccctgaa aaggctatgc gtagtctctt   1860
gtattcgtct ctggagtagt ctagtgaaaa acagagctgt cttatcactt ccctcttctc   1920
ttctgctact tcttcagtt ccctcctctg cttctccacc tccttctcca tctccatagt     1980
cctatcgtct ctcgctttta tttcacttcc aagtcgactt atctccgact ctagctcact   2040 caccttctg cttaacgtct ctatgcatct ccctttctct acctttccca gtgtcagcac    2100
ctcgatttcg ctcttcagct tttcctcctc ttctattttc tcattgttca cctttcttct   2160
ctcatcttca agataacgca cattggcttc cagctctttg aattggtcat cccggtgtat   2220
tttttcttcc aacag                                                    2235
```

<210> SEQ ID NO 80
<211> LENGTH: 443
<212> TYPE: PRT
<213> ORGANISM: Arabidopsis thaliana

<400> SEQUENCE: 80

```
Met Ala Met Ala Glu Leu Ser Thr Pro Lys Thr Thr Ser Pro Phe Leu
1               5                   10                  15

Asn Ser Ser Arg Leu Arg Leu Ser Ser Lys Leu His Leu Ser Asn
            20                  25                  30

His Phe Arg His Leu Leu Leu Pro Pro Leu His Thr Thr Thr Pro Asn
        35                  40                  45

Ser Lys Ile Ser Cys Ser Val Ser Gln Asn Ser Gln Ala Pro Val Ala
    50                  55                  60

Val Gln Glu Asn Gly Leu Val Lys Thr Lys Lys Glu Cys Tyr Gly Val
65                  70                  75                  80

Phe Cys Leu Thr Tyr Asp Leu Lys Ala Glu Glu Thr Arg Ser Trp
                85                  90                  95

Lys Lys Leu Ile Asn Ile Ala Val Ser Gly Ala Gly Met Ile Ser
                100                 105                 110

Asn His Leu Leu Phe Lys Leu Ala Ser Gly Glu Val Phe Gly Pro Asp
        115                 120                 125

Gln Pro Ile Ala Leu Lys Leu Leu Gly Ser Glu Arg Ser Ile Gln Ala
    130                 135                 140

Leu Glu Gly Val Ala Met Glu Leu Glu Asp Ser Leu Phe Pro Leu Leu
145                 150                 155                 160

Arg Glu Val Asp Ile Gly Thr Asp Pro Asn Glu Val Phe Gln Asp Val
                165                 170                 175

Glu Trp Ala Ile Leu Ile Gly Ala Lys Pro Arg Gly Pro Gly Met Glu
            180                 185                 190

Arg Ala Asp Leu Leu Asp Ile Asn Gly Gln Ile Phe Ala Glu Gln Gly
        195                 200                 205

Lys Ala Leu Asn Lys Ala Ala Ser Pro Asn Val Lys Val Leu Val Val
    210                 215                 220
```

```
Gly Asn Pro Cys Asn Thr Asn Ala Leu Ile Cys Leu Lys Asn Ala Pro
225                 230                 235                 240

Asn Ile Pro Ala Lys Asn Phe His Ala Leu Thr Arg Leu Asp Glu Asn
            245                 250                 255

Arg Ala Lys Cys Gln Leu Ala Leu Lys Ala Gly Val Phe Tyr Asp Lys
        260                 265                 270

Val Ser Asn Met Thr Ile Trp Gly Asn His Ser Thr Thr Gln Val Pro
    275                 280                 285

Asp Phe Leu Asn Ala Arg Ile Asn Gly Leu Pro Val Lys Glu Val Ile
290                 295                 300

Thr Asp His Lys Trp Leu Glu Glu Gly Phe Thr Glu Ser Val Gln Lys
305                 310                 315                 320

Arg Gly Gly Leu Leu Ile Gln Lys Trp Gly Arg Ser Ser Ala Ala Ser
                325                 330                 335

Thr Ala Val Ser Ile Val Asp Ala Ile Lys Ser Leu Val Thr Pro Thr
            340                 345                 350

Pro Glu Gly Asp Trp Phe Ser Thr Gly Val Tyr Thr Asp Gly Asn Pro
        355                 360                 365

Tyr Gly Ile Glu Glu Gly Leu Val Phe Ser Met Pro Cys Arg Ser Lys
    370                 375                 380

Gly Asp Gly Asp Tyr Glu Leu Val Lys Asp Val Glu Ile Asp Tyr
385                 390                 395                 400

Leu Arg Gln Arg Ile Ala Lys Ser Glu Ala Glu Leu Leu Ala Glu Lys
                405                 410                 415

Arg Cys Val Ala His Leu Thr Gly Glu Gly Ile Ala Tyr Cys Asp Leu
            420                 425                 430

Gly Pro Val Asp Thr Met Leu Pro Gly Glu Val
        435                 440

<210> SEQ ID NO 81
<211> LENGTH: 1208
<212> TYPE: DNA
<213> ORGANISM: Arabidopsis thaliana

<400> SEQUENCE: 81
acatcagcat ccacaaccaa tcagaggaca gaatcatatt tcacattttc aatccagacc    60
aatcaaaatc ctgaacgaat cctactctcc accttatagg agcagtttcg tctcttcctc   120
cttctttcac ttagctcttc ctagtgttaa accagagtaa agcttgaaac tttggactaa   180
aagaatggcg tctttgggtg tgtcggaaat gcttggtact ccccttaact tcagggcagt   240
ttcaagatcg tctgctccgt tggcatcaag cccatccacg ttcaagactg ttgctctctt   300
ctctaagaaa aagccagctc ctgctaagtc caaggctgtc tctgagacta gcgatgagct   360
cgccaagtgg tatggtcctg acaggagaat tttcttgcct gatggtcttt ggatagatc    420
agagatccca gagtacttaa acggtgaagt tgctggagat tatggttatg acccatttgg   480
tcttggaaag aagcctgaga ctttgctaa ataccaagct tttgaattga tccatgcgag   540
atgggctatg ttaggagcag ctggtttcat cattcctgaa gctttaaaca atatggcgc    600
taactgtggc cctgaagctg tctggtttaa gactggtgct tgcttcttg atggaaacac    660
attgaactac tttggcaaga acatccctat caaccttgtt ctcgccgtag ttgctgaggt   720
tgttctcctc ggtggagccg agtactacag aatcaccaac ggattggatt cgaggacaa    780
gctacaccca ggaggtccat tgatcctct aggccttgct aaggaccctg agcaaggagc   840
tcttctcaaa gtcaaagaga tcaagaacgg gagattagcc atgtttgcga tgctcggttt   900
```

```
cttatccaa gcgtatgtta ccggagaagg tcctgttgag aaccttgcaa agcatctcag      960
tgatcctttt ggaaacaact tgcttaccgt catcgctgga actgccgaga gagctcccac     1020
tctctaagcc atttctactt ttttaagag cttccaaaat gtacactttg ttcgattgga      1080 actcctttg acaatgttaa aaaaacttcc atctgaatct tcttgatata tttcaaattt      1140
tcaatggtgc tttatcatgc ttctaaggat atacatagtc acccattggt ttaatatttg     1200
ttgttacc                                                              1208
```

<210> SEQ ID NO 82
<211> LENGTH: 280
<212> TYPE: PRT
<213> ORGANISM: Arabidopsis thaliana

<400> SEQUENCE: 82

```
Met Ala Ser Leu Gly Val Ser Glu Met Leu Gly Thr Pro Leu Asn Phe
 1               5                  10                  15

Arg Ala Val Ser Arg Ser Ser Ala Pro Leu Ala Ser Ser Pro Ser Thr
            20                  25                  30

Phe Lys Thr Val Ala Leu Phe Ser Lys Lys Pro Ala Pro Ala Lys
        35                  40                  45

Ser Lys Ala Val Ser Glu Thr Ser Asp Glu Leu Ala Lys Trp Tyr Gly
    50                  55                  60

Pro Asp Arg Arg Ile Phe Leu Pro Asp Gly Leu Asp Arg Ser Glu
65                  70                  75                  80

Ile Pro Glu Tyr Leu Asn Gly Glu Val Ala Gly Asp Tyr Gly Tyr Asp
                85                  90                  95

Pro Phe Gly Leu Gly Lys Lys Pro Glu Asn Phe Ala Lys Tyr Gln Ala
           100                 105                 110

Phe Glu Leu Ile His Ala Arg Trp Ala Met Leu Gly Ala Ala Gly Phe
       115                 120                 125

Ile Ile Pro Glu Ala Leu Asn Lys Tyr Gly Ala Asn Cys Gly Pro Glu
   130                 135                 140

Ala Val Trp Phe Lys Thr Gly Ala Leu Leu Leu Asp Gly Asn Thr Leu
145                 150                 155                 160

Asn Tyr Phe Gly Lys Asn Ile Pro Ile Asn Leu Val Leu Ala Val Val
                165                 170                 175

Ala Glu Val Val Leu Leu Gly Ala Glu Tyr Tyr Arg Ile Thr Asn
            180                 185                 190

Gly Leu Asp Phe Glu Asp Lys Leu His Pro Gly Gly Pro Phe Asp Pro
        195                 200                 205

Leu Gly Leu Ala Lys Asp Pro Glu Gln Gly Ala Leu Leu Lys Val Lys
    210                 215                 220

Glu Ile Lys Asn Gly Arg Leu Ala Met Phe Ala Met Leu Gly Phe Phe
225                 230                 235                 240

Ile Gln Ala Tyr Val Thr Gly Glu Gly Pro Val Glu Asn Leu Ala Lys
                245                 250                 255

His Leu Ser Asp Pro Phe Gly Asn Asn Leu Leu Thr Val Ile Ala Gly
            260                 265                 270

Thr Ala Glu Arg Ala Pro Thr Leu
        275                 280
```

<210> SEQ ID NO 83
<211> LENGTH: 1990
<212> TYPE: DNA
<213> ORGANISM: Arabidopsis thaliana

<400> SEQUENCE: 83

```
ctcgcacaca cttctctctc tctctctctc tgcctccttt cggattcaaa tctcagatct      60
agctcaacca tggcgttgct cgtcgagaag acctcaagtg ccgtgaata caaggtcaaa     120
gacatgtctc aagccgattt cggtcgtctc gaactcgagc tcgccgaagt tgagatgcct     180
ggactcatgg cttgtcgtac cgaattcgga ccttctcagc cattcaaagg cgctagaatc     240
accggatctc ttcacatgac catccaaacc gccgtactca tcgaaaccct aactgctctc     300
ggtgctgaag tcagatggtg ttcctgcaac atcttttcca ctcaagacca cgccgccgca     360
gccatcgctc gtgactccgc cgctgttttc gcctggaaag gtgagactct tcaggagtac     420
tggtggtgta ccgagcgtgc tctagattgg ggtccaggtg gtggtcctga tctgattgtt     480
gatgatggtg gtgacgctac tcttttgatt catgagggtg ttaaagctga ggagatcttt     540
gagaagactg gtcaagttcc tgatcctact tctactgata accctgagtt tcagatcgtg     600
ttgtctatta tcaaggaagg tcttcaagtt gatcctaaga agtaccacaa gatgaaggag     660
agacttgttg gtgtctctga ggaaactacc actggtgtta agaggcttta ccagatgcag     720
caaaatggaa ctcttttgtt ccctgccatt aacgttaacg actctgtcac caagagcaag     780
ttcgacaact tgtatggttg ccgtcactca ctccctgatg gtctcatgag ggccactgat     840
gtcatgatcg ctggaaaggt tgctgttatc tgtggatatg gtgatgttgg aaagggttgt     900
gctgctgcca tgaagactgc tggtgctaga gtcattgtga ctgagattga tcccatctgt     960
gcccttcaag ctttgatgga aggacttcag gttcttaccc ttgaggatgt tgtctcagaa    1020
gctgatatct ttgtcaccac caccggtaac aaagacatca tcatggtcga ccacatgagg    1080
aagatgaaga caacgctat tgtgtgcaac attggtcact ttgacaatga gattgacatg    1140
cttggacttg agacttaccc tggtgtgaag cgtatcacca tcaagccaca gactgacagg    1200
tgggtgttcc cagagaccaa ggctggaatc attgtcttgg ctgagggtcg tctgatgaac    1260
ttgggttgtg ccactggtca cccaagtttc gtgatgtctt gctctttcac caaccaggtg    1320
attgcccagc tcgagctctg gaacgagaaa gcaagcggaa agtacgagaa gaaggtgtac    1380
gttcttccca gcatttggga tgagaaggtt gcattacttc acttgggcaa gcttggagcc    1440
aggcttacaa agctgtcaaa ggaccaatct gactacgtca gcattccaat tgagggacca    1500
tacaagcctc ctcactacag gtactgagag agagagagag tcgacaaagc ggttcaggtt    1560
cggatctact tgtggttttg tgttgggttg tggtgggaga gtggaacagt ttgagatatt    1620
ggtcttctga tgaagttgac caaatatcag tattaataag ggttattggc ttttgaaggt    1680
tgtgcttgtt ttctccattt ttcatgaaac ttaaattagt ttttggttta gtttccctct    1740
tgattttatt ttgtgtgttc tgtttagcgt tgtactcttc aaacaaatga gaaaccaaaa    1800
aaaaagggga aacttgtttt cggcatccca gtgttagcga cttttgttga atgaatgtct    1860
caaatgctca tctttaataa tgtgtgttag gacacgaaca acacatggtt cgattcgtgg    1920
gggattttat ggttgtagtt attatcgtac acgtttcaaa gttctcttaa gtattcaaaa    1980
aggcttttcc                                                           1990
```

<210> SEQ ID NO 84
<211> LENGTH: 485
<212> TYPE: PRT
<213> ORGANISM: Arabidopsis thaliana

<400> SEQUENCE: 84

```
Met Ala Leu Leu Val Glu Lys Thr Ser Ser Gly Arg Glu Tyr Lys Val
1               5                   10                  15
```

```
Lys Asp Met Ser Gln Ala Asp Phe Gly Arg Leu Glu Leu Glu Leu Ala
            20                  25                  30

Glu Val Glu Met Pro Gly Leu Met Ala Cys Arg Thr Glu Phe Gly Pro
        35                  40                  45

Ser Gln Pro Phe Lys Gly Ala Arg Ile Thr Gly Ser Leu His Met Thr
    50                  55                  60

Ile Gln Thr Ala Val Leu Ile Glu Thr Leu Thr Ala Leu Gly Ala Glu
65                  70                  75                  80

Val Arg Trp Cys Ser Cys Asn Ile Phe Ser Thr Gln Asp His Ala Ala
                85                  90                  95

Ala Ala Ile Ala Arg Asp Ser Ala Ala Val Phe Ala Trp Lys Gly Glu
            100                 105                 110

Thr Leu Gln Glu Tyr Trp Trp Cys Thr Glu Arg Ala Leu Asp Trp Gly
        115                 120                 125

Pro Gly Gly Gly Pro Asp Leu Ile Val Asp Asp Gly Gly Asp Ala Thr
    130                 135                 140

Leu Leu Ile His Glu Gly Val Lys Ala Glu Glu Ile Phe Glu Lys Thr
145                 150                 155                 160

Gly Gln Val Pro Asp Pro Thr Ser Thr Asp Asn Pro Glu Phe Gln Ile
                165                 170                 175

Val Leu Ser Ile Ile Lys Glu Gly Leu Gln Val Asp Pro Lys Lys Tyr
            180                 185                 190

His Lys Met Lys Glu Arg Leu Val Gly Val Ser Glu Glu Thr Thr Thr
        195                 200                 205

Gly Val Lys Arg Leu Tyr Gln Met Gln Gln Asn Gly Thr Leu Leu Phe
    210                 215                 220

Pro Ala Ile Asn Val Asn Asp Ser Val Thr Lys Ser Lys Phe Asp Asn
225                 230                 235                 240

Leu Tyr Gly Cys Arg His Ser Leu Pro Asp Gly Leu Met Arg Ala Thr
                245                 250                 255

Asp Val Met Ile Ala Gly Lys Val Ala Val Ile Cys Gly Tyr Gly Asp
            260                 265                 270

Val Gly Lys Gly Cys Ala Ala Ala Met Lys Thr Ala Gly Ala Arg Val
        275                 280                 285

Ile Val Thr Glu Ile Asp Pro Ile Cys Ala Leu Gln Ala Leu Met Glu
    290                 295                 300

Gly Leu Gln Val Leu Thr Leu Glu Asp Val Val Ser Glu Ala Asp Ile
305                 310                 315                 320

Phe Val Thr Thr Thr Gly Asn Lys Asp Ile Ile Met Val Asp His Met
                325                 330                 335

Arg Lys Met Lys Asn Asn Ala Ile Val Cys Asn Ile Gly His Phe Asp
            340                 345                 350

Asn Glu Ile Asp Met Leu Gly Leu Glu Thr Tyr Pro Gly Val Lys Arg
        355                 360                 365

Ile Thr Ile Lys Pro Gln Thr Asp Arg Trp Val Phe Pro Glu Thr Lys
    370                 375                 380

Ala Gly Ile Ile Val Leu Ala Glu Gly Arg Leu Met Asn Leu Gly Cys
385                 390                 395                 400

Ala Thr Gly His Pro Ser Phe Val Met Ser Cys Ser Phe Thr Asn Gln
                405                 410                 415

Val Ile Ala Gln Leu Glu Leu Trp Asn Glu Lys Ala Ser Gly Lys Tyr
            420                 425                 430

Glu Lys Lys Val Tyr Val Leu Pro Lys His Leu Asp Glu Lys Val Ala
```

```
                435              440              445
Leu Leu His Leu Gly Lys Leu Gly Ala Arg Leu Thr Lys Leu Ser Lys
    450              455              460

Asp Gln Ser Asp Tyr Val Ser Ile Pro Ile Glu Gly Pro Tyr Lys Pro
465              470              475              480

Pro His Tyr Arg Tyr
            485

<210> SEQ ID NO 85
<211> LENGTH: 735
<212> TYPE: DNA
<213> ORGANISM: Arabidopsis thaliana

<400> SEQUENCE: 85
agacaaatca gaagagagag atttagatat tgtagagtga gattctaaag agagagagag      60
agagagatat ggctagtgga atcgctcgtg gtcgtttagc tgaagagagg aaatcgtgga     120
ggaagaatca tcctcatggt tttgtggcaa agccggagac ggggcaggat ggaactgtga     180
atctaatggt gtggcattgc actatacctg gtaaagctgg gactgattgg aaggtggat      240 tctttccatt aacgatgcac ttcagtgagg attatccgag caaacctccg aaatgtaaat     300
ttccacaagg gttttttcca cctaatgtct atccatctgg aactgtctgt ctctctatcc     360
ttaacgagga ttatggatgg agaccagcca tcaccgtgaa gcagattctt gttggtattc     420
aggatttact tgacacaccg aatcccgctg accctgcaca gacagatggt tatcatctct     480
tctgtcagga tccagttgag tacaagaaaa gggtgaagct gcagtccaag cagtatcctg     540
ctcttgtcta aaacctcaaa aaagagaacg caccaaaact gatgacaagc tctgaatatt     600
ttctcgtctt gtgtcattat gtttagatgt cattgggtga ttgaaaactc ctcattttgg     660
caccttaaga cactggaatc tatttatttt cgaaaaaaaa ctcttctttc tctatttaac     720
tgttaatatt cttgg                                                     735

<210> SEQ ID NO 86
<211> LENGTH: 160
<212> TYPE: PRT
<213> ORGANISM: Arabidopsis thaliana

<400> SEQUENCE: 86

Met Ala Ser Gly Ile Ala Arg Gly Arg Leu Ala Glu Glu Arg Lys Ser
1               5                   10                  15

Trp Arg Lys Asn His Pro His Gly Phe Val Ala Lys Pro Glu Thr Gly
            20                  25                  30

Gln Asp Gly Thr Val Asn Leu Met Val Trp His Cys Thr Ile Pro Gly
        35                  40                  45

Lys Ala Gly Thr Asp Trp Glu Gly Gly Phe Phe Pro Leu Thr Met His
    50                  55                  60

Phe Ser Glu Asp Tyr Pro Ser Lys Pro Lys Cys Lys Phe Pro Gln
65                  70                  75                  80

Gly Phe Phe His Pro Asn Val Tyr Pro Ser Gly Thr Val Cys Leu Ser
                85                  90                  95

Ile Leu Asn Glu Asp Tyr Gly Trp Arg Pro Ala Ile Thr Val Lys Gln
            100                 105                 110

Ile Leu Val Gly Ile Gln Asp Leu Leu Asp Thr Pro Asn Pro Ala Asp
        115                 120                 125

Pro Ala Gln Thr Asp Gly Tyr His Leu Phe Cys Gln Asp Pro Val Glu
    130                 135                 140
```

Tyr Lys Lys Arg Val Lys Leu Gln Ser Lys Gln Tyr Pro Ala Leu Val
145                 150                 155                 160

<210> SEQ ID NO 87
<211> LENGTH: 1526
<212> TYPE: DNA
<213> ORGANISM: Arabidopsis thaliana

<400> SEQUENCE: 87

| | | | | | |
|---|---|---|---|---|---|
| tccccaattc | gtctcctcca | acagttttct | tcttctcttc | ttctttgggt | gttccttcca | 60 |
| ccaacggcag | aaatcgattt | ggcttaaatc | tccccctcct | ttcgatctct | ctgatcgccg | 120 |
| ccgggaacat | tcaatttccc | gggagttcaa | caaaaaaaaa | actctccgtt | tttattttc | 180 |
| ccccttttc | accggtggaa | gtttccggag | atggtgtcac | ccgaaaacgc | taattggatt | 240 |
| tgtgacttga | tcgatgctga | ttacggaagt | ttcacaatcc | aaggtcctgg | tttctcttgg | 300 |
| cctgttcagc | aacctattgg | tgtttcttct | aactccagtg | ctggagttga | tggctcggct | 360 |
| ggaaactcag | aagctagcaa | agaacctgga | tccaaaaaga | gggggagatg | tgaatcatcc | 420 |
| tctgccacta | gctcgaaagc | atgtagagag | aagcagcgac | gggacaggtt | gaatgacaag | 480 |
| tttatggaat | tgggtgcaat | tttggagcct | ggaaatcctc | ccaaaacaga | caaggctgct | 540 |
| atcttggttg | atgctgtccg | catggtgaca | cagctacggg | gcgaggccca | gaagctgaag | 600 |
| gactccaatt | caagtcttca | ggacaaaatc | aaagagttaa | agactgagaa | aaacgagctg | 660 |
| cgagatgaga | aacagaggct | gaagacagag | aaagaaaagc | tggagcagca | gctgaaagcc | 720 |
| atgaatgctc | ctcaaccaag | ttttttccca | gccccaccta | tgatgcctac | tgcttttgct | 780 |
| tcagcgcaag | gccaagctcc | tggaaacaag | atggtgccaa | tcatcagtta | cccaggagtt | 840 |
| gccatgtggc | agttcatgcc | tcctgcttca | gtcgatactt | ctcaggatca | tgtccttcgt | 900 |
| cctcctgttg | cttaatcaag | aaaaatcatc | aaccggtttg | cttcttgctt | ccgcttaaaa | 960 |
| gaaaagtctc | catttgtttt | gctctcctct | ctttctcggc | tttcttagtc | ttatcctttt | 1020 |
| gctttgtcgt | gttatcatcg | taactgttat | ctgttgaaca | atgatatgac | attgtaaact | 1080 |
| ccaattgctt | cgcgcaatgt | tatctattca | catgtaaatt | taagtagagt | ttggcagatc | 1140 |
| gtctctcact | ttatgtgttc | ttacattaat | acatagaatg | tggttacttc | ctcgccataa | 1200 |
| gagtttgaaa | gtacaaaaaa | ttagaaacag | gagagaccgc | aaaacatgat | ccggtagaga | 1260 |
| agtgaaaact | ccactgcaga | aaagtttgct | cctatatctt | gatctgtgaa | tctcctctct | 1320 |
| gggtgccaat | gtagaaaatg | gtcttggttt | gtgttatcat | gatgctctaa | tgtgacagct | 1380 |
| cttgataaat | ctgtcagaag | aatcaagata | cttagcccag | agaggacgta | gatgaggaaa | 1440 |
| tgctatatcc | agccaaggct | tagctcttcc | attgaaatga | acaacagcgg | cactttcagc | 1500 |
| atcggcatag | ctcgtggtct | cttggt | | | | 1526 |

<210> SEQ ID NO 88
<211> LENGTH: 234
<212> TYPE: PRT
<213> ORGANISM: Arabidopsis thaliana

<400> SEQUENCE: 88

Met Val Ser Pro Glu Asn Ala Asn Trp Ile Cys Asp Leu Ile Asp Ala
1               5                   10                  15

Asp Tyr Gly Ser Phe Thr Ile Gln Gly Pro Gly Phe Ser Trp Pro Val
                20                  25                  30

Gln Gln Pro Ile Gly Val Ser Ser Asn Ser Ser Ala Gly Val Asp Gly
        35                  40                  45

-continued

```
Ser Ala Gly Asn Ser Glu Ala Ser Lys Glu Pro Gly Ser Lys Lys Arg
    50                  55                  60
Gly Arg Cys Glu Ser Ser Ser Ala Thr Ser Ser Lys Ala Cys Arg Glu
65                  70                  75                  80
Lys Gln Arg Arg Asp Arg Leu Asn Asp Lys Phe Met Glu Leu Gly Ala
                85                  90                  95
Ile Leu Glu Pro Gly Asn Pro Pro Lys Thr Asp Lys Ala Ala Ile Leu
            100                 105                 110
Val Asp Ala Val Arg Met Val Thr Gln Leu Arg Gly Glu Ala Gln Lys
            115                 120                 125
Leu Lys Asp Ser Asn Ser Ser Leu Gln Asp Lys Ile Lys Glu Leu Lys
    130                 135                 140
Thr Glu Lys Asn Glu Leu Arg Asp Glu Lys Gln Arg Leu Lys Thr Glu
145                 150                 155                 160
Lys Glu Lys Leu Glu Gln Gln Leu Lys Ala Met Asn Ala Pro Gln Pro
                165                 170                 175
Ser Phe Phe Pro Ala Pro Pro Met Met Pro Thr Ala Phe Ala Ser Ala
            180                 185                 190
Gln Gly Gln Ala Pro Gly Asn Lys Met Val Pro Ile Ile Ser Tyr Pro
        195                 200                 205
Gly Val Ala Met Trp Gln Phe Met Pro Pro Ala Ser Val Asp Thr Ser
    210                 215                 220
Gln Asp His Val Leu Arg Pro Pro Val Ala
225                 230
```